United States Patent
Heath et al.

(10) Patent No.: US 10,221,214 B2
(45) Date of Patent: Mar. 5, 2019

(54) AKT-SPECIFIC CAPTURE AGENTS, COMPOSITIONS, AND METHODS OF USING AND MAKING

(71) Applicant: INDI MOLECULAR, INC., Culver City, CA (US)

(72) Inventors: James R. Heath, South Pasadena, CA (US); Arundhati Nag, Pasadena, CA (US); Samir Das, Pasadena, CA (US); Kaycie M. Deyle, Sylmar, CA (US); Steven Wesley Millward, Monrovia, CA (US); Paul Edward Kearney, Seattle, WA (US)

(73) Assignee: INDI MOLECULAR, INC., Culver City, CA (US)

( * ) Notice: Subject to any disclaimer, the term of this patent is extended or adjusted under 35 U.S.C. 154(b) by 0 days.

(21) Appl. No.: 14/949,236

(22) Filed: Nov. 23, 2015

(65) Prior Publication Data
US 2016/0251397 A1    Sep. 1, 2016

Related U.S. Application Data

(63) Continuation of application No. 13/546,575, filed on Jul. 11, 2012, now Pat. No. 9,239,332.

(60) Provisional application No. 61/598,614, filed on Feb. 14, 2012, provisional application No. 61/597,628, filed on Feb. 10, 2012, provisional application No. 61/506,560, filed on Jul. 11, 2011.

(51) Int. Cl.
| | |
|---|---|
| *C07K 7/02* | (2006.01) |
| *C12Q 1/48* | (2006.01) |
| *A61K 38/00* | (2006.01) |
| *A61K 38/08* | (2006.01) |
| *A61K 49/00* | (2006.01) |
| *A61K 51/08* | (2006.01) |
| *C07K 14/00* | (2006.01) |
| *C12N 15/10* | (2006.01) |
| *C12Q 1/6804* | (2018.01) |
| *G01N 33/573* | (2006.01) |
| *G01N 33/574* | (2006.01) |

(52) U.S. Cl.
CPC .............. *C07K 7/02* (2013.01); *A61K 38/08* (2013.01); *A61K 49/0043* (2013.01); *A61K 49/0056* (2013.01); *A61K 51/08* (2013.01); *C07K 14/001* (2013.01); *C12N 15/1058* (2013.01); *C12Q 1/485* (2013.01); *C12Q 1/6804* (2013.01); *G01N 33/573* (2013.01); *G01N 33/5748* (2013.01); *G01N 33/57449* (2013.01); *G01N 33/57496* (2013.01); *A61K 38/00* (2013.01); *G01N 2333/91205* (2013.01); *G01N 2333/91215* (2013.01)

(58) Field of Classification Search
None
See application file for complete search history.

(56) References Cited

U.S. PATENT DOCUMENTS

2011/0009896 A1    1/2011   Forsell et al.

FOREIGN PATENT DOCUMENTS

| JP | 2005-198643 | 7/2005 |
|---|---|---|
| WO | 2002/083064 A2 | 10/2002 |
| WO | WO 2002/083064 | 10/2002 |
| WO | 2005/113762 A1 | 12/2005 |
| WO | WO 2005/113762 | 12/2005 |
| WO | 2009/105746 A2 | 8/2009 |
| WO | WO 2009/105746 | 8/2009 |

OTHER PUBLICATIONS

European Patent Application No. 12811372.7, Office Action dated Feb. 3, 2016, 6 pages.
Journal of Biological Chemistry, 2004, vol. 279, No. 51, p. 53407-53418.
Japanese Patent Application No. 2014-520277, Office Action dated Mar. 29, 2016, 22 pages.
Milward, S.W et al.: "Iterative in Situ Click Chemistry Assembles a Branched Capture Agent and Allosteric Inhibitor for Akt1", JACS., vol. 133, No. 45, Sep. 30, 2011 (Sep. 30, 2011), pp. 18280-18288.
M. Subramanyam et al: "Inhibition of Protein Kinase Akt1 by Apoptosis Signal-regulating Kinase-1 (ASK1) Is Involved in Apoptotic Inhibition of Regulatory Volume Increase", Journal of Biological Chemistry, vol. 285, No. 9, Feb. 26, 2010 (Feb. 26, 2010), pp. 6109-6117.
Sarbassov D D et al: "Phosphorylation and regulation of Akt/PKB by the rictor-mTOR complex", Science, American Association for the Advancement of Science, US, vol. 307, No. 5712, Feb. 18, 2005 (Feb. 18, 2005), pp. 1098-1101.
International Search Report with Written Opinion corresponding to International Patent Application No. PCT/US2012/046253, dated Feb. 21, 2013.
Search Report with Search Opinion corresponding to European Patent Application No. 12811372, dated Jul. 1, 2015.
Agnew et al. (2009) "Iterative In Situ Click Chemistry Creates Antibody-like Protein-Capture Agents," Angewandte Chemie Int. Ed. 48(27):4944-4948.
Altomare et al. (2005) "Perturbations of the AKT signaling pathway in human cancer," Oncogene. 24:7455-7464.
Borrebaeck et al. (2000) "Antibodies in diagnostics—from immunoassays to protein chips," Immunol. Today. 21 (8):379-382.

(Continued)

*Primary Examiner* — Addison D Ault
(74) *Attorney, Agent, or Firm* — Pabst Patent Group LLP

(57) ABSTRACT

The present application provides stable peptide-based Akt capture agents and the use thereof as detection, diagnosis, and treatment agents. The application further provides novel methods of developing stable peptide-based capture agents, including Akt capture agents, using iterative on-bead in situ click chemistry.

13 Claims, 48 Drawing Sheets

Specification includes a Sequence Listing.

(56) References Cited

OTHER PUBLICATIONS

Carpten et al. (2007) "A transforming mutation in the pleckstrin homology domain of AKT1 in cancer," Nature. 448:439-445.
Chothia et al. (1989) "Conformations of immunoglobulin hypervariable regions," Nat. 342:877-883.
Cohen (2002) "Propotein kinases—the major drug targets of the twenty-first century?" Nat. Rev. Drug Discov. 1:309-315.
Coin et al. (2007) "Solid-phase peptide synthesis: from standard procedures to the synthesis of difficult sequences," Nat. Protocols. 2:3247-.
Erlanson et al. (2000) "Site-directed ligand discovery," Proc. Natl. Acad. Sci. USA. 97(17):9367-9372.
Gao et al. (2005) "Improved yields for baculovirus-mediated expression of human His6-PDK1 and His6-PKB-beta/Akt2 and characterization of phospho-specific isoforms for design of inhibitors that stabilize inactive conformations," Protein Expr Purif. 43:44-56.
Garcia-Echeverria et al. (2008) "Drug discovery approaches targeting the PI3K/Akt pathway in cancer," Oncogene. 27:5511-5526.
Hirai et al. (2010) "MK-2206, an Allosteric Akt Inhibitor, Enhances Antitumor Efficacy by Standard Chemotherapeutic Agents or Molecular Targeted Drugs In vitro and In vivo," Molecular Cancer Therapeutics. 9(7)1956-1967.
Hiromura et al. (2004) "Inhibition of Akt Kinase Activity by a Peptide Spanning the beta-A Strand of the Proto-oncogene TCL1," J. Biol. Chem. 279(51):53407-53418.
Jencks (1981) "On the attribution and additivity of binding energies," Proc. Natl. Acad. Sci. USA. 78(7):4046-4050.
Jen-Jacobsen (1997) "Protein-DNA Recognition Complexes: Conservation of Structure and Binding Energy in the Trasintion State," Biopolymers. 44:153-180.
Kijanka et al. (2009) "Rapid characterization of binding specificity and cross-reactivity of antibodies using recombinant human protein arrays," J. Immunol. Methods. 340:132-137.
Kirkland et al. (2009) "Non-ATP competitive protein kinase inhibitors as anti-tumor therapeutics," Biochem. Pharm. 77:1561-1571.
Klein et al. (2005) "Expression and purification of active PKB kinase from *Eschericia coli*," Protein Expr. Purif. 41:162-169.
Kumar et al. (2001) "Expression, purification, characterization and homology modeling of active Akt/PKB, a key enzyme involved in cell survival signaling," Biochim. Biophys. Acta. 1526:257-268.
Lam et al. (1991) "A new type of synthetic peptide library for identifying ligand-biding activity," Nat. 354:82-84.
Lindsley et al. (2008) "The Pl3K/Akt Pathway: Recent Progress in the Development of ATP-Competitive and Allosteric Akt Kinase Inhibitors," Current Cancer Drug Targets. 8:7-18.
Manetsch et al. (2004) "In Situ Click Chemistry: Enzyme Inhibitors Made to Their Own Specifications," J. Am. Chem. Soc. 126:12809-12818.
Mason et al. (2007) "Positive Aspects of Negative Design: Simultaneous Selection of Specificity and Interaction Stability," Biochem. 46:4804-4814.
Meyer et al. (2007) "Tethering Small Molecules to a Phage Display Library: Discovery of a Selective Bivalent Inhibitor of Protein Kinase A," J. Am. Chem. Soc. 129:13812-13813.
Michaud et al. (2003) "Analyzing antibody specificity with whole proteome microarrays," Nat. Biotechnol. 21:1509-1512.
Millward et al. (Sep. 30, 2011) "Iterative in Situ Click Chemistry Assembles a Branched Capture Agent and Allosteric Inhibitor for Akt1," J. Am. Chem. Soc. 133(45):18280-18288.
Mocharla et al. (2004) "In Situ Click Chemistry: Enzyme-Generated Inhibitors of Carbonic Anhydrase II," Angew. Chem. Int. Ed. 44:116-120.
Murray et al. (2002) "The consequences of translational and rotational entropy lost by small molecules on binding to proteins," J. Computer-Aided Mol. Design. 16:741-753.
Nguyen et al. (1998) "Exploiting the Basis of Proline Recognition by SH3 and WW Domains: Design of N-Substituted Inhibitors," Science. 282:2088-2092.
Nguyen et al. (2000) "Improving SH3 domain ligand selectivity using a non-natural scaffold," Chem. Biol. 7:463-473.
Niemeyer et al. (2005) "Immuno-PCR: high sensitivity detection of proteins by nucleic acid amplification," Trends Biotechnol. 23:208-216.
Obata et al. (2000) "Peptide and Protein Library Screening Defines Optimal Substrate Motifs for AKT/PKB," J. Biol. Chem. 275:36108-36115.
Posy et al. (2010) "Trends in Kinase Selectivity: Insights for Target Class-Focused Library Screening," J. Med. Chem. 54:54-66.
Rebecchi et al. (1998) "Pleckstrin Homology Domains: A Common Fold with Diverse Functions," Ann. Rev. Biophys. Biomol. 27:503-528.
Samson et al. (1995) "Identification of a Peptide Inhibitor Against Gal Phosphoglycerate Kinase of Trypanosoma brucei by a Synthetic Peptide Library Approach," Bioorg. Med. Chem. 3:257-265.
Samson et al. (1997) "Protein Chemistry and Structure: Screening a Random Pentapeptide Library, Composed of 14 D-Amino Acids against the COOH-terminal Sequence of Fructose-1,6-bisphosphate Aldolase from Trypanosoma brucei," J. Biol. Chem. 272:11378-11383.
Sarbassov et al. (2005) "Phosphorylation and regulation of Akt/PKB by the rictor-mTOR complex," Science. 307 (5712):1098-1101.
Schildback et al. (1991) "Altered Hapten Recognition by Two Anti-digoxin Hybridoma Variants Due to Variable Region Point Mutations," J. Biol. Chem. 266:4640-4647.
Shomin et al. (2009) "Staurosporine tethered peptide ligands that target cAMP-dependent protein kinase (PKA): Optimization and selectivity profiling," Bioorg. Med. Chem. 17:6196-6202.
Shuker et al. (1996) "Discovering High-Affinity Ligands for Proteins: SAR by NMR," Science. 274(5292):1531-1534.
Souroujon et al. (1998) "Peptide modulators of protein-protein interactions in intracellular signaling," Nat. Biotech. 16:919-924.
Statsuk et al. (2008) "Tuning a Three-Component Reaction for Trapping Kinase Substrate Complexes," J. Am. Chem. Soc. 130:17568-17574.
Subramanyam et al. (Feb. 26, 2010) "Inhibition of Protein Kinase Akt1 by Apoptosis Signal-regulating Kinase-1 (ASK1) Is Involved in Apoptotic Inhibition of Regulatory Volume Increase," Journal of Biological Chemistry. 285 (9):6109-6117.
Tornoe et al. (2002) "Peptidotriazoles on Solid Phase: [1,2,3]-Triazoles by Regiospecific Copper(I)-Catalyzed 1,3-Dipolar Cycloadditions of Termina Alkynes to Azides," J. Organic Chem. 67:3057-3064.
Towbin et al. (1979) "Electrophoretic transfer of proteins from polyacrylamide gels to nitrocellulose sheets: Procedure and some applications," Proc. Natl. Acad. Sci. 76(9):4350-4354.
Vivanco et al. (2002) "The Phosphatidylinositol 3-Kinase—AKT Pathway in Human Cancer," Nat. Rev. Cance. 2:489-500.
Whiting et al. (2006) "Inhibitors of HIV-1 Protease by Using in Situ Click Chemistry," Angew. Chem. Int. Ed. 45:1435-1439.
Xu et al. (2000) "Diversity in the CDR3 Region of VH Is Sufficient for Most Antibody Specificities," Immunity. 13:37-45.
Yang et al. (2004) "Akt/Protein Kinase B Signaling Inhibitor-2, a Selective Small Molecule Inhibitor of Akt Signaling with Antitumor Activity in Cancer Cells Overexpressing Akt," Cancer Research. 64:4394-4399.
Zarrinpar et al. (2003) "Optimization of specificity in a cellular protein interaction network by negative selection," Nature. 426:676-680.
Zemlin et al. (2003) "Expressed Murine and Human CDR-H3 Intervals of Equal Length Exhibit Distinct Repertoires that Differ in their Amino Acid Composition and Predicted Range of Structures," J. Mol. Biol. 334:733-749.

Figure 4

| AzX | X$_1$ | X$_2$ | X$_3$ | X$_4$ | X$_5$ | G | Y | M | mAb (Dilution) | SEQ ID NO: |
|---|---|---|---|---|---|---|---|---|---|---|
| Az4 | H | H | T | N | R | — | — | — | 5G3 (1:500) | 46 |
| Az8 | R | F | I | N | R | — | — | — | L32A4 (1:500) | 47 |
| Az8 | V | K | Y | R | L | — | — | — | L32A4 (1:500) | 48 |
| Az8 | I | L | S | R | L | — | — | — | L32A4 (1:500) | 49 |
| Az8 | I | A | P | D | P | — | — | — | L32A4 (1:500) | 50 |
| Az8 | G | P | D | P | G | — | — | — | L32A4 (1:500) | 51 |
| Az4 | S | E | R | T | W | — | — | — | 2H10 (1:1000) | 52 |
| Az2 | E | R | Y | Q | T | — | — | — | 5G3 (1:500) | 53 |
| Az8 | Q | T | D | S | H | — | — | — | 5G3 (1:500) | 54 |
| Az8 | Q | G | V | P | E | — | — | — | 5G3 (1:500) | 55 |
| Az4 | Y | N | V | Q | Y | — | — | — | 5G3 (1:500) | 56 |
| Az8 | H | H | K | G | A | — | — | — | 5G3 (1:500) | 57 |
| Az2 | E | F | H | P | I | — | — | — | L32A4 (1:500) | 58 |
| Az8 | I | G | V | G | D | — | — | — | L32A4 (1:500) | 59 |
| Az2 | E | W | L | F | N | — | — | — | L32A4 (1:500) | 60 |
| Az8 | I | A | E | P | I | — | — | — | L32A4 (1:500) | 61 |
| Az2 | A | T | E | D | T | — | — | — | L32A4 (1:500) | 62 |
| Az8 | V | G | D | T | T | — | — | — | L32A4 (1:500) | 63 |
| Az8 | H | A | E | P | Y | — | — | — | 5G3 (1:1000) | 64 |
| Az8 | L | G | T | Y | P | — | — | — | 5G3 (1:1000) | 65 |
| Az8 | H | G | I | Q | P | — | — | — | 5G3 (1:1000) | 66 |
| Az8 | I | S | H | D | S | — | — | — | 5G3 (1:1000) | |

Figure 6

| AzX | $X_1$ | $X_2$ | $X_3$ | $X_4$ | $X_5$ | G | Y | M | Repeats | SEQ ID NO: |
|---|---|---|---|---|---|---|---|---|---|---|
| Az8 | V | T | Y | R | R | — | — | — | 5 | 68 |
| Az8 | I | A | V | R | R | — | — | — | 4 | 69 |
| Az8 | I | T | V | R | R | — | — | — | 4 | 70 |
| Az8 | Q | F | V | R | R | — | — | — | 3 | 71 |
| Az8 | Q | T | V | R | R | — | — | — | 3 | 72 |
| Az8 | Q | A | V | R | R | — | — | — | 3 | 73 |
| Az8 | V | F | V | R | R | — | — | — | 2 | 74 |
| Az8 | H | A | V | R | R | — | — | — | 2 | 75 |
| Az8 | V | F | E | R | R | — | — | — | 2 | 76 |
| Az8 | V | F | E | R | L | — | — | — | 1 | 77 |
| Az8 | V | F | Y | R | L | — | — | — | 1 | 78 |
| Az8 | V | F | Y | R | L | — | — | — | 1 | 79 |
| Az8 | V | A | Y | R | L | — | — | — | 1 | 80 |
| Az8 | V | F | Y | T | R | — | — | — | 1 | 81 |
| Az8 | V | G | Y | R | I | — | — | — | 1 | 82 |
| Az8 | V | G | Y | R | I | — | — | — | 1 | 83 |

Anchor Peptide
(SEQ ID NO: 24)

Figure 8

| Pra | $X_1$ | $X_2$ | $X_3$ | $X_4$ | $X_5$ | G | M | SEQ ID NO: |
|---|---|---|---|---|---|---|---|---|
| Pra | F | P | F | F |   | — | — | 85 |
| Pra | S | F | F | W |   | — | — | 86 |
| Pra | F | W | R | I | Y | — | — | 87 |
| Pra | F | W | F | L | R | — | — | 88 |
| Pra | F | F | N | F | R | — | — | 89 |
| Pra | F | F | F | R | T | — | — | 90 |
| Pra | A | F | F | R | G | — | — | 91 |
| Pra | R | F | Q | Y | Y | — | — | 92 |
| Pra | W | D | T | D | S | — | — | 93 |

SEQ ID NO: 43

SEQ ID NO: 23

Figure 10

| AzX | $X_1$ | $X_2$ | $X_3$ | $X_4$ | $X_5$ | SEQ ID NO: |
|---|---|---|---|---|---|---|
| Az8 | R | R | D | V | A | 95 |
| Az8 | H | D | K | I | I | 96 |
| Az8 | K | H | L | G | H | 97 |
| Az8 | K | T | H | R | H | 98 |
| Az8 | H | L | H | P | K | 99 |
| Az8 | A | K | H | S | H | 100 |
| Az8 | S | K | H | H | K | 101 |
| Az8 | G | R | H | K | H | 102 |
| Az8 | E | H | L | S | R | 103 |
| Az8 | N | K | I | Y | K | 104 |
| Az8 | A | S | L | N | H | 105 |
| Az8 | D | Q | T | D | K | 106 |
| Az8 | A | A | N | H | E | 107 |
| Az4 | K | H | G | D | F | 108 |
| Az4 | H | K | F | K | H | 109 |
| Az4 | K | K | H | D | H | 110 |
| Az4 | H | L | L | H | G | 111 |
| Az4 | L | H | D | H | K | 112 |
| Az2 | R | R | E | S | K | 113 |
| Az2 | R | V | H | I | F | 114 |
| Az2 | K | W | H | K | K | 115 |
| Az2 | L | K | H | D | K | 116 |
| Az2 | L | L | H | R | H | 117 |
| Az2 | F | A | Q | N | Y | 118 |

Figure 11

| Az8 | $X_1$ | $X_2$ | $X_3$ | $X_4$ | $X_5$ | SEQ ID NO: |
|-----|----|----|----|----|----|------------|
| Az8 | L | R | K | I | G | 120 |
| Az8 | L | K | I | F | G | 121 |
| Az8 | E | K | D | H | G | 122 |
| Az8 | E | L | E | H | I | 123 |
| Az8 | R | H | E | R | I | 124 |
| Az8 | K | A | H | K | H | 125 |

Triligand branch
SEQ ID NO: 19

Anchor ligand
SEQ ID NO: 34

Biligand branch
SEQ ID NO: 23

SEQ ID NO: 43

Fluorescein

SEQ ID NO: 18

SEQ ID NO: 43

SEQ ID NO: 23

Figure 31

SEQ ID NO:1

```
msdvaivkeg wlhkrgeyik twrpryfllk ndgtfigyke rpqdvdqrea plnnfsvaqc   60
qlmkterprp ntfiirclqw ttviertfhv etpeereewt taiqtvadgl kkqeeeemdf  120
rsgspsdnsg aeemevslak pkhrvtmnef eylkllgkgt fgkvilvkek atgryyamki  180
lkkevivakd evahtltenr vlqnsrhpfl talkysfqth drlcfvmeya nggelffhls  240
rervfsedra rfygaeivsa ldylhseknv vyrdlklenl mldkdghiki tdfglckegi  300
kdgatmktfc gtpeylapev ledndygrav dwwglgvvmy emmcgrlpfy nqdheklfel  360
ilmeeirfpr tlgpeaksll sgllkkdpkq rlgggsedak eimqhrffag ivwqhvyekk  420
lsppfkpqvt setdtryfde eftaqmitit ppdqddsmec vdserrphfp qfsysassta  480
```

Anchor

Ac2-Tz4-PEG2-Biotin coupled to
WKVKL (SEQ ID NO: 4)

Biligand

WKVKL (SEQ ID NO: 4) and
FYGNH (SEQ ID NO: 126)
biligand n-terminal triligand

WKVKL (SEQ ID NO: 4), FYGNH (SEQ ID NO: 126) and YYRFG (SEQ ID NO: 127) triligand c-terminal
triligand WKVKL (SEQ ID NO: 4),
FYGNH (SEQ ID NO: 126) and HDGGF (SEQ ID NO: 128) triligand dimer of n-terminal triligand YYRFG (SEQ ID NO: 127), FYGNH (SEQ ID NO: 126), and WKVKL (SEQ ID NO: 4) triligand dimer Biotin -

MSDVAIVKEGWLHKRGKY[Pra]KTWRPRYFLLKNDG

AKT-SPECIFIC CAPTURE AGENTS, COMPOSITIONS, AND METHODS OF USING AND MAKING

RELATED APPLICATIONS

This application is a continuation of U.S. patent application Ser. No. 13/546,575, filed Jul. 11, 2012, and claims priority from U.S. Provisional Patent Application No. 61/506,560, filed on Jul. 11, 2011, U.S. Provisional Patent Application No. 61/597,628, filed on Feb. 10, 2012 and U.S. Provisional Patent Application No. 61/598,614, filed on Feb. 14, 2012, incorporated by reference herein in their entireties.

STATEMENT OF GOVERNMENT INTEREST

This invention was made with government support under Grant No. CA119347 awarded by the National Institutes of Health and under Grant No. W911 NF-09-D-0001 awarded by the US Army Research Office. The government has certain rights in the invention.

BACKGROUND

The early detection of diseases including cancer requires multiplex measurements of key protein biomarkers in biological samples. The availability of high-affinity, highly selective molecular moieties that recognize biomarkers from complex biological mixtures is a critical component for accurate detection of proteins that may indicate disease.

Akt mediates signal transduction from the plasma membrane (cytokine receptors, GPCRs) to downstream effector molecules that control cell growth, apoptosis, and translation (Vivanco 2002). Based on its ability to block apoptosis and thereby promote cell survival, Akt overexpression and/or hyperactivation is implicated in many types of cancer (Altomare 2005). Therefore, Akt provides an attractive target as a biomarker for specific cancer types, as well as a potential therapeutic. Most current biomarker assays utilize antibodies. It is challenging to produce stable antibodies for complex targets. Thus, there is a need in the art for synthetic, stable capture agents that can be used reproducibly and effectively in bioassays and as a therapeutic treatment.

SUMMARY

Provided herein in certain embodiments are stable, synthetic Akt capture agents that specifically bind Akt. In certain embodiments, these Akt capture agents are triligands comprising an anchor ligand, secondary ligand, and tertiary ligand. In certain embodiments, the anchor ligand comprises the peptide sequence Az8-VFYRLGY-CONH$_2$. In certain embodiments, the secondary ligand comprises the peptide sequence Pra-FWFLRG-CONH$_2$. In certain embodiments, the tertiary ligand comprises the peptide sequence Ac-C8-RHERI-CONH$_2$. In certain embodiments, the linkage between one or more of the anchor ligand, secondary ligand, and tertiary ligand comprises a 1,4-substituted-1,2,3-triazole residue (Tz4). In certain embodiments, the Akt capture agents provided herein have the structure:

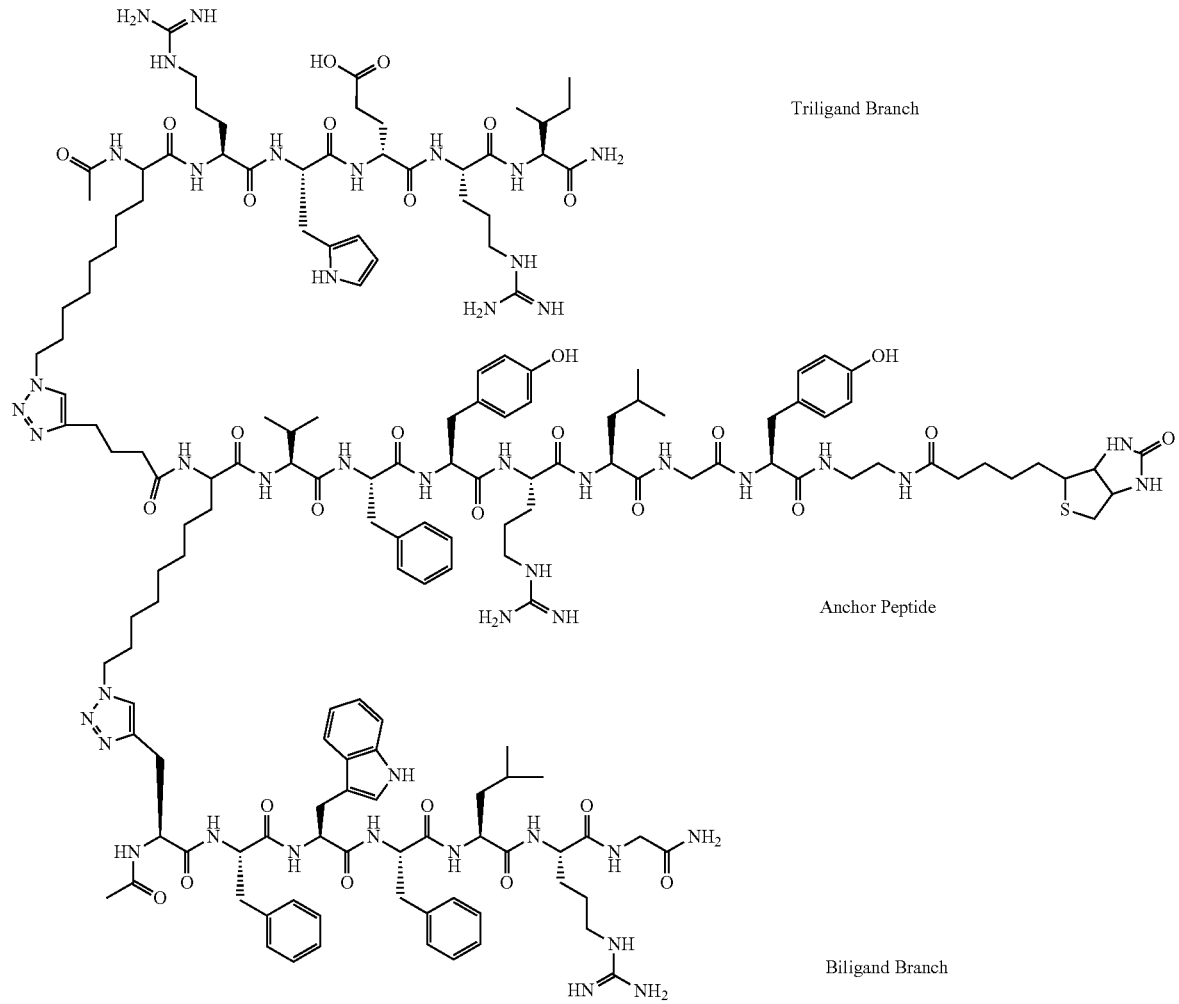 [SMILES: CCC(C)[C@H](NC(=O)[C@H](CCCNC(=N)N)NC(=O)[C@@H](CCC(=O)O)NC(=O)[C@H](Cc1ccc[nH]1)NC(=O)[C@H](CCCNC(=N)N)NC(=O)C(CCCCCCCCn1cc(CCCC(=O)NC(CCCCCCCCn2cc(C[C@H](NC(C)=O)C(=O)N[C@@H](Cc3ccccc3)C(=O)N[C@@H](Cc3c[nH]c4ccccc34)C(=O)N[C@@H](Cc3ccccc3)C(=O)N[C@@H](CC(C)C)C(=O)N[C@@H](CCCNC(=N)N)C(=O)NCC(N)=O)nn2)C(=O)N[C@H](C(=O)N[C@@H](Cc2ccccc2)C(=O)N[C@@H](Cc2ccc(O)cc2)C(=O)N[C@@H](CCCNC(=N)N)C(=O)N[C@@H](CC(C)C)C(=O)NCC(=O)N[C@@H](Cc2ccc(O)cc2)C(=O)NCCNC(=O)CCCCC2SCC3NC(=O)NC32)C(C)C)nn1)NC(C)=O)C(N)=O]

Triligand Branch

Anchor Peptide

Biligand Branch

In certain embodiments, the Akt capture agents provided herein are stable across a wide range of temperatures, pH's, storage times, storage conditions, and reaction conditions, and in certain embodiments the capture agents are more stable than a comparable antibody or biologic. In certain embodiments, the capture agents are stable in storage as a lyophilized powder. In certain embodiment, the capture agents are stable in storage at a temperature of about −80° C. to about 40° C. In certain embodiments, the capture agents are stable in storage at room temperature. In certain embodiments, the capture agents are stable in human serum for at least 24 hours. In certain embodiments, the capture agents are stable at a pH in the range of about 3 to about 8.

In certain embodiments, the capture agents provided herein comprise one or more detectable labels. In certain of these embodiments, the label is copper-DOTA. In other embodiments, the detectable label is selected from $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the detectable label is selected from $^{123}$I, $^{131}$I, $^{67}$Ga, $^{111}$In and $^{99m}$Tc. In other embodiments, the label is a fluorescent label.

In certain embodiments, the Akt capture agents provided herein bind to a non-ATP and/or non-peptide substrate binding site of Akt. In certain of these embodiments, the Akt capture agents function as allosteric inhibitors of Akt activity.

In certain embodiments, kits are provided that comprise one or more of the Akt capture agents provided herein. In certain of these embodiments, the kits include instructions for use.

In certain embodiments, methods are provided for identifying, detecting, quantifying, or separating Akt in a biological sample using the capture agents provided herein. In certain embodiments, these methods are immunoassays where the Akt capture agent is used as a replacement for an antibody or its equivalent. In certain embodiments, the immunoassay is a Western blot, pull-down assay, dot blot, or ELISA.

In certain embodiments, methods are provided fur diagnosing or classifying a condition associated with increased Akt expression and/or activity in a subject in need thereof using the capture agents provided herein. In certain of these embodiments, the condition is cancer, and the methods are used to diagnose and/or stage the cancer.

In certain embodiments, methods are provided for treating a condition associated with increased Akt expression and/or activity in a subject in need thereof. In certain embodiments, these methods comprise administering to a subject a therapeutically effective amount of an Akt capture agent as provided herein. In certain embodiments, the condition being treated is cancer. In certain embodiments, the Akt capture agents provided herein function as immunotherapeutics.

In certain embodiments, methods are provided for inhibiting Akt activity in vivo or in vitro using an Akt capture agent as provided herein. In certain of these embodiments, the Akt capture agent inhibits Akt activity in an allosteric manner. In certain embodiments, inhibition of Akt activity results in an effective decrease in Akt levels and/or a change in Akt conformation.

In certain embodiments, the use of one or more Akt capture agents is provided for use in preparing a medicament for treating a condition associated with increased Akt expression and/or activity in a subject in need thereof.

In certain embodiments, methods are provided for synthesizing the Akt capture agents disclosed herein.

In certain embodiments, methods are provided for generating a capture agent for a target protein. In certain embodiments, the target protein is a kinase, and in certain of these embodiments the kinase is Akt. In certain embodiments, these methods comprise the following steps:
  (a) identifying an anchor ligand by the following steps:
    (i) contacting the target protein with one or more target protein inhibitors;
    (ii) preparing a first plurality of candidate peptides to select an anchor ligand for the target protein;
    (iii) contacting the target protein with the first plurality of candidate peptides;
    (iv) selecting a candidate peptide with affinity for the target protein as the anchor ligand, wherein the candidate peptide binds to the target protein outside of an active site; and
    (v) sequencing the anchor ligand;
  (b) identifying a secondary ligand by the following steps:
    (i) preparing an anchor ligand selection block comprising the anchor ligand and an azido group or an alkynyl group;
    (ii) preparing a second plurality of candidate peptides to select a secondary ligand for the target protein, the second plurality of peptides comprising an azido group or an alkynyl group if the anchor ligand selection block comprises an alkynyl group and azido group respectively;
    (iii) contacting the anchor ligand selection block and the second plurality of peptides with the target protein;
    (iv) providing a capture agent biligand by forming a disubstituted 1,2,3-triazole linkage between the anchor ligand selection block and the secondary ligand wherein the azido and alkynyl group of the anchor ligand selection block and the secondary ligand are brought in close proximity by binding to the target protein;
    (v) selecting the capture agent biligand that has an affinity with the target protein; and
    (vi) sequencing the secondary ligand;
  (c) identifying a tertiary ligand and, optionally, additional ligands by the following steps:
    (i) preparing a biligand selection block comprising an azido group or an alkynyl group; and
    (ii) repeating steps (b)(ii) to (b)(vi) using a third plurality, fourth plurality, etc., of candidate peptides until a capture agent having desired binding affinity to the target protein is obtained.

In certain embodiments, the active site is an ATP or substrate peptide binding site.

In certain embodiments, methods are provided for evaluating the efficiency and/or selectively of an in situ click reaction between a first and second ligand using QPCR. In certain embodiments, the first ligand is an anchor ligand and the second ligand is a secondary ligand. In other embodiments, the first ligand is a biligand and the second ligand is a tertiary ligand. In certain embodiments, these methods comprise the following steps:
  (a) carrying out an in situ click reaction between a soluble biotinylated first ligand and an on-bead second ligand;
  (b) removing non-bound first ligand, such that all remaining first ligand is bound to said second ligand to form a ligand complex;
  (c) contacting the ligand complex with a streptavidin-oligonucleotide QPCR template;
  (d) subjecting the ligand complex-QPCR template to QPCR; and (e) determining the cycle threshold for the QPCR reaction.

In certain embodiments, the capture agent is stable in storage as a lyophilized powder. In other embodiments, the capture agent is stable in storage at a temperature of about −80° C. to about 40° C. In other embodiments, the capture agent is stable in storage at room temperature. In other embodiments the capture agent is stable in human serum for at least 24 hours. In other embodiments the capture agent is stable at a pH in the range of about 3 to about 8. In other the capture agent is labeled with copper-DOTA.

BRIEF DESCRIPTION OF DRAWINGS

FIG. 4: Sequences obtained from the initial anchor peptide screen. Antibodies and their dilutions are shown (5G3=mAb against kinase domain (CST), L32A4=mAb against phospho-T308 (CST), 2H10=mAb against C-terminal peptide (CST). Positions with a strong consensus residue(s) are shaded.

FIG. 6: Sequences obtained from the anchor peptide screen with focused library. The number of times each sequence appeared is shown to the right. Positions with a strong consensus residue(s) are shaded.

FIG. 8: Sequences obtained from the biligand peptide screen with a naïve library. Positions with a strong consensus residue(s) are shaded

FIG. 10: Sequences obtained from the tertiary peptide screen with a naïve library. Positions with a strong consensus residue(s) are shaded FIG. 11: Sequences obtained from the tertiary peptide screen with a focused library. Positions with a strong consensus residue(s) are shaded. The focused library was of the form: $NH_2$-Az8-$X_1$-$X_2$-$X_3$-$X_4$-$X_5$-GYM-TG (SEQ ID NO: 21) where $X_1$=A, E, H, K, L, R; $X_2$=A, H, K, L, R; $X_3$=D, H, K, L, E; $X_4$=D, H, I, K, N, R, S; $X_5$=F, G, H, I, K.

FIG. 16A. The secondary ligand is synthesized on TentaGel (red letters) with an N-terminal propargylglycine and the soluble anchor ligand is appended with a C-terminal biotin (black) and an N-terminal azido-amino acid. These are incubated together under conditions described below. After the reaction is completed, the beads are washed, stripped, and probed with a streptavidin-DNA Conjugate (red) to detect the formation of the triazole. The beads were then subjected to on-bead QPCR. FIG. 16B. QPCR results. The reaction conditions were 1. Akt1+biotinylated anchor peptide+Bead, 2. Biotinylated anchor peptide+Bead, 3. Bead, and 4) CuI/Ascorbic Acid+biotinylated anchor peptide+Bead. The red bars represent the reaction configuration described in (a); the black bars represent reactions where the anchor peptide is synthesized on bead and the biotinylated secondary peptide is in solution (inverted configuration). The error bars represent standard error. In this experiment, the efficiency of the on-bead in situ click reaction is approximately 10-fold higher in the presence of the Akt1 target than in its absence. For comparison, the efficiency Cu(I)-catalyzed click reaction is approximately 4 orders of magnitude higher than the protein-templated reaction. FIG. 16C. Standard curve of SA-template. Each point is the mean Ct of duplicate experiments.

FIG. 22A. Velocity vs. [Peptide substrate] with varying concentration of inhibitory triligand. FIG. 22B. Velocity vs. [ATP] with varying concentration of inhibitory triligand. In both experiments, the Vmax of Akt1 is decreasing as the [Triligand] increases, evidence that the triligand is not competing with either substrate. The figures below each graph illustrate the conclusion that the triligand was not competitive with respect to either the peptide or ATP binding site.

FIG. 23A. Plot of $1/K_M(app)$ vs. [Triligand]. $K_M(app)$ were obtained from nonlinear regression analysis of velocity vs. [Peptide] curves obtained with varied concentrations of triligand (Graphpad). The error bars represent the standard error of $K_M(app)$ by nonlinear regression. 95% confidence intervals are shown as dotted lines. The X-intercept ($-K_i'$) was found to be 3600 nM. FIG. 23B. Plot of $1/V_{max}(app)$ vs. [Triligand]. Values for $V_{max}(app)$ and standard error were obtained by nonlinear regression as described above. The X-intercept was found to be 1.7 FIG. 23C. Dixon plot of 1/v vs. [Triligand] at various [Peptide]. Data from low peptide concentrations were removed to account for possible substrate depletion. The parallel lines are diagnostic for uncompetitive inhibition with respect to peptide. FIG. 23D. Cornish-Bowden plot of [Peptide]/v vs. [Triligand] at various [Peptide]. The intersection of the lines gives the $-K_i'$. The shape of this plot is diagnostic for uncompetitive inhibition with respect to peptide FIG. 24A. Plot of $1/K_M(app)$ vs. [Triligand]. $K_M(app)$ were obtained from nonlinear regression analysis of velocity vs. [ATP] curves obtained with varied concentrations of triligand (Graphpad). The error bars represent the standard error of $K_M(app)$ by nonlinear regression. The negative slope of the line was taken as an indication that $K_M$ was unchanged during inhibition with the triligand. FIG. 24B. Plot of $1/V_{max}(app)$ vs. [Triligand]. Values for $V_{max}(app)$ and standard error were obtained by nonlinear regression as described above and 95% confidence intervals are shown as dotted lines. The X-intercept was found to be 5.8 μM with wide error range based on the 95% Cl. FIG. 24C. Dixon plot of 1/v vs. [Triligand] at various [ATP]. Data from low ATP concentrations were removed due high counting error resulting from low counts per minute (cpm). The lines converged on a common X-intercept which was used to determine $K_i$. The shape of plot is consistent with noncompetitive inhibition with respect to ATP.

FIG. 31: Amino acid sequence of *H. sapiens* Akt1 (GenBank accession number AAL55732).

FIG. 33A depicts incubation of the polypeptide fragment containing the epitope, and the substituted or altered amino acid with a large molecular library. FIG. 33B shows the incubation step. FIG. 33C shows use of the label on the polypeptide fragment to generate a signal that discriminates those elements of the molecular library that are covalently coupled to the polypeptide fragment, from those library elements that are not. FIG. 33D shows separation of molecular library elements that are covalently coupled to the peptide from those that are not.

FIG. 35A. Space filling model showing the relative size of the metallorganic-labeled pS474 group, relative to the rest of the 32-mer fragment. FIG. 35B. The 32-mer polypeptide fragment, corresponding to amino acids 450-481 of Akt2, and with a chemically modified p-S474 group. In this case, (2) and (4) of FIG. 1 are the same, and are a single amino acid (phospho-S474), and the label (7) of FIG. 1 is included as a biotin group (indicated by the 'B') that is part of the phospho-chelating metallorganic ligand. For the screen, this modified polypeptide fragment is incubated with a bead based library of 5-mer peptides. Those peptides are comprised of artificial and non-natural amino acids, and are comprehensive, based upon a basis set of 18 amino acids. Thus, the peptide library contains ~2 million distinct molecules. After incubation, the bead based library is exhaustively washed to remove any free polypeptide material. Only the hit beads have polypeptide bound. Hit beads can be identified via using the biotin label to attach a streptavidin-alkaline phosphatase unit. The alkaline phosphatase enzyme is exposed to its substrate, which generates a precipitate, turning the hit beads turquoise blue. Hhit beads are then separated, and the 5-mer peptide sequences on those hit beads are identified via standard sequencing methods. The initial anchor was extended into a biligand using the same Zn chelator/p-Ser 474 polypeptide complex. Once the consensus biligand had been identified, two separate approaches were used to build a triligand: For the first approach, a n-terminal triligand was prepared by modifying the biligand at the n-terminus with an azide and then screening for in situ click hits (using an acetylene-presenting OBOC library), using the whole Akt2 protein as the target/catalyst; For the second approach, a c-terminal triligand was prepared by modifying the biligand at the c-terminus with an azide, and the screening for in situ click hits (using an acetylene-presenting OBOC library) using the whole Akt2 protein as the target/catalyst.

FIG. 36A. An anchor ligand, identified from basic epitope targeting screen. FIG. 36B. A biligand, FIG. 36C. An n-terminal triligand. FIG. 36D. A c-terminal triligand (TRI GF). FIG. 36E. A dimerized n-terminal triligand. Note: These capture agents are directed to a region near, but not including, p-Ser474. Thus, the phosphorylation status of Ser474 is not relevant to the capture agent (PCC) binding.

FIG. 37A. A bar graph a illustrating epitope selectivity for the anti-Ser474 Akt2 PCC biligand and triligand. The target peptide is the c-terminal 32-mer fragment of Akt2 that contains the p-Ser474 region. The off target peptide is a 32-mer fragment, chosen from a different part of the protein. For the target peptide, a high level of fraction bound is recorded for both the biligand and triligand. This fraction is 5-10-fold higher than what is observed for the off-target peptide. FIG. 37B. A line graph showing results from single component ELISA assays. FIG. 37C. A Western blot of c-terminal 32-mer fragment of Akt2 bound by the monoligand, biligand and triligand.

FIG. 39A is a 3D image of Pleckstrin Homology Domain (first 124 amino acids of Akt1 sequence) highlighting the 33-mer fragment (pink) that was chosen due to its containment of the E17K mutation as well as its folded structure. The E17K mutation is highlighted in blue, and the I19[Pra] in vitro click handle substitution is highlighted in yellow. FIG. 39B shows the 33-mer fragment used for epitope targeting in OBOC screening. FIG. 39C shows the MALDI spectra of the 33-mer fragment as shown in FIG. 39B.

FIG. 40A. Preclear: Library beads are incubated with streptavidin-alkaline phosphatase conjugate to remove any library beads that bind to this or the BCIP reagents. FIG. 40B. Screen: Precleared library beads are incubated with the 33-mer target peptide containing an azide in situ click handle. The fragment catalyzes triazole formation between the alkyne on the 33-mer target and the azide on beads that contain peptide sequences that bind specifically to the 33-mer in a close enough proximity to the alkyne substitution for a click reaction to occur without copper. The unclicked peptide is then stripped from the beads and the remaining covalently attached 33-mer is detected by streptavidin-alkaline phosphatase with BCIP development.

DETAILED DESCRIPTION OF THE INVENTION

Figure 1:
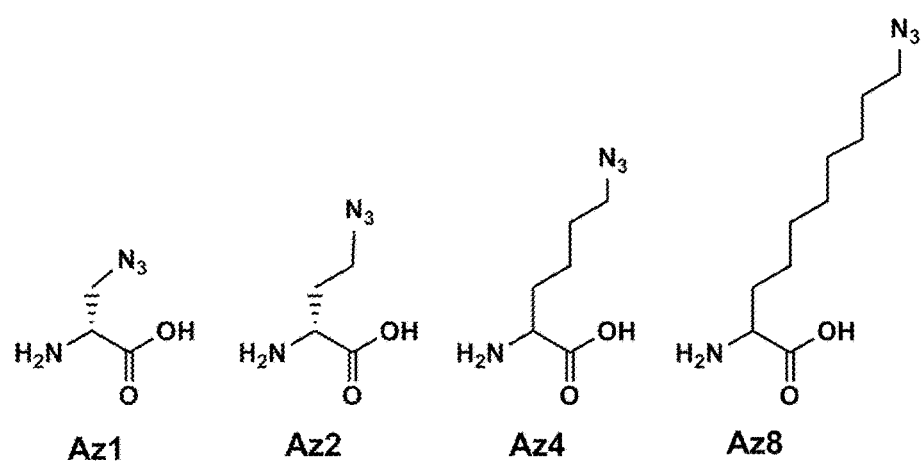
FIG. 1: Structure of azido amino acids Az1, Az2, Az4, and Az8.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Definitions

The term "allosteric" refers to a change in the shape and activity of a protein, (eg. an enzyme), when it binds with a molecule on a region other than its active site. The binding may effect the biological function that is not directly involved in the function (an allosteric effector), or the regulation of an enzyme involving cooperativity between multiple binding sites (allosteric sites). "Allosteric regulation" is the regulation of an enzyme or other protein by binding an effector molecule at a protein's site other than the protein's active site.

The term "allosteric site" refers to the site on an enzyme molecule that binds with a nonsubstrate molecule, inducing a conformational change that results in an alteration of the affinity of the enzyme for its substrate.

The term "capture agent" as used herein refers to a composition that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules. In some aspects a capture agent is a protein catalyzed capture agent (PCC).

The term "epitope" as used herein refers to a distinct molecular surface of a target protein capable of catalyzing the assembly of a PCC from a library of molecular building blocks. Typically, the epitope is a polypeptide and it can act on its own as a finite sequence of 20-40 amino acids.

The term "epitope targeting" as used herein refers to a process by which an anchor ligand is selected by an epitope-catalyzed process where a synthetic polypeptide epitope presenting a first functional group interacts with a library of possible anchor ligands presenting a second functional group to result in the formation of a covalent linkage between the polypeptide and anchor ligand. The selected anchor ligand displays affinity toward both the polypeptide epitope and the full-length (native) target protein. The polypeptide epitope dictates the sequence and binding site of the anchor ligand, and ultimately the capture agent or PCC.

The same epitope, now existing as part of the larger protein, can be involved in catalyzing the assembly of a PCC biligand from the previously selected anchor ligand (modified with a second functional group) and a library of molecular building blocks (modified with a first functional group) in a protein-catalyzed process. This protein-catalyzed process can then repeated to assemble a PCC triligand from the previously selected biligand (modified with a third functional group) and a library of molecular building blocks (modified with a fourth functional group).

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The terms "specific binding," "selective binding," "selectively binds," or "specifically binds" as used herein refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower.

The term "$K_D$" as used herein refers to the dissociation equilibrium constant of a particular antibody-antigen interaction. Typically, the antibodies of the invention bind to ALK with a dissociation equilibrium constant ($K_D$) of less than approximately $10^{-6}$M, $10^{-7}$M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" ($sec^{-1}$) as used herein refers to the dissociation rate constant of a particular antibody-antigen interaction. Said value is also referred to as the $k_{off}$ value.

The term "$k_a$" ($M^{-1} \times sec^{-1}$) as used herein refers to the association rate constant of a particular antibody-antigen interaction.

The term "$K_D$" (M) as used herein refers to the dissociation equilibrium constant of a particular antibody-antigen interaction.

The term "$K_A$" ($M^{-1}$) as used herein refers to the association equilibrium constant of a particular antibody-antigen interaction and is obtained by dividing the $k_a$ by the $k_d$.

The terms "treat," "treating," or "treatment" as used herein generally refer to preventing a condition or event, slowing the onset or rate of development of a condition or delaying the occurrence of an event, reducing the risk of developing a condition or experiencing an event, preventing or delaying the development of symptoms associated with a condition or event, reducing or ending symptoms associated with a condition or event, generating a complete or partial regression of a condition, lessening the severity of a condition or event, or some combination thereof.

A "therapeutically effective amount" as used herein refers to an amount effective, at dosages and for periods of time necessary, to achieve a desired therapeutic result. A therapeutically effective amount of an antibody may vary according to factors such as the disease state, age, sex, and weight of the individual, and the ability of the capture agent to elicit a desired response in the individual.

The term "Akt" as used herein refers to any of three isoforms of Akt (Akt1, Akt2, Akt3), a serine/threonine kinase also known in the art as Protein Kinase B. The exemplary Akt triligand capture agent disclosed herein was designed against Akt1. Therefore, in certain embodiments, "Akt" as used herein refers to a polypeptide having the amino acid sequence of Akt1 set forth in SEQ ID NO:1 (FIG. 31) or a portion thereof, such as a kinase domain, an active site, or an epitope.

The term "kinase" as used herein refers to a polypeptide or enzyme whose natural activity is to transfer phosphate groups from high-energy donor molecules such as ATP to specific substrates.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgGI, IgG2, IgG3, IgM and the like. Exemplary fragments include Fab, Fv, Fab', F(ab')$_2$ and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to a capture agent protein catalyzed capture agent or pharmaceutical formulation thereof refers to the agent or formulation retaining structural and functional integrity for a sufficient period of time to be utilized in the methods described herein.

The term "synthetic" as used herein with regard to a protein catalyzed capture agent or capture agent refers to the capture agent has been generated by chemical rather than biological means.

Development of Akt Capture Agents:

Antibodies are currently the default detection agent for use in diagnostic platforms. However, antibodies possess several disadvantages, including high cost, poor stability, and, in many cases, lack of proper characterization and high specificity. The ideal replacement for use in diagnostic assays should be synthetic, stable to a range of thermal and chemical conditions, and display high affinity and specificity for the target of interest.

A high quality monoclonal antibody possesses low-nanomolar affinity and high target specificity. Interestingly, structural and genetic analyses of the antigen recognition surface have shown that the majority of the molecular diversity of the variable loops is contained in a single highly variable loop (CDR-H3) (Xu 2000). In humans, this loop ranges in size from 1-35 residues (15 on average) (Zemlin 2003), can adopt a wide range of structural conformations (Chothia 1989), and is responsible for most of the interactions with the antigen. The other five loops are significantly less diverse and adopt only a handful of conformations. This suggests that a carefully selected "anchor" peptide can dominate the mode and strength of the interaction between a capture agent and its target protein. It also suggests that other peptide components, while providing only modest contributions to the total interaction energy, can supply important scaffolding features and specificity elements.

In situ click chemistry (Manetsch 2004; Mocharla 2004; Whiting 2006) is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The enzyme promotes the click reaction only between those library components that bind to the protein in the right orientation. The resultant inhibitor can exhibit far superior affinity characteristics relative to the initial inhibitor that formed the basis of the two libraries (Jencks 1981; Murray 2002).

Sequential in situ click chemistry extends the in situ click chemistry concept to enable the discovery of multiligand capture agents (see: USSN 20100009896, incorporated herein by reference). This process was used previously to produce a triligand capture agent against the model protein carbonic anhydrase II (CAII) (Agnew 2009). Sequential in situ click chemistry has several advantages. First, structural information about the protein target is replaced by the ability to sample a very large chemical space to identify the ligand components of the capture agent. For example, an initial ligand may be identified by screening the protein against a large (>$10^6$ element) one-bead-one-compound (OBOC) (Lam 1991) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described (Shuker 1996; Erlanson 2000), most require detailed structural information on the target to guide the screening strategy, and most (such as the original in situ click approach), are optimized for low-diversity small molecule libraries.

As disclosed herein, an iterative in situ click chemistry approach was utilized to synthesize a high-specificity branched triligand capture agent that specifically binds Akt. This in situ click chemistry approach utilized two novel screening strategies. First, a pre-inhibited form of Akt was used as a screening target, providing a means for developing an allosteric site inhibitor. Second, the selection process took advantage of the fact that an in situ click screen in which an anchor ligand and protein target are screened against a large OBOC library will selectively generate multiligand products on the hit beads. The efficiency of this process was characterized using a novel quantitative PCR (QPCR) assay to quantitate the amount of on-bead product. This concept was expanded in the form of "product screens," in which the presence of on-bead clicked product is taken to be the signature of a hit bead. As shown herein, such a product screen can be utilized to increase both the affinity and/or selectivity of the final multiligand capture agent.

The triligand Akt capture agents generated by the methods disclosed herein were found to display mid-to-low nanomolar binding affinity, excellent specificity, and low μM level inhibitory potency for Akt. The capture agents also exhibited inhibition kinetics consistent with binding to Akt outside of the active site, the result of incorporating target protein pre-inhibition into the anchor ligand selection process. The capture agents were shown to function as both capture and detection agents in ELISA assays, efficiently immunoprecipitate Akt from cell lysates, and label Akt in fixed cancer line cells.

Based on the results disclosed herein, the present application provides Akt capture agents comprising three Akt binding moieties, as well as methods of using these capture agents to identify, detect, quantify, and separate Akt and to diagnose, classify, and treat various conditions associated with increased Akt expression and/or activity. The present application also provides novel in situ click chemistry methods for generating capture agents that bind outside the active site of a target protein such as a kinase with high affinity and specificity to, as well as methods of assessing the efficiency of multiligand synthesis using a novel QPCR approach.

Akt Capture Agents:

Provided herein in certain embodiments are triligand Akt capture agents comprising three target-binding moieties. The first target-binding moiety is referred to as an anchor ligand, the second is referred to as a secondary ligand, and the third is referred to as a tertiary ligand. The triligand Akt capture agents provided herein inhibit Akt activity via an allosteric interaction with the non-ATP binding site of ATP.

In certain embodiments, a target-binding moiety comprises one or more polypeptides or peptides. In certain of these embodiments, a target-binding moiety comprises one or more peptides comprising D-amino acids, L-amino acids, and/or amino acids substituted with functional groups selected from the group consisting of substituted and unsubstituted alkyl, substituted and unsubstituted azido, substituted and unsubstituted alkynyl, substituted and unsubstituted biotinyl, substituted and unsubstituted azioalkyl, substituted and unsubstituted polyethyleneglycolyl, and substituted and unsubstituted 1,2,3-triazole.

In certain embodiments, the anchor ligand and secondary ligand are linked to one another via a covalent linkage to form a capture agent biligand. In certain of these embodiments, the anchor ligand and secondary ligand are linked to one another via an amide bond or a 1,4-disubstituted-1,2,3-triazole linkage as shown below:

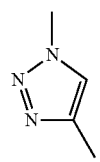

1,4-disubstituted-1,2,3-triazole linkage.

In those embodiments where the anchor and secondary ligands are linked to one another via a 1,4-disubstituted-1,2,3-triazole linkage, the 1,4-disubstituted-1,2,3-triazole linkage may be formed by Cu-Catalyzed Azide/Alkyne Cycloaddition (CuAAC).

In certain embodiments, the anchor and secondary ligands are linked to one another by a Tz4 linkage having the following structure:

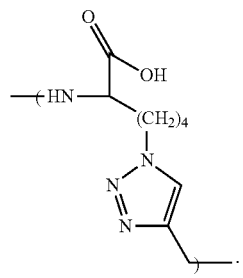

In certain embodiments, the capture agent comprises an 8 carbon linker between the anchor ligand and the triazole. Similarly, in certain embodiments, the capture agent comprises an 8 carbon linker between the tertiary ligand and triazole.

In certain embodiments, the tertiary ligand is linked to the capture agent biligand by a covalent linkage, preferably via the secondary ligand in the biligand. In certain of these embodiments, the tertiary ligand and the biligand are linked to one another by a Tz4 linkage.

In those embodiments wherein one or more of the anchor, secondary, and tertiary ligands are linked to one another via amide bonds, the amide bond may be formed by coupling a carboxylic acid group and an amine group in the presence of a coupling agent (e.g., O-(7-azabenzotriazol-1-yl)-N,N,N',N'-tetramethyluronium hexafluorophosphate (HATU), N-hydroxy-7-aza-benzotriazole (HOAt), or diisopropylethylamine (DIEA) in DMF).

In certain embodiments, the capture agents provided herein comprise the anchor ligand Az8-VFYRLGY-CONH$_2$ (SEQ ID NO: 17).

In certain embodiments, the capture agents provided herein comprise the secondary ligand Pra-FWFLRG-CONH$_2$ (SEQ ID NO: 18).

In certain embodiments, the capture agents provided herein comprise the tertiary ligand Ac-C8-RHERI-CONH$_2$ (SEQ ID NO: 19).

Figure 15:
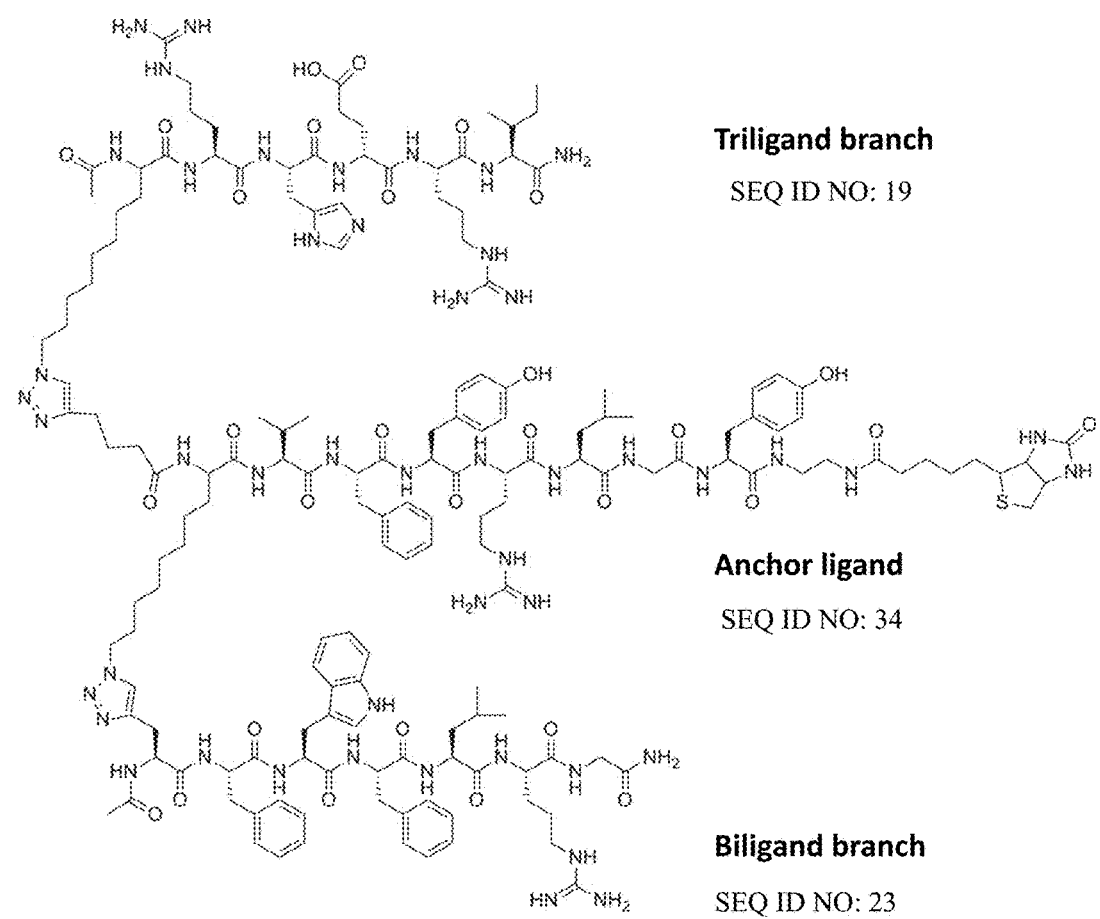
FIG. 15: Structure of the Akt triligand.

In certain embodiments, the capture agents provided herein have the structure set forth in FIG. 15.

In certain embodiments, the Akt capture agents provided herein bind to Akt outside the active site of the protein, i.e., to a non-ATP and non-peptide substrate binding site.

In certain embodiments, the capture agents provided herein are stable across a range of reaction conditions and/or storage times. A capture agent that is "stable" as used herein maintains the ability to specifically bind to a target protein. In certain embodiments, the capture agents provided herein are more stable than an antibody binding to the same target protein under one or more reaction and/or storage conditions. For example, in certain embodiments the capture agents provided herein are more resistant to proteolytic degradation than an antibody binding to the same target protein.

In certain embodiments, the capture agents provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than an antibody binding to the same target protein.

In certain embodiments, the capture agents provided herein are stable at temperatures ranging from about −80° to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C. In certain embodiments, the capture agents provided herein are stable across a wider range of temperatures than an antibody binding to the same target protein, and/or remain stable at a specific temperature for a longer time period than an antibody binding to the same target protein.

In certain embodiments, the capture agents provided herein are stable at a pH range from about 3.0 to about 8.0. In certain embodiments, the range is about 4.0 to about 7.0. In certain embodiments, the range is about 7.0 to about 8.0.

In certain embodiments, the capture agents provided herein are stable in human serum for more than 12 hours. In certain of these embodiments, the capture agents are stable in human serum for more than 18 hours, more than 24 hours, more than 36 hours, or more than 48 hours. In certain embodiments, the capture agents provided herein are stable for a longer period of time in human serum than an antibody binding to the same target protein.

In certain embodiments, the capture agents provided herein may comprise one or more detection labels, including for example biotin, copper-1,4,7,10-tetraazacyclododecane-1,4,7,10-tetraacetic acid (copper-DOTA), $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C, $^{76}$Br, $^{123}$I, $^{131}$I, $^{67}$Ga, $^{111}$In and $^{99m}$Tc, or other radiolabeled products that may include gamma emitters, proton emitters, positron emitters, tritium, or covered tags detectable by other methods (i.e., gadolinium) among others. In certain embodiments, the capture agents may be modified to be used as imaging agents. The imaging agents may be used as diagnostic agents.

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Provided herein in certain embodiments are pharmaceutical formulations comprising one or more of the capture agents provided herein. In certain embodiments, these pharmaceutical formulations comprise one or more pharmaceutically acceptable carriers, excipients, or diluents. These carriers, excipients, or diluents may be selected based on the intended use and/or route of administration of the formulation.

Provided herein in certain embodiments are kits comprising one or more of the capture agents disclosed herein. In certain embodiments, these kits may be used for identifying, detecting, quantifying, and/or separating Akt, and in certain of these embodiments the kits may be used in the diagnosis and/or staging of a cancer associated with increased Akt expression and/or activity. In certain embodiments, a kit as provided herein comprises: (a) a substrate comprising an adsorbent thereon, wherein the adsorbent is suitable for binding Akt, and (b) a washing solution or instructions for making a washing solution, wherein the combination of the adsorbent and the washing solution allows detection of Akt. In other embodiments, the kits provided herein may be used in the treatment of a condition associated with increased Akt expression and/or activity.

In certain embodiments, the kits provided herein may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit as provided herein comprises (a) one or more Akt capture agents that specifically bind Akt; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of Akt detected in a sample is an amount consistent with a diagnosis of a particular condition.

Methods of Using Akt Capture Agents:

Provided herein in certain embodiments are methods of using the Akt capture agents disclosed herein to identify, detect, quantify, and/or separate Akt in a biological sample. In certain embodiments, these methods utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, serum, plasma, urine, sputum, saliva, stool, spinal fluid, cerebral spinal fluid, lymph fluid, skin secretions, respiratory secretions, intestinal secretions, genitourinary tract secretions, tears, and milk.

Provided herein in certain embodiments are methods of using the Akt capture agents disclosed herein to diagnose and/or classify (e.g., stage) a condition associated with increased Akt expression and/or activity, including for example various cancers. In certain of these embodiments, the methods comprise (a) obtaining a biological sample from a subject; (b) measuring the presence or absence of Akt in the sample with the Akt capture agent; (c) comparing the levels of Akt to a predetermined control range for Akt; and (d) diagnosing a condition associated with increased Akt expression based on the difference between Akt levels in the biological sample and the predetermined control.

Provided herein in certain embodiments are methods of treating a condition associated with increased Akt expression and/or activity in a subject in need thereof by administering a therapeutically effective amount of one or more of the capture agents or pharmaceutical formulations disclosed herein. In certain of these embodiments, the capture agent(s) may be linked to one or more additional therapeutic agents, including for example a chemotherapeutic agent. In preferred embodiments, the capture agent is administered as a pharmaceutical composition.

A capture agent or pharmaceutical formulation may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

A capture agent or pharmaceutical formulation may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which is herein incorporated by reference.

Provided herein in certain embodiments is the use of the capture agents disclosed herein in the preparation of a medicament for treating a condition associated with increased Akt expression and/or activity.

Methods of Making/Screening Capture Agents:

Provided herein in certain embodiments are methods of screening target-binding moieties and/or making capture agents that comprise these target-binding moieties. In certain of these embodiments, the resultant capture agent is a kinase capture agent, and in certain of these embodiments the kinase capture agent is an Akt capture agent.

The capture agent production methods disclosed herein begin with identification of a short-chain anchor peptide, then proceed by adding additional covalently coupled peptide branches via a process that is promoted by the target protein. The specificity and inhibitory potency of the final multiligand capture agent are augmented by the peripheral peptide branches. The production methods utilize a pre-inhibited form of the target protein for at least one of the screening steps, resulting in the production of a capture agent that functions as an allosteric site inhibitor.

In certain embodiments, the methods provided herein comprise the following steps:
(a) identifying an anchor ligand by the following steps:
  (i) contacting the target protein with one or more target protein inhibitors;
  (ii) preparing a first plurality of candidate peptides to select an anchor ligand for the target protein;
  (iii) contacting the target protein with the first plurality of candidate peptides;
  (iv) selecting a candidate peptide with affinity for the target protein as the anchor ligand, wherein the candidate peptide binds to the target protein outside of an active site; and
  (v) sequencing the anchor ligand;
(b) identifying a secondary ligand by the following steps:
  (i) preparing an anchor ligand selection block comprising the anchor ligand and an azido group or an alkynyl group;
  (ii) preparing a second plurality of candidate peptides to select a secondary ligand for the target protein, the second plurality of peptides comprising an azido group or an alkynyl group if the anchor ligand selection block comprises an alkynyl group and azido group respectively;
  (iii) contacting the anchor ligand selection block and the second plurality of peptides with the target protein;
  (iv) providing a capture agent biligand by forming a disubstituted 1,2,3-triazole linkage between the anchor ligand selection block and the secondary ligand wherein the azido and alkynyl group of the anchor ligand selection block and the secondary ligand are brought in close proximity by binding to the target protein;
  (v) selecting the capture agent biligand that has an affinity with the target protein; and
  (vi) sequencing the secondary ligand;
(c) identifying a tertiary ligand and, optionally, additional ligands by the following steps:
  (i) preparing a biligand selection block comprising an azido group or an alkynyl group; and
  (ii) repeating steps (b)(ii) to (b)(vi) using a third plurality, fourth plurality, etc., of candidate peptides until a capture agent having desired binding affinity to the target protein is obtained.

In certain embodiments, one or more of the above steps may be omitted. For example, in certain embodiments a known anchor ligand is used. In these embodiments, step (a) is omitted, and the known anchor ligand is used to identify the secondary ligand in step (b). In those embodiments where the target protein is Akt, the anchor ligand may be Az8-VFYRLGY-CONH$_2$ (SEQ ID NO: 17). In certain embodiments, this anchor ligand may be modified with a C-terminal biotin prior to step (b).

In certain embodiments, steps (b)(ii) to (b)(vi) are repeated one time, resulting in production of a capture agent triligand.

In certain embodiments, the first, second, and any additional pluralities of candidate peptides comprise a "one bead one compound" (OBOC) peptide library, wherein the peptides comprise 5 to 7 D-amino acid residues and coupled with a D-propargylglycine at the N-terminus. In certain embodiments, the pluralities of candidate peptides may be different. In other embodiments, one or more of the pluralities may contain the same peptide pool.

The protocol outlined above utilizes one or more target protein inhibitors in the anchor ligand selection step. In certain embodiments, the target protein inhibitor is an ATP-competitive small molecule. Where the target protein is a kinase, the target protein inhibitor may be a small molecule kinase inhibitor. In those embodiments where the target protein is Akt, the target protein inhibitor may be Ac7. Contacting the target protein with one or more target protein inhibitors blocks catalytic residues on the target protein. This prevents formation of the active site, thus removing it as a thermodynamic sink for peptide binding and enabling the candidate peptides to access novel inhibitory sites on an inactive state of the target. Although the anchor ligand can have low affinity for the target, the nature of how it binds to the target is likely the factor that most influences the rest of the multiligand development process. As set forth in the experimental results below, pre-inhibition was utilized in the development of a novel Akt capture agent, and the resultant capture agents were found to stabilize the kinase against activation. Given the structural conservation of ATP-binding pockets across kinases, and hence the often observed poor selectively of inhibitors targeted to such sites, the approach provided herein for developing off-site inhibitors provides several unique advantages.

In certain embodiments, the methods provided herein utilize a known anchor ligand. In certain of these embodiments, the anchor ligand is Az8-VFYRLGY-CONH$_2$ (SEQ ID NO: 17).

In certain embodiments, the anchor ligand used for the screening process may be modified with a biotin. For example, the anchor ligand used for the screening process may be Az8-VFYRLGY-Biotin (SEQ ID NO: 24), wherein "Biotin" is a C-terminal label. In these embodiments, the screening/preparation process comprises the following steps:
  a) contacting Akt with Az8-VFYRLGY-Biotin (SEQ ID NO: 24) ("azide-modified Akt capture agent anchor ligand selection block (I)") to provide an Akt-anchor complex;
  b) contacting the Akt-anchor complex with a first plurality of candidate peptides to select a secondary ligand, the peptides coupled with an L-propargylglycine at its N-terminus;
  c) providing an Akt capture agent biligand by forming a disubstituted-1,2,3-triazole linkage between the anchor ligand selection block and the secondary ligand, wherein the azido and alkynyl group of the anchor ligand selection block and the secondary ligand are brought in close proximity by binding to the target protein to provide a bead modified with the Akt capture agent biligand;
  d) selecting the beads modified with the Akt capture agent biligand;
  e) removing the Akt capture agent biligands from the beads modified with the Akt capture agent biligand;
  f) sequencing the Akt capture agent secondary ligand of the Akt capture agent biligand;
  g) preparing the Akt capture agent biligand with a C-terminal biotin and a 5-hexynoic acid cap ("azide-modified capture agent biligand selection block (I)"); and
  h) repeating the above steps until an Akt capture agent having the desired properties is identified.

In certain embodiments, methods are provided for synthesizing a capture agent as provided herein. In certain embodiments, these methods comprise:
  a) preparing a synthesis block of a target-binding moiety, the synthesis block comprising the target-binding moiety and at least one reactive group that can form a desired linkage with another synthesis block, wherein:
    i) the linkage is selected from the group consisting of amide linkage, 1,4-disubstituted 1,2,3-triazole linkage, and 1,5-disubstituted 1,2,3-triazole linkage; and
    ii) all other active functional groups of the target-binding moiety are protected to avoid undesired reactions; and
  b) coupling the synthesis blocks of the target-binding moieties to provide the capture agent.

Methods of Assessing In Situ Click Efficiency:

QPCR is a technique based on PCR that is used to simultaneously amplify and quantify a target DNA molecule. QPCR allows for detection and quantification of one or more specific sequences in a DNA sample. DNA amplification is measured in real time at each cycle of the PCR reaction. Product detection can be accomplished using non-specific fluorescent dyes that intercalate into double-stranded DNA or sequence-specific DNA probes consisting of oligonucleotides labeled with a fluorescent reporter that permit detection only after hybridization of the probe to its complementary DNA target. When the DNA is in the log linear phase of amplification, the amount of fluorescence increases above the background. The point at which fluorescence becomes measurable is the cycle threshold ($C_t$). The quantity of amplified DNA can be either an absolute number of copies or a relative amount when normalized to DNA input or additional normalizing genes.

As set forth in the examples below, a novel QPCR assay was used to assess the efficiency and selectivity of the in situ click reaction between the anchor ligand and the secondary ligand of the Akt capture agents. Based on these results, methods are provided herein for assessing in situ click reaction efficiency and selectivity. Since the signal-to-noise ratio of the in situ screen (true hit/false positive) depends on the relative rates of the target-mediated and background reactions, QPCR-guided optimization of screening conditions may significantly increase robustness of the sequential in situ click approach.

Provided herein in certain embodiments are methods of assessing in situ click efficiency and/or selectively of a first and second ligand using a QPCR assay. In certain embodiments, the first ligand is an anchor ligand, and the second ligand is a secondary ligand. In other embodiments, the first ligand is a biligand, and the second ligand is a tertiary ligand. The first ligand is a soluble biotinylated ligand, and the second ligand an on-bead ligand. The in situ click reaction is carried out, resulting in the formation of a ligand complex between the first and second ligand. Non-complexed first ligand is removed, and the ligand complex is contacted with a streptavidin (SA)-oligonucleotide QPCR template. This template binds to the biotinylated first ligand in the complex, resulting in selection of beads containing the ligand complex. The selected beads are subjected to QPCR and cycle threshold determination. In certain embodiments, a standard curve is generated to calculate the amount of ligand complex present on the bead for each reaction condition. In certain embodiments, these methods may be used to evaluate variations in click reaction conditions.

Methods for Targeting Specific Epitopes

Large biomolecules, such as proteins, can be characterized by a diverse landscape of chemical properties that vary significantly across different parts of the molecule. Specific regions of a biomolecule surface are referred to as epitopes. It is often desirable to develop molecules that bind specifically to one epitope on a protein, but not to other epitopes on that protein, or to other proteins. Monoclonal antibodies, which are biological products, are developed to bind to specific epitopes on specific proteins. However, there is not a good way, using chemical synthesis approaches, to target a particular epitope on a protein, unless that epitope also happens to fit very special criteria—i.e. the epitope contains a small molecule binding pocket, and so provides a unique energy well for attracting small molecule binders, relative to the rest of the protein. The vast majority of protein epitopes do not fit these special criteria. This invention describes an approach that can guide the development of highly specific molecular binders to general classes of protein epitopes.

An approach for synthesizing molecules that bind to specific parts (epitopes) of large protein biomolecules is described and demonstrated. The invention includes first preparing a peptide or polypeptide fragment of a specific protein. That polypeptide can be site-specifically modified near the region of the epitope of interest, by either substituting one of the naturally occurring amino acids for an artificial amino acid, or the polypeptide fragment is modified after synthesis by chemically altering a specific amino acid. In both cases, the modification results in the presentation of either an acetylene or an azide chemical group near the site-specific modification. That azide (acetylene) containing fragment is then incubated with a very large molecular library. This library, while typically chemically diverse, is also characterized by the fact that each element contains an acetylene (or, instead, each element contains an azide) group. The incubation can be done under conditions that the modified polypeptide fragment can provide a catalytic scaffold for promoting the covalent coupling between select library elements and the polypeptide fragment. In this embodiment, it promotes this coupling by catalyzing the formation of a triazole linkage that is the reaction product of the acetylene and azide groups. According to several embodiments, the selectivity of this catalyzed process is very high. This means that only a very small fraction of the elements in the molecular library will be coupled. Those elements are identified through analytical techniques, and then tested for binding to the polypeptide fragment, or to the entire protein biomolecule from which the polypeptide fragment was extracted. This approach provides a route towards identifying molecules that selectively bind to the intended epitope of the protein target. Approaches known in the art may then be utilized to increase the selectivity and the affinity of the identified binders, without sacrificing their epitope selective binding characteristics.

Figure 32:
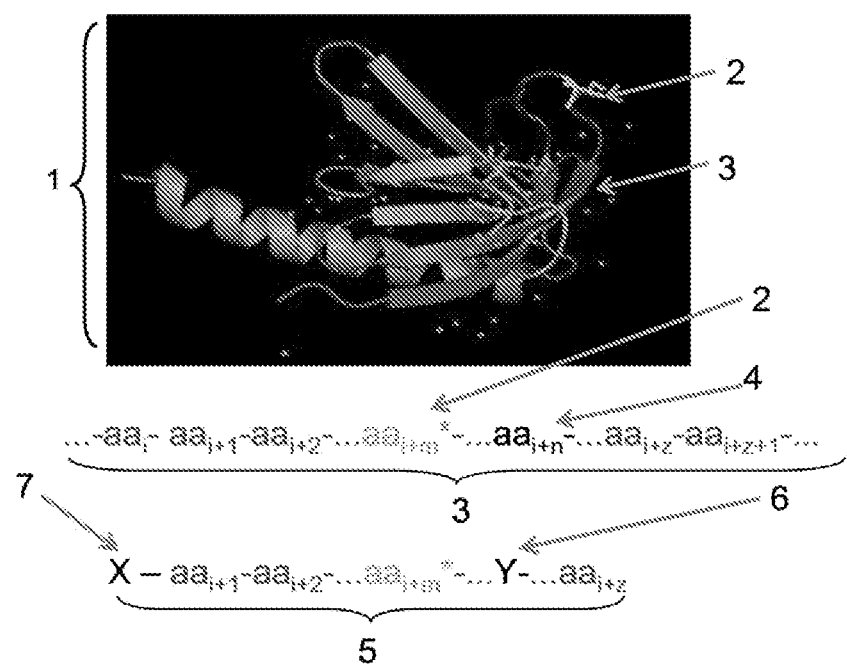
FIG. 32: A schematic providing an illustration of one embodiment of epitope targeting.
Figure 33A:
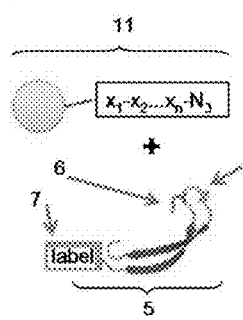
FIGS. 33A-D: A schematic providing an illustration of one embodiment of screening for molecules that bind to the targeted epitope.
Figure 33B:
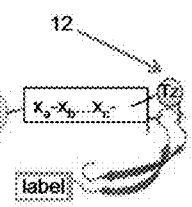
Figure 33C:
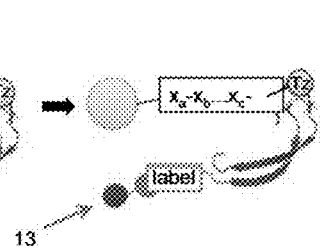
Figure 33D:
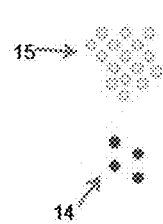

FIG. 32 provides an illustration of one embodiment of the epitope targeting process. A protein target (1) is selected. The protein target (1) has a specific epitope (2) that is of interest for developing capture agent molecule that will bind to that location. That epitope may be a specific amino acid residue (2) associated with a particular peptide or polypeptide fragment (3) of the entire protein (1), or it may be a larger region of the protein (1) containing several amino acids. The epitope is located within a region of the protein that is characterized by a known sequence of amino acids (3). An amino acid near (or within) the epitope (4) is identified for either substitution with an artificial amino acid, or some other specific chemical modification to introduce an azide or acetylene group onto that site. A polypeptide fragment (5) of the protein that contains the targeted epitope is synthesized, but with two modifications. First, (4) is either substituted or chemically modified so as to provide an azide or acetylene group. Second, a site on the polypeptide is modified (7) with a label (a fluorophore or biotin group, for example) for use during the screening steps. There are many ways through which this label can be introduced.

FIG. 33 provides an illustration of one embodiment of screening for molecules that bind to the targeted epitope. Part a of FIG. 33 shows the polypeptide fragment (5) containing the epitope (2), the substituted or altered amino acid (6), and the label (7) being incubated with a large molecular library (11). In this instance, the library is shown presenting an azide group, which would imply that the polypeptide fragment would present an acetylene group at (6). In this instance, the azide group is at the n-terminus of the molecule, but this is not a requirement. In this instance, the molecular library is also represented as a bead-based library, but this is also not a requirement. Part b of FIG. 33 shows that during the incubation step, the polypeptide fragment provides a catalytic scaffold for promoting the covalent coupling of the azide and acetylene groups to form a triazole linkage (12), so that the polypeptide fragment is now covalently bonded to very specific elements of the molecular library. At this point, the molecular library is cleared of all free polypeptide via standard washing steps. Part c of FIG. 33 shows that the label on the polypeptide fragment can be utilized to generate a signal (13) that discriminates those elements of the molecular library that are covalently coupled to the polypeptide fragment, from those library elements that are not. Part d of FIG. 33 shows that the molecular library elements that are covalently coupled to the peptide (14) can be separated from those library elements that are not (15), and subjected to analysis to identify which molecules are potential binders.

Figure 2:
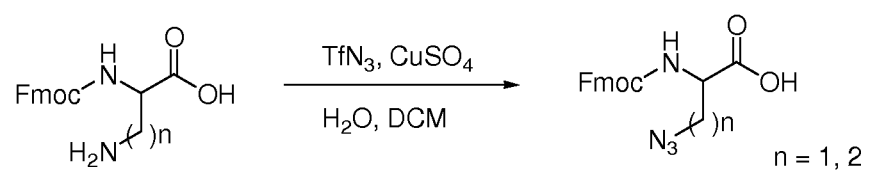
FIG. 2: General synthesis strategy for the azido amino acids Az1 and Az2.

The result of the steps described in FIGS. 32 and 33 is the identification of a small number of molecules that potentially are selective binders to the epitope of interest. These are referred to herein as "hits." Those hits, or a representative set of those hits, can then tested in standard biological assays, such as immunoprecipitation assays, for binding to the protein target of interest. If no binders are identified, then there are several options, which can be tested separately, or in combination. Those options include the following. The process described in FIG. 33 may be repeated, but with a higher concentration of the modified polypeptide fragment (5) present during the incubation step. The process described in FIG. 33 may be repeated, but using a larger (more chemically diverse) molecular library (11). The polypeptide fragment (5) may be modified in a different way in preparation for the screen (FIG. 2), and then the steps of FIG. 33 repeated.

If a molecular library of 1 million molecules, designed to span a broad chemical space, is incubated with a ~50-100 nM concentration solution of the modified polypeptide fragment (5), under standard blocking conditions to prevent non-selective binding, then that screen will generate about 20-100 hit molecules. Of those hit molecules, a small number (1-10) will be molecules that specifically bind to the epitope of interest. Approaches described in the two above-referenced inventions can then be utilized to increase the affinity and specificity of those epitope specific binders.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1: Identification and Preparation of Akt Capture Agents

Three different types of screens were utilized in the development of Akt capture agents: target screens, inhibited target screens, and product screens. In the target screen, hit beads are identified by selecting those beads onto which a target protein binds. The inhibited target screen is similar to the target screen in that hits beads are identified by selecting beads onto which a target protein bound. However, the inhibited target screen is carried out in the presence of a small molecule inhibitor. In the product screen, hit beads were identified by the presence of on-bead product. All three screens utilized OBOC peptide libraries.

Construction of Peptide Libraries:

Randomized peptides were synthesized using standard SPPS protocols either manually or on a Titan 357 automated peptide synthesizer (Aapptec). Libraries were synthesized on TentaGel S (NH$_2$) (Rapp Polymere). Biotinylated peptides were synthesized on Biotin NovaTag Resin (EMD). Side-chain protected peptides were synthesized on Sieber Amide Resin (Anaspec) while C-terminal amide peptides were synthesized on Rink Amide MBHA resin (Anaspec).

The natural Fmoc-L amino acids were purchased from Aapptec and the Fmoc-L-propargylglycine was purchased from (Chem-Impex).

Resins were swelled in NMP and deprotected with 20% piperidine. Four equivalents of Fmoc-amino acid (natural L-amino acids and L-propargylglycine), 3.9 equivalents of HATU, and 12 equivalents of DIEA were added (equivalents relative to loading capacity of the resin). Couplings proceeded for 30-45 minutes. Azido amino acids were added at two equivalents relative to the resin loading capacity. The N-termini were acetylated with 20 equivalents of acetic anhydride and 10 equivalents of DIEA. In cases where use of azido amino acids produced a mixture of two diastereomers, the diastereomers were purified as a single product unless otherwise noted.

Azido Amino Acids:

The structure of the azido amino acids Az1, Az2, Az4, and Az8 are shown in FIG. 1.

Az4 and Az8 synthesis was carried out as described previously (Agnew 2009). The general synthesis strategy for Az1 and Az2 is summarized in FIG. 2.

Az1 was synthesized as described previously (Sun 2007) with modifications. Specifically, triflic anhydride ($Tf_2O$; 3.00 ml, 17.8 mmol) was added dropwise to a vigorously stirred mixture of $NaN_3$ (5.76 g, 88.6 mmol) in 15 mL $H_2O$ and 30 mL DCM at 0° C. The resulting mixture was allowed to warm to ambient temperature and stirred for 2 hours. The water layer was extracted with DCM (2×15 mL) and the combined organic layers were washed with saturated aqueous $Na_2CO_3$ solution (25 mL). Fmoc-Dap-OH (n=1, 2.89 g, 8.86 mmol) dissolved in 80% aqueous acetic acid (26.6 mL) and $CuSO_4 \cdot 5H_2O$ (0.044 g, 0.18 mmol) in 3 mL $H_2O$ was added. The pH of the solution was adjusted to 9-10 with saturated $K_2CO_3$ solution. $TfN_3$ (6 mmol) in DCM (15 mL) was added into a mixture of $H_2O$ (45 mL) and methanol (95 mL), and the pH was readjusted to 9-10 with dropwise addition of saturated $K_2CO_3$ solution. The two-phase system was stirred vigorously for 20 hours. The layers were separated by addition of DCM, the organic layer was washed with water (2×40 mL), and then the combined aqueous phases were acidified with 3 M HCl to pH 2. The aqueous phase was extracted with DCM (4×50 mL) and the combined organic phases were dried over $Na_2SO_4$, filtered, and concentrated in vacuum to give Fmoc-Az1 as a white solid. $^1$H-NMR (400 MHz, DMSO-$d_6$): δ 3.60-3.63 (m, 2H), 4.20-4.27 (m, 2H), 4.30-4.35 (m, 2H), 7.32 (t, 2H, J=7.4 Hz), 7.42 (t, 1H, J=7.4 Hz), 7.73 (d, 2H, J=7.4 Hz), 7.89 (d, 2H, J=7.4 Hz), 7.93 (d, 1H, J=8.0 Hz), 12.64 (s, 1H). $^{13}$C-NMR (100 MHz, DMSO-$d_6$): δ 46.8, 51.0, 54.0, 66.3, 120.5, 125.7, 127.2, 128.5, 140.8, 144.6, 156.4, 171.8.

Az2 was synthesized in the same manner as Az1, except Fmoc-Dab-OH (n=2) was used as starting material. $^1$H-NMR (400 MHz, DMSO-$d_6$): δ 1.80-1.88 (m, 1H), 1.92-2.02 (m, 1H), 3.31-3.38 (m, 1H), 3.41-3.47 (m, 1H), 4.00-4.06 (m, 1H), 4.23 (t, 1H, J=6.8 Hz), 4.28-4.32 (m, 3H), 7.32 (t, 2H, J=7.4 Hz), 7.42 (t, 2H, J=7.4 Hz), 7.64 (d, 1H, J=7.4 Hz), 7.70 (d, 2H, J=7.4 Hz). 12.65 (s, 1H). $^{13}$C-NMR (100 MHz, DMSO-$d_6$): δ 31.1, 47.1, 48.0, 51.6, 66.6, 120.6, 125.7, 127.5, 128.1, 141.2, 144.2, 156.6, 173.8.

Expression and Purification of Akt-S473E-T308P Target Protein:

Screening targets for Akt capture agent development were Akt1-S473E and Akt1-S473E-T308P. Akt1-S473E is a partially active Akt1 kinase domain with an S473E mutation that mimics phosphorylation at the critical S473 residue (Klein 2005). Akt1-S473E-T308P is the fully active kinase phosphorylated at residue T308. These screening targets are readily separated by anion-exchange chromatography, and both showed activity.

The sequence encoding the N-terminal His6 tag through the C-terminal FLAG tag of the pET28a-PKB expression plasmid (His-ΔPH-PKB-EEE-FLAG, Klein 2005) was amplified by PCR. BamH1 and EcoR1 sites were incorporated into the 5' and 3' ends of the amplified fragment using the amplification primers AktpVL-FP (forward, 5'-AAGGAGGGATCCATGGGCAGCAGCCAT-3') (SEQ ID NO: 25) and AktpVL-RP (reverse, 5'-TGGTGTGAAT-TCTTATCACTTGTCATCGTCATC-3') (SEQ ID NO: 26). The amplified fragment was digested with BamH1 and EcoR1, purified by agarose gel electrophoresis, and added to a pVI1393 insect cell expression vector that was previously digested with BamH1 and EcoR1 and dephosphorylated. After transformation and colony screening, successful ligation products were isolated and sequenced using the standard phF and mR sequencing primers. To increase expression, the BamH1 site was oblated and replaced with a Kozak sequence (GCCGCCACCATG) (SEQ ID NO: 27) using QuickChange Mutagenesis (forward primer 5'-ACCGTC-CCACCATCGGGGCCGCCACCATGGGCAGCAGC-CAT-3' (SEQ ID NO: 28), reverse primer 5'-ATGGCTGCT-GCCCATGGTGGCGGCCCCGATGGTGGGACGGT-3') (SEQ ID NO: 29). The final construct, pVLAKT.2, was given to the Caltech Protein Expression Center for construction of the viral expression vector and expression in Hi5 insect cells according to previously described protocols (Kuman 2001; Gao 2005).

The cell pellet was lysed at 4° C. for 15 minutes in MPER lysis buffer (Thermo) and centrifuged at 14,000×g twice to remove cellular debris. The resulting lysate was passed over a 1 mL HisTrap Ni-NTA column and eluted with 10 mL buffer containing 200 mM imidazole. The fractions containing the highest protein concentration were concentrated and desalted using an Amicon Ultracel centrifugal filter device (10000 MWCO, Millipore). The resulting solution was purified by Anion Exchange chromatography as previously described (Klein 2005).

The major product was confirmed to be Akt-S473E by SDS-PAGE and Western blotting with the (2H10) Anti-Akt1 antibody (Cell Signaling Technology). A single band at 45 kDa was observed corresponding to the expected product (predicted MW=45860). Analysis by ESI-MS showed peaks at $[M+H]^+$=45835.0 (minor) and $[M+H]^+$=45992.0 (major) corresponding to unmodified Akt (S473E) (predicted $[M+H]^+_{Monisotopic}$=45832.0) and diphosphorylated Akt (S473E) (predicted $[M+H]^+_{Monisotopic}$=45992.0), respectively. The total yield of AktS473E was approximately 20 mg/mL.

The minor product obtained from anion-exchange chromatography was analyzed by SDS-PAGE and western blotting with the (L32A4) phospho-Akt antibody (Cell Signaling Technology) and found to be phosphorylated at Thr308 (Akt-S473E-T308P).

The activity of Akt-S473E-T308P was characterized by a [$\gamma$-$^{32}$P]-ATP kinase activity assay measuring the incorporation of $^{32}$P into biotinylated crosstide peptide (Anaspec). Briefly, reactions containing 80 ng of Akt-S473E-T308P, 50 μM Bio-crosstide, and varying concentrations of ATP/[$\gamma$-$^{32}$P]-ATP (specific activity=1.5 mCi/mL). The $K_M$ was found to be 120 μM and the $V_{Max}$ was found to be 2×10$^5$ pmol phosphate/min/mg in good agreement with previously determined values for this enzyme (Klein 2005).

Figure 7:
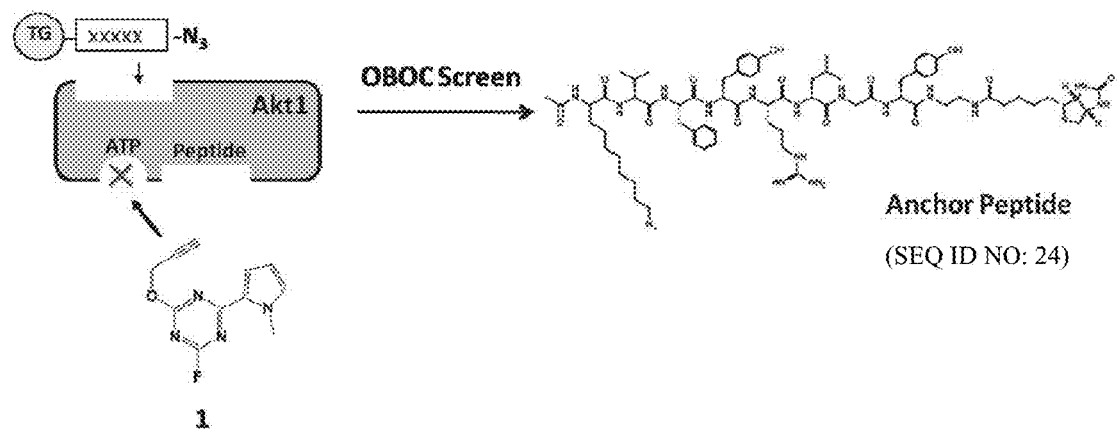
FIG. 7: Anchor peptide selection scheme. The kinase domain of Akt1 (grey) is pre-incubated with the ATP-competitive small molecule inhibitor Ac7 (1). The inhibited kinase is then screened with a comprehensive solid-phase pentamer library with an N-terminal azido-amino acid. The resulting sequences are used to determine the optimal anchor peptide sequence.

Anchor Ligand Selection:

An initial anchor ligand against Akt was identified through the use of a two-part inhibited target screen. The anchor ligand selection process is summarized in FIG. 7.

The OBOC library was synthesized manually, and was of the form NH$_2$-AzX-XXXXX-GYM-TG (SEQ ID NO: 30), where TG is TentaGel resin, X is one of 18 natural L-amino acids (-Cys, -Met), and AzX is one of the three azido amino acids Az2, Az4, and Az8.

Figure 3:
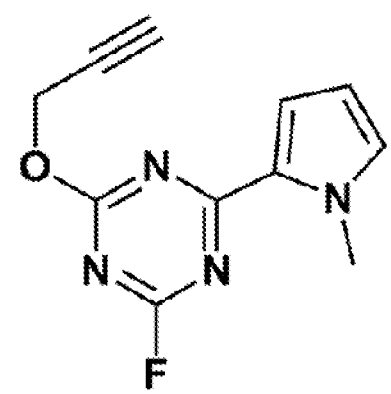
FIG. 3: Structure of Akt inhibitor Ac7. This inhibitor was found to inhibit Akt-5473E-T308P in an ATP-competitive manner with an $IC_{50}$ of 90 µM.

The initial screen was carried out using a naïve peptide library having the form NH$_2$-AzX-XXXXX-GYM-TG (SEQ ID NO: 30), where TG is TentaGel resin, X is one of 18 natural L-amino acids (-Cys, -Met), and AzX is one of the three azido amino acids Az2, Az4, and Az8. The peptide library was deprotected, washed in water, and blocked overnight in Akt Blocking Buffer (25 mM Tris-Cl (pH=7.5), 150 mM NaCl, 10 mM MgCl$_2$, 0.1% (v/v) β-mercaptoethanol, 0.1% (v/v) Tween-20, and 1 mg/mL BSA. For initial screens with the naïve library, 40 mg of pre-blocked library (~1.14×10$^5$ sequences) was incubated with Akt-S473E-T308P at a final concentration of 21 nM in 1 mL Akt Blocking Buffer. Ac7 (FIG. 3) was included at a final concentration of 500 μM. The mixture was incubated for 75 minutes at room temperature, at which point the mixture was washed with Akt blocking buffer and incubated with mouse monoclonal antibodies specific for phosphorylated T308 ([L32A4], Cell Signaling Technology) for 60 minutes at room temperature. The beads were washed and incubated with rabbit anti-mouse secondary antibodies (Promega) conjugated with alkaline phosphatase (AP) for 60 minutes at room temperature. The beads were washed in Akt Blocking Buffer, Akt Wash 1 Buffer (25 mM Tris-Cl, (pH=7.5), 10 mM MgCl$_2$, 750 mM NaCl, 0.1% (v/v) Tween-20), and Akt Wash 2 Buffer (25 mM Tris-Cl (pH=7.5), 10 mM MgCl$_2$, 150 mM NaCl). The beads were developed in Western Blue Alkaline Phosphatase Substrate (Promega). Purple "hit" beads (defined by color change in the presence of 5-bromo-4-chloro-3-indolyl-phosphate/nitro blue tetrazolium (BCIP/NBT) substrate) were washed in water, stripped with 7.5 M Guad-Cl (pH=2), and sequenced by Edman Degradation (FIG. 4).

Figure 5:
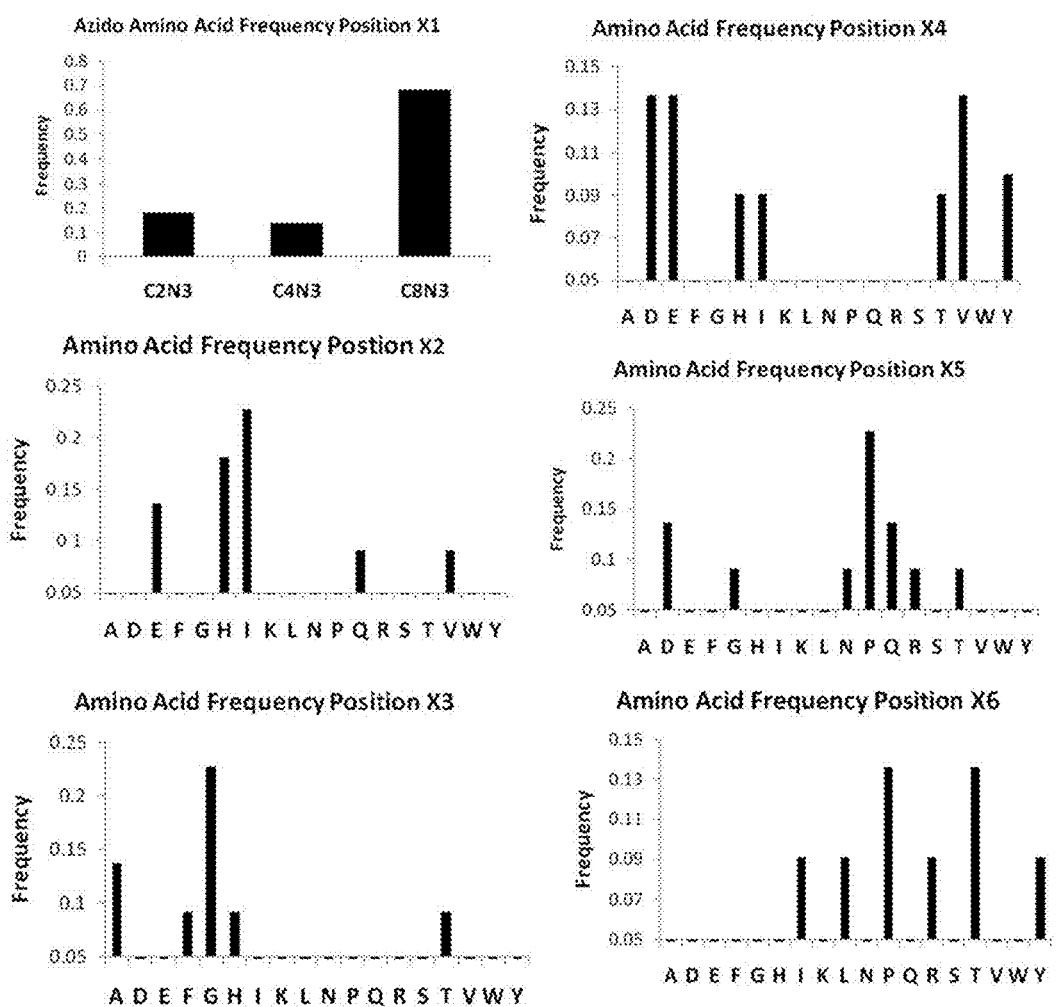
FIG. 5: Frequency of amino acids at each position for 22 selected sequences in the initial anchor peptide screen. The frequency of amino acids at each position was tabulated and used to generate a focused library of the form $NH_2$-Az8-$X_1$-$X_2$-$X_3$-$X_4$-$X_5$-GYM-TG (SEQ ID NO: 20) where $X_1$=H, E, I, Q, V, G; $X_2$=P, F, A, G, H, T; $X_3$=E, D, V, Y; $X_4$=N, G, D, P, Q, R, T; $X_5$=R, L, I, T, G, E, D.

The initial hit sequences defined a focused library which was subjected to an inhibited target screen as described above with 24 mg of focused library in the presence of 500 μM Ac7 and 60 nM Akt-S473E-T308P. The mixture was incubated for 75 minutes in Akt blocking buffer, followed by extensive washing in Akt blocking buffer. The L32A4 antiphospho T308 antibody was added and allowed to bind for one hour at room temperature. After washing, the beads were incubated with anti-rabbit-AP secondary antibody, washing copiously with Akt binding buffer, Akt Wash 1 Buffer, and Akt Wash 2 Buffer, and developed in the presence of BCIP/NBT. The dark purple beads were sequenced as described above (FIGS. 5 and 6).

Figure 12:
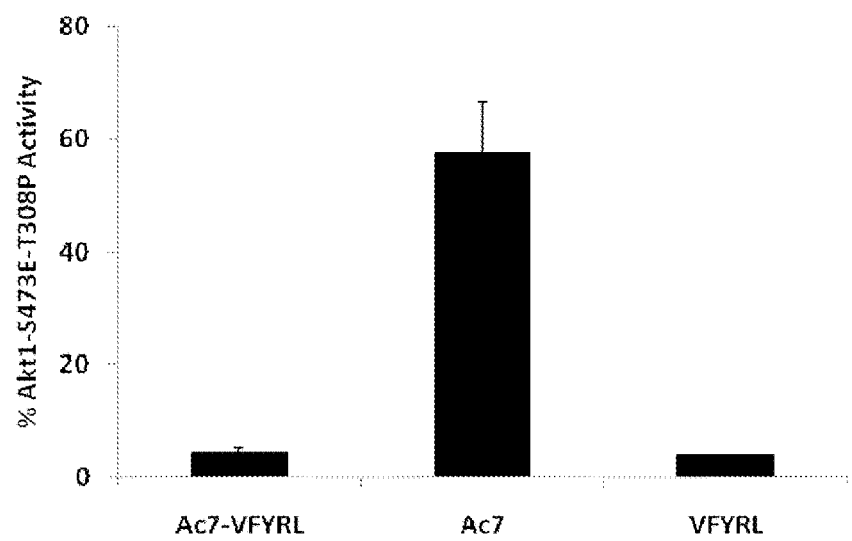
FIG. 12: Inhibition of Akt1-S473E-T308P by Ac7, Anchor Peptide, and Ac7-peptide Conjugate. Kinase reactions were carried out with 120 µM of each compound for 30 minutes at room temperature. The amount of phosphorylated substrate was quantitated by liquid scintillation counting and the % Akt1-S473E-T308P activity determined based on the amount of product formed in the control kinase reaction. The values shown are the mean value of three experiments and the error bars are the standard deviation.
Figure 13:
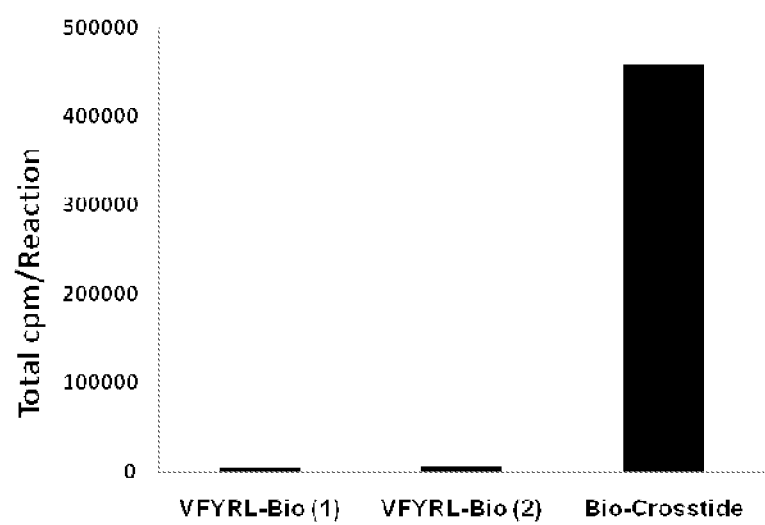
FIG. 13: Anchor peptide is not phosphorylated by Akt1-S473E-T308P. Biotinylated peptides were incubated in a standard kinase reaction mixture for 30 min. at room temperature. A portion of the reaction was spotted onto a SAM2 Biotin Capture Membrane (Promega), washed, and analyzed by liquid scintillation counting. The total counts per minute (cpm) are shown for the anchor peptide (VFYRL (SEQ ID NO: 22)-Bio(1) and VFYRL (SEQ ID NO: 22)-Bio(2)) as well as the standard substrate peptide (Bio-Crosstide). The number in parentheses identifies the diastereomer based on retention time in RP-HPLC.

Candidate sequences were scaled up and tested for their ability to inhibit Akt1-S473E-T308 activity. One of candidate peptide sequences (Az8-VFYRLGY-CONH$_2$) (SEQ ID NO: 17) exhibited almost 95% inhibition of Akt1 in the absence and presence of the conjugated small molecule inhibitor (FIG. 12). This peptide showed little resemblance to any known Akt1 peptide substrate (Jencks 1981) (e.g., RPRAATF) (SEQ ID NO: 31) and was not phosphorylated by Akt in vitro (FIG. 13). This peptide was re-synthesized as a C-terminal biotinylated peptide and used as the anchor in the biligand screen.

Figure 14:
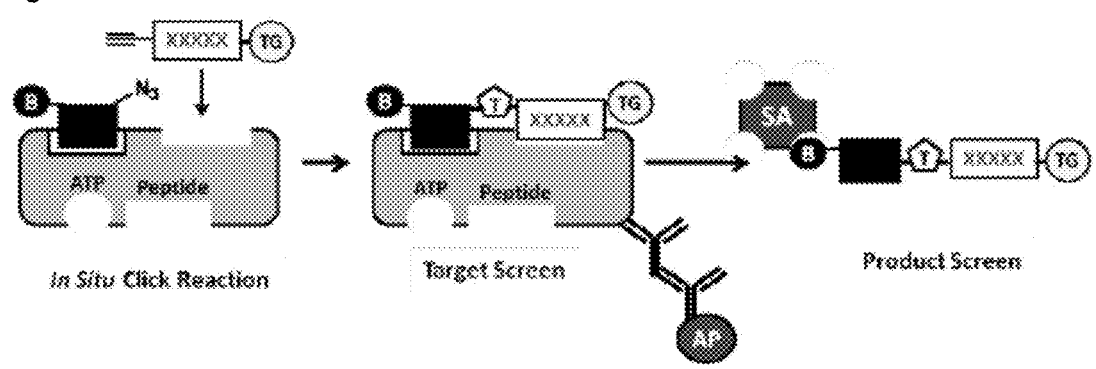
FIG. 14: Strategy for Biligand Screens. A comprehensive pentapeptide library is synthesized on TentaGel (yellow circle) and appended with an acetylene-containing amino acid. This library is incubated with the Akt1 kinase domain (grey) and biotinylated anchor peptide (black). The solid-phase library is probed with an anti-Akt antibody followed by a secondary antibody conjugated to alkaline phosphatase (purple). Hit beads are re-probed with the antibodies alone to eliminate antibody binders. The hit beads are washed, stripped, and re-probed with AlexaFluor647-labelled streptavidin (red) and imaged for fluorescence. The most highly fluorescent beads are sequenced to obtain the biligand candidates. The target screens resulted in hit frequencies between 0.001%-0.01% of the beads in the naïve library while the product screen validated between 23%-37% of these beads for sequencing.

Biligand Branch Selection:

The biligand branch was identified through a two-step screening process. The biligand branch selection process is summarized in FIG. 14.

The initial target screen identified potential hits. For this screen, a naïve library of the form NH2-Pra-XXXXX-GM-TG (SEQ ID NO: 32) where TG is TentaGel resin, X is one of 18 natural L-amino acids (-Cys, -Met), and Pra is propargylglycine, was synthesized by standard split-mix protocols on a Titan 357 automated peptide synthesizer (Aapptec). The anchor ligand was modified with a C-terminal biotin, and the peptide library was incubated with this biotinylated anchor peptide (90 μM) and either Akt-S473E (9 nM) or Akt-S473E-T308P (37 nM) under blocking conditions for 90 minutes or 24 hours at room temperature. Screens using Akt-S473E were probed with 2H10 mAb (CST), and screens using Akt-S473E/T308P were probed with L32A4. Following incubation with alkaline phosphatase-conjugated anti-mouse antibody and development with BCIP/NBT, purple hit beads were stripped overnight, de-colorized in DMF, and re-probed with the primary and secondary antibodies in the absence of target protein. Beads that remained clear were washed and stripped prior to the product screen. The initial target screen resulted in hit frequencies between 0.001%-0.01% of the beads.

Following the target screen, a product screen was carried out to identify true hits. The beads were re-blocked in Akt blocking buffer and incubated with streptavidin-Cy5 (Invitrogen) at a concentration of 0.4 μg/mL for 30 minutes at room temperature. The beads were washed exhaustively with Akt blocking buffer, Akt Wash 1 buffer, and dH2O and imaged on an Axon Genepix 4400A scanner (MDS). The product screen validated between 23-37% of the beads identified in the target screen. Beads displaying saturated fluorescence signal in the product screen were sequenced by Edman degradation (FIG. 8). The resultant sequences showed a preference for aromatic amino acids in the first three positions. Three candidate peptides were selected for further analysis, and the corresponding biligands were synthesized with the 1,4-triazole using the Cu(I)-catalyzed azide-alkyne cycloaddition (Tornoe 2002). Two of the three resultant capture agents showed increased binding to Akt1 in immunoprecipitation experiments. The most promising candidate, which comprised the secondary ligand Pra-FW-FLRG-CONH$_2$ (SEQ ID NO: 18), was scaled up for additional characterization and for development of the triligand.

Triligand Branch Selection:

The triligand branch was identified through a product screen.

Figure 9:
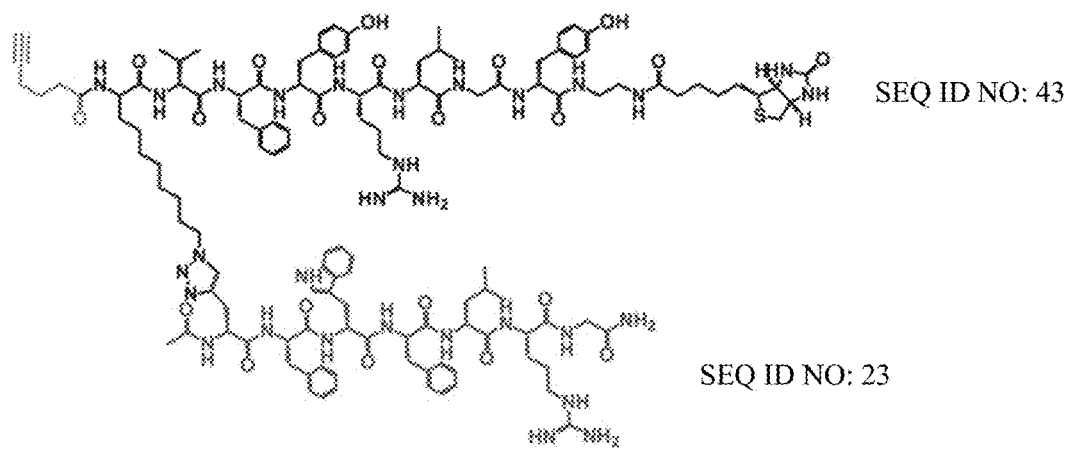
FIG. 9: 5HA-biligand-bio. Structure of biotinylated anchor (biligand) for use in tertiary peptide screen.

Akt biligand was synthesized with a C-terminal biotin and a 5-hexynoic acid at the N-terminus and used as the anchor compound for the tertiary ligand screen (5HA-Biligand-Bio, FIG. 9). The anchor ligand VFYRLGY-Bio (SEQ ID NO: 33) was synthesized according to standard protocols. Following addition of the C$_8$N$_3$ residue, the resin was washed with NMP and set aside (Fmoc-C$_8$N$_3$-VFYRLGY-Biotin) (SEQ ID NO: 34). In parallel, the secondary ligand (Ac-Pra-FWFLRG-CONH$_2$) (SEQ ID NO: 23) was synthesized on Sieber amide resin and cleaved from the resin with side-chain protecting groups intact (see above). The peptide was purified by RP-HPLC using a dH$_2$O:CH$_3$CN gradient with 0.1% TFA. The product was confirmed by MALDI-TOF. The biligand was assembled on-resin according to the following procedure: 30 mg of resin-bound Fmoc-C8N$_3$-VFYRLGY-Biotin (SEQ ID NO: 34) (14 μmol) was washed and added to 47 μmol protected secondary peptide (Ac-Pra-FWFLRG-CONH$_2$) (SEQ ID NO: 23) in the presence of 47 mM Cu(I), 71 mM L-ascorbic acid, and 20% piperidine. The reaction proceeded for 18 hours at room temperature followed by washing in NMP and copper chelation solution. The N-terminal Fmoc group was removed in 20% piperidine. 110 μmol of 5-hexynoic acid (Sigma), 100 μmol of HATU, and 342 μmol DIEA were added in NMP and the reaction was allowed to proceed at room temperature for 2 hr. After washing with NMP, the 5HA-Biligand-Bio was cleaved from the resin in 95:5:5 TFA:dH$_2$O:TES and precipitated in diethyl ether. The product was purified by RP-HPLC as a mixture of diastereomers and analyzed by MALDI-TOF mass spectrometry (Expected [M+H]$^+$= 2450.30, Observed [M+H]$^+$=2449.12).

The initial naïve library was the same as in the initial anchor screen. The naïve library (100 mg) was pre-cleared against SA-AP, developed with BCIP/NBT, and the purple beads removed from the pool. The remaining library was stripped overnight, decolorized with NMP, and blocked again with Akt blocking buffer.

5HA-Biligand-Bio (30 μM) and Akt-S473E (110 nM) were incubated in the presence of the peptide library for 90 minutes at room temperature. The beads were washed as before, probed with SA-AP, and developed in BCIP/NBT, and the purple beads were sequenced by Edman degradation (FIG. 10). Results from the naïve library revealed weak consensus for the tertiary peptide, although Az8 was the preferred amino acid at position 1 and positions 2, 3, and 4 showed a propensity for positively charged amino acids.

A focused library (30 mg) based on the amino acid frequencies in the initial screen was pre-cleared against SA-AP and subjected to a second round of product screening with 5HA-Biligand-Bio (15 μM) and Akt-S473E (21 nM) under blocking conditions. After 60 minutes at room temperature, the beads were washed, stripped with SDS wash buffer (25 mM Tris-Cl (pH=7.5), 2% SDS), washed in dH$_2$O, blocked in Akt blocking buffer, and probed with SA-AP as described above. The beads were developed in the presence of BCIP/NBT and the purple beads sequenced by Edman degradation (FIG. 11). A tertiary ligand consensus sequence was identified with positively charged amino acids at positions 2 and 4, negatively charged amino acids at position 3, and hydrophobic amino acids at position 5. From this pool, the tertiary ligand Ac-C8-RHERI-CONH$_2$ (SEQ ID NO: 19) was selected and conjugated to the biligand to form a branched triligand (FIG. 15).

Example 2: Quantification of In Situ Click Efficiency

Figure 16A:
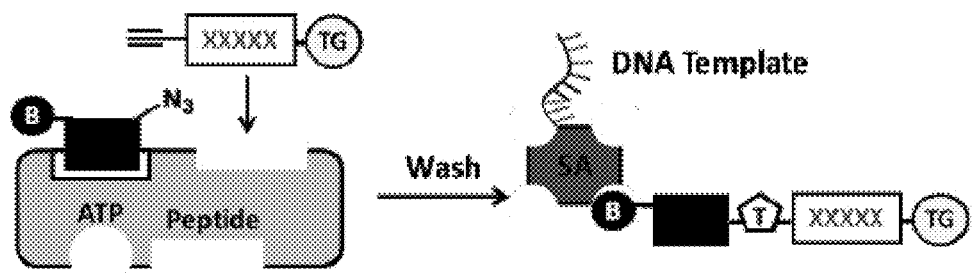
FIGS. 16A-C: Determination of on-bead In situ click reaction efficiency.
Figure 16B:
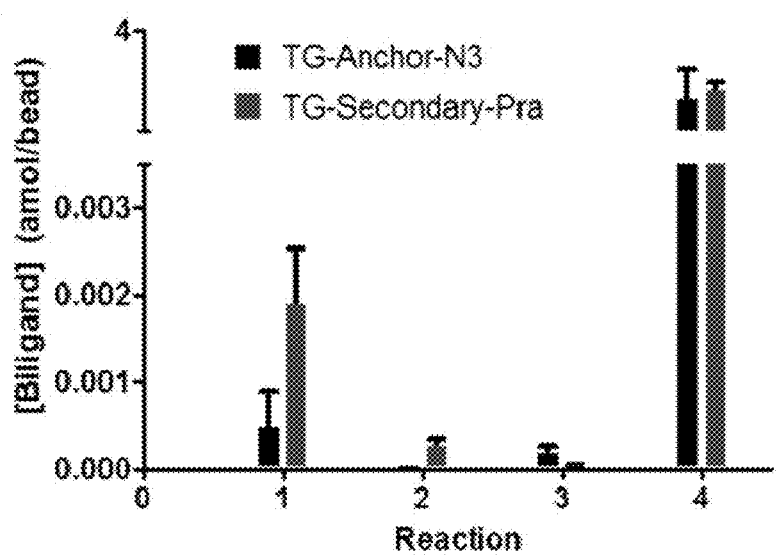
Figure 16C:
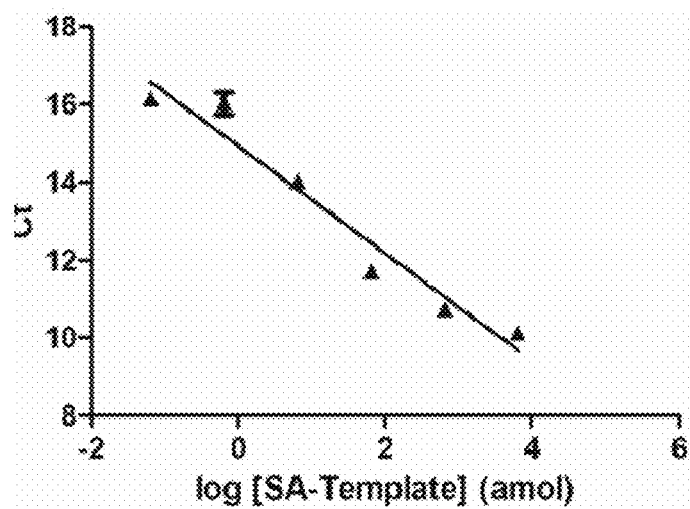

Previous work suggests that the in situ reaction is low-yielding relative to the Cu(I) catalyzed process. Therefore, an analytical assay based on Immuno-PCR (Niemeyer 2005) was developed to assess the efficiency and selectivity of the in situ click reaction between the on-bead secondary ligand and the soluble anchor ligand in Example 1. This novel method takes advantage of the exquisite sensitivity and large dynamic range of QPCR. Briefly, variations of the in situ click reaction between the biotinylated anchor ligand and the resin-bound secondary ligand were carried out, and the biotin label was used to attach a streptavidin (SA)-oligonucleotide (SA-QPCR template) to only those beads that contains biligand product. Five beads were individually picked (to control for variable beads sizes) and added to each QPCR reaction. The cycle threshold ($C_t$) was determined for each reaction condition, and a standard curve was used to calculate the amount of biligand present on the bead for each reaction condition (FIG. 16).

SA-Oligonucleotide Preparation:

Streptavidin expression was performed according to previously published protocols (Sano 1990). Briefly, the streptavidin-cysteine (SAC) gene cloned into the pET-3a plasmid was a generous gift from Dr. Takeshi Sano (Harvard Medical School). Transformed BL21(DE3)-pLysE cells were grown at 37° C. with shaking in LB medium and selection antibiotics ampicillin and chloramphenicol. The cells were induced at OD600=0.6 with IPTG and kept spinning for another 4 hours. The culture was then centrifuged at 1600 g for 10 min and lysed with lysis buffer (2 mM EDTA, 30 mM Tris-HCl, 0.1% Triton X-100, pH 8.0). The insoluble inclusion bodies were then separated from the lysate by centrifugation at 39,000 g for 15 min and dissolved in 6 M guanidine-HCl, pH 1.5 to the original culture volume. The SAC lysate was then refolded by dialysis in 0.2 M sodium acetate, 10 mM β-mercaptoethanol β-ME) pH 6.0 overnight before dialyzed against 50 mM Sodium bicarbonate, 500 mM NaCl, 10 mM β-ME pH 11 in preparation for column purification. Refolded volumes of SAC were mixed 1:1 with binding buffer (50 mM Sodium bicarbonate, 500 mM NaCl, 10 mM β-ME, pH 11). A gravity column packed with 1.5 ml of iminobiotin agarose resin (Pierce) was washed with 10 ml of binding buffer. The refolded mixture was then applied to the column and the eluted fractions were collected and reapplied to the column again, to maximize SAC recovery. After washing the column with 20 ml binding buffer, SAC was eluted with pH 4 elution buffer (50 mM Sodium acetate, 10 mM β-ME). Fractions containing SAC, as monitored by OD$_{280}$, were collected, buffer exchanged to PBS containing 10 mM β-ME, and concentrated to 1 mg/ml final concentration using 10K MWCO filters (Millipore).

Prior to use, stock SAC (streptavidin-cysteine) was buffer exchanged to Tris buffered Saline (TBS) containing 5 mM Tris(2-carboxyethyl) phosphine hydrochloride (TCEP) using desalting columns (Pierce). MHPH (3-N-Maleimido-6-hydraziniumpyridine hydrochloride, Solulink) in DMF was added to SAC at a molar excess of 300:1. In parallel, SFB in DMF (succinimidyl 4-formylbenzoate, Solulink) was added in a 40:1 molar excess to the 5' aminated oligonucleotide (5'-NH$_2$—(CH$_2$)$_6$-GGGACAATTACTATT-TACAATTACAATGCTCACGTGGTACGAGT-TCGTCTCCCAGG-3') (SEQ ID NO: 35). The mixtures were allowed to react at room temperature for 3-4 hours. Excess MHPH and SFB were removed and samples were buffer exchanged to citrate buffer (50 mM sodium citrate, 150 mM NaCl, pH 6.0) using zeba desalting spin columns (Pierce). The SFB-labeled oligonucleotide was then combined in a 20:1 molar excess with the derivatized SAC and allowed to react for 2-3 hours at room temperature before transferring to overnight incubation at 4° C. Unreacted oligonucleotides were removed using a Pharmacia Superdex 200 gel filtration column at 0.5 ml/min isocratic flow of PBS. Fractions containing the SA-oligonucleotide conjugates were concentrated using 10K mwco concentration filters (Millipore). The synthesis of SA-oligonucleotide constructs was verified by non-reducing 8% Tris-HCl SDS-PAGE and found to contain 1-2 conjugated oligonucleotides per monomer.

Figure 29:
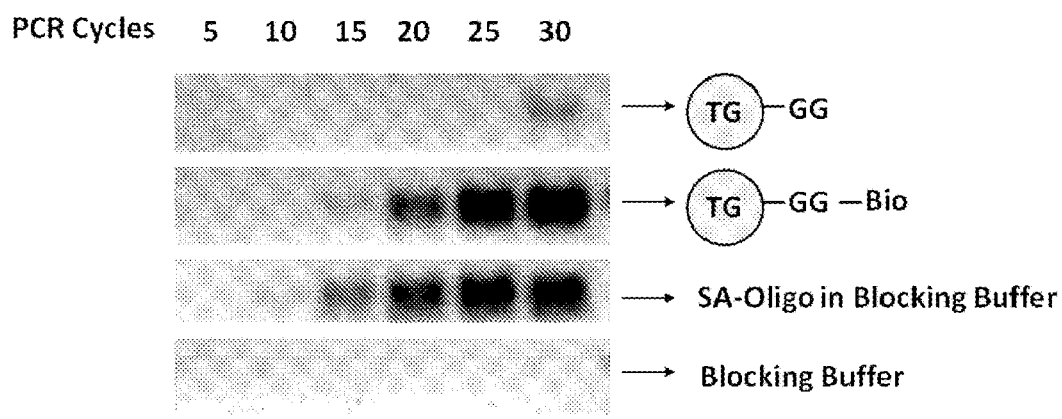
FIG. 29: PCR of single TentaGel beads. PCR was carried out on single beads. Analysis by agarose gel electrophoresis showed a single band at approximately 100 bp.

Prior to QPCR, the SA-oligonucleotide was validated in a conventional PCR reaction with biotinylated TentaGel beads. TentaGel beads were synthesized with either a glycine dipeptide (TG-GG) or a glycine dipeptide with an N-terminal biotin (TG-GG-Bio). The beads were blocked in Akt blocking buffer followed by QPCR Blocking Buffer (0.3% (w/v) BSA, 0.1% (v/v) Tween-20, 150 μg/mL sheared salmon sperm DNA (Ambion) in phosphate buffered saline). After 30 minutes the beads were washed and probed with SA-oligonucleotide (0.17 µg/mL) for 60 minutes at room temperature. After washing in QPCR blocking buffer and PBS, single beads were placed in thin-walled PCR tubes. PCR was carried out with Taq polymerase under standard conditions with Forward Primer (5'-TAATACGACTCAC-TATAGGGACAATTACTATTTACAATTACA-3') (SEQ ID NO: 36) and Reverse Primer (5'-ACCGCTGCCAGAC-CCCGATTTGGCCTGGGAGACGAACTCG-3') (SEQ ID NO: 37), both at 100 nM. A small sample was removed every 5 cycles and analyzed for product formation by agarose gel electrophoresis (4% gel) (FIG. 29).

Ligand Preparation:

The secondary peptide (NH2-Pra-FWFLRG) (SEQ ID NO: 38) and the anchor peptide (Ac-C8N3-VFYRLGY) (SEQ ID NO: 39) were synthesized on TentaGel. 0.45 mg (~1,000 beads) of each were combined with Akt-S473E (22 µM) and the corresponding biotinylated peptide (200 µM), the biotinylated peptide alone (200 µM), or DMSO. The Cu$^+$-catalyzed click reaction contained 0.45 mg immobilized peptide, the biotinylated peptide (200 µM), Cu(I) (9 mM), L-ascorbic acid (30 mM), and Tris[(1-benzyl-1H-1,2,3-triazol-4-yl)methyl]amine (TBTA, 4 mM) in a final volume of 50 µL 4:1 NMP:dH2O. For immobilized secondary peptide, the corresponding soluble biotinylated peptide was Ac-C8N3-VFYRLGY-Biotin (SEQ ID NO: 40). For immobilized anchor peptide, the corresponding soluble biotinylated peptide was Ac-Pra-FWFLRG-Biotin (SEQ ID NO: 41).

After incubating the in situ click reactions at 25° C. for 18 hours with strong agitation, the beads were removed and washed exhaustively in Akt blocking buffer. The Cu$^+$ reactions were washed three times with NMP, ten times in copper chelation solution, three times in NMP, three times in water, and once in Akt blocking buffer. The beads were then stripped in guanidinium-HCl (pH=2), washed in dH2O, and blocked in QPCR Blocking Buffer for 2 hours (0.3% (w/v) BSA, 0.1% (v/v) Tween-20, 150 µg/mL sheared salmon sperm DNA (Ambion) in phosphate buffered saline).

QPCR Assay:

Beads were probed with the SA-oligonucleotide at 0.5 µg/mL for 1 hour at room temperature. The beads were washed five times in QPCR Blocking Buffer and three times in PBS. Three sets of five beads for each reaction condition were placed in PCR tubes and subjected to QPCR on an Applied Biosystems 7300.

For the QPCR, 100 nM of each primer (described above) was added to each reaction along with 1× FastStart Universal SYBER Green Master Mix, ROX (Roche). Each cycle consisted of a denaturation step (94° C. for 30 sec), an annealing step (50° C. for 45 seconds), and an extension step (72° C. for 60 sec). 30 cycles of PCR were carried out and the Ct value for each reaction determined. A titration series of SA-oligo was also carried out in the same experiment (duplicate samples) and used to construct a standard curve. A linear fit of the standard curve was used to relate the observed Ct to the amount of SA-oligonucleotide present in the PCR tube. The following equation was used to obtain the amol SA-oligonucleotide present on each bead from the observed Ct in the QPCR reaction:

$$amol\ SA-Oligo = \frac{10^{\left(\frac{(Ct-14.94)}{-1.378}\right)}}{5}$$

The amount of biligand (amol) of biligand formed on each bead was taken to be the same as the amount of SA-oligo present.

The click reaction between the two peptides was approximately 10-fold more efficient in the presence of Akt1 than in its absence, confirming the requirement for the target protein to catalyze the click reaction. When the anchor ligand was immobilized and the biotinylated secondary ligand was in solution, the efficiency of the in situ click process was reduced by a factor of four (although still above background level), suggesting that the in situ click reaction observed in the screen is dependent on the identity of the on-bead peptide and the manner in which is displayed (i.e., on-bead or in solution). The copper-catalyzed click reaction did not display any orientation dependence, providing further evidence that the click reaction observed in the screening process is highly target-dependent.

Example 3: Role of Linker Length Between Biligand Components

Figure 27:
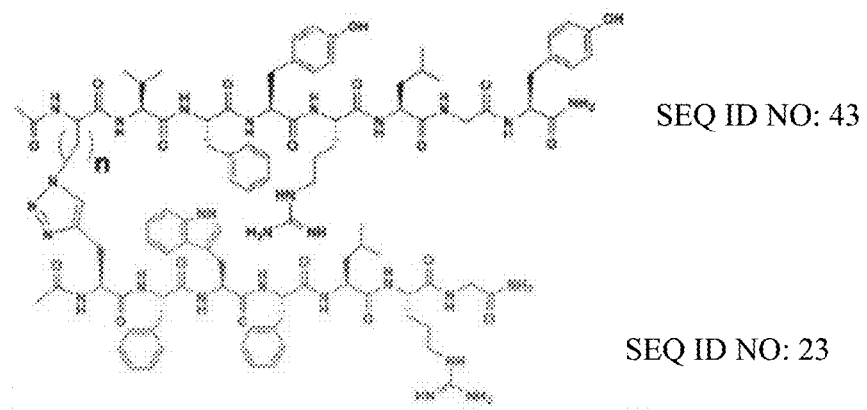
FIG. 27: Biligands were synthesized with 1, 4, and 8 carbon linkers between the anchor peptide and the triazole.

Enzymatic studies were performed to evaluate the role of linker length between biligand components. For this analysis, three biligand variants were synthesized with 1, 4, and 8 carbon linkers between the anchor peptide and the triazole (FIG. 27).

The anchor peptide was synthesized on 150 mg scale on Rink amide MBHA resin and appended with one of three azido amino acids with 1, 4, or 8 methylene units between the Cα carbon and side chain azide (Az1, Az4, and Az8; FIG. 1). Following acylation of the N-terminus with acetic anhydride, the resin was resuspended in NMP. The secondary ligand (Ac-Pra-FWFLRG-CONH$_2$) (SEQ ID NO: 23) was synthesized on 300 mg scale on Sieber amide resin. The peptide was cleaved by adding 4.5 mL 2% TFA in CH$_2$Cl$_2$ and incubating for 5 minutes. The TFA was quenched by filtration into 225 µL DIEA. The cleavage was repeated five times, the filtrates were combined, and the solvent removed by rotary evaporation. The protected secondary peptide was the purified by C18 RP-HPLC with a dH$_2$O:CH$_3$CN (0.1% TFA) gradient.

The biligand variants were synthesized by combining 12 mg of anchor peptide on Rink MBHA resin (~8 µmol azide) with 24 µmol side-chain protected secondary peptide in the presence of 40 mM CuI, 60 mM L-ascorbic acid, and 20% piperidine. The reaction proceeded for 6 hr at room temperature with agitation. The copper was removed by exhaustive washing with copper chelation solution (22 mM sodium dithylthio carbamate (trihydrate), 29 mM DIEA, in DMF) followed by NMP. The biligands were cleaved from the resin in 95:5:5 TFA:H$_2$O:TES, precipitated in diethyl ether, and purified by C18 RP-HPLC with a dH$_2$O:CH$_3$CN (0.1% TFA) gradient. MALDI-TOF MS: Bi—C(N=1): Expected [M+H]$^+$=2031.04, Observed [M+H]$^+$=2029.66. Bi—(N=4): Expected [M+H]$^+$=2073.09, Observed [M+H]$^+$=2070.05. Bi—(N=8): Expected [M+H]$^+$=2129.15, Observed [M+H]$^+$= 2125.73.

Biligand linker length variants were evaluated for their ability to inhibit Akt. 0.5 µL of biligand dilution in DMSO or DMSO alone was added to a 20 µL reaction containing 400 ng Akt-S473E-T308P, 200 ng of GST-GSK-3α/β crosstide fusion protein (Cell Signaling Technology), 500 µM ATP, 25 µM Tris-Cl (pH=7.5), 10 mM MgCl$_2$, 1 mM DTT, 0.01% Triton X-100, 1× Complete protease inhibitors (-EDTA, Roche), 1× PhosStop phosphatase inhibitors (Roche). Reactions proceeded at 30° C. for 30 minutes and were quenched with kinase quenching buffer (500 mM DTT in 20% SDS). 2 µL of each quenched reaction was spotted onto nitrocellulose and the dot blot was blocked with 5% non-fat milk for 1 hour. The blot was probed with rabbit anti-phospho GSK-3 α/β (Ser21/9) mAb (37F11, Cell Signaling Technology) at a 1:1000 dilution overnight at 4° C. The blot was washed and probed with anti-rabbit-HRP secondary antibody at a 1:500 dilution. The blots were developed with Pico West Dura ECL substrate (Thermo) and imaged on film. The image was scanned and each spot was quantitated by densitometry using ImageJ. The total density of was normalized to the density of spots where no inhibitor was added to generate a % pAkt Activity value which was plotted against the log [compound] in Graph Pad Prism. In the case of n=4 and n=8, the plotted activity was the average of the observed activity for the two diastereomers.

Figure 28:
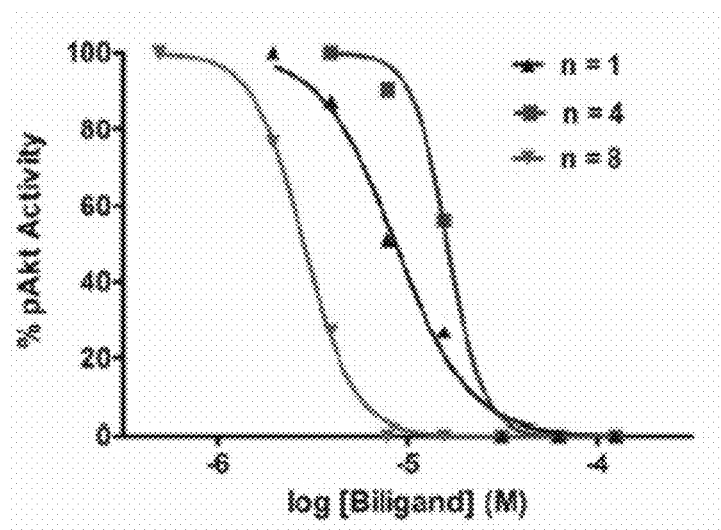
FIG. 28: Biligand linker length variants were titrated against activated Akt-S473E-T308P and activity was measured by immunoblotting and quantitated by densitometry. The n=8 linker clearly yields the biligand with the highest inhibitory potency.

Analysis of the Akt inhibition results indicated a strong preference for the 8 carbon linker that was originally used to develop the biligand (FIG. 28). This suggests that "hit" sequences arising from the biligand screen were determined not only by the target protein and the soluble anchor peptide, but also from the relative spacing between the azide and acetylene functionalities in each component.

Example 4: Characterization of Akt Capture Agents

Binding Affinity:
The affinity of the anchor ligand, biligand, and triligand developed in Example 1 was determined by ELISA with immobilized Akt-S473E.

5HA-Biligand-Bio was assembled and purified as described above. The tertiary ligand (Ac-C8N$_3$-RHERI-CONH$_2$) (SEQ ID NO: 42) was synthesized on Rink Amide MBHA resin as described above. Purification by RP-HPLC gave the desired product (MALDI-TOF: Expected [M+H]$^+$=961.57, Observed [M+H]$^+$=961.43). The triligand was assembled by combining 544 nmol 5HA-Biligand-Bio with 1.09 µmol Ac-C8N$_3$-RHERI-CONH$_2$ (SEQ ID NO: 42) in the presence of 600 nmol TBTA, 10 mM CuI, and 30 mM L-ascorbic acid in 4:1 NMP:dH$_2$O. The reaction proceeded for 18 hours at room temperature with agitation. The desired product was purified by RP-HPLC as a mixture of diastereomers and analyzed by MALDI-TOF MS (Expected [M+H]$^+$=3410.88, Observed [M+H]$^+$=3408.96.

3 µg of Akt-S473E was added to each well in a HisSorb Ni-NTA plate (Qiagen) in 50 µL of ELISA blocking buffer (25 mM Tris-Cl (pH=7.5), 150 mM NaCl, 10 mM MgCl$_2$, 0.1% (v/v) Tween-20, and 4 mg/mL BSA). 50 µL of imidazole blocking buffer (25 mM Tris-Cl (pH=7.5), 150 mM NaCl, 10 mM MgCl$_2$, 0.1% (v/v) Tween-20, 100 mM imidazole, and 4 mg/mL BSA) was added to the control wells. After 18 hours at 4° C., the wells were washed with ELISA blocking buffer and 50 µL of each ligand dilution was added in ELISA blocking buffer. The ligands were bound at 4° C. for 120 minutes followed by three washed in ELISA blocking buffer. 50 µL of horseradish peroxidase-conjugated streptavidin (SA-HRP, Thermo) was added (1:5000 dilution in ELISA blocking buffer) and incubated for 70 minutes at 4° C. The wells were washed three times in TBST (Tris-buffered saline+0.2% Tween-20) and once in TBS (Tris-buffered saline). 50 µL of peroxidase substrate (KPL) was added to generate the final signal which was quenched in 1 M H$_2$SO$_4$ and quantitated on a 96-well plate reader at λ=450 nm. The Net A450 was calculated by subtracting the A450 of each blank well (No Akt-S473E) from the experimental well. The data were fit by non-linear regression in GraphPad Prism.

Figure 19:
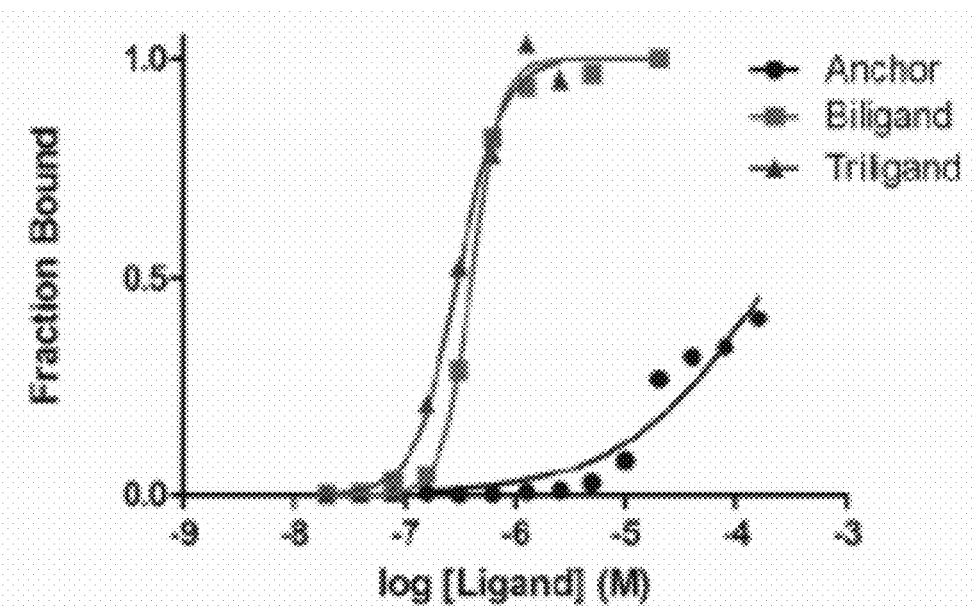
FIG. 19: Relative affinity of Akt triligand and its components. Akt-S473E was immobilized on Ni-NTA plates and incubated with varying concentrations of biotinylated peptide. All values were normalized to the binding observed at saturation.

The binding affinity of the anchor ligand for Akt (>25 µM) made it unsuitable as a stand-alone agent for high-sensitivity capture of Akt. The biligand showed a >100-fold improvement in its affinity for Akt relative to the anchor peptide, while the triligand showed only a modest affinity gain (2-3 fold) (FIG. 19).

Figure 20:
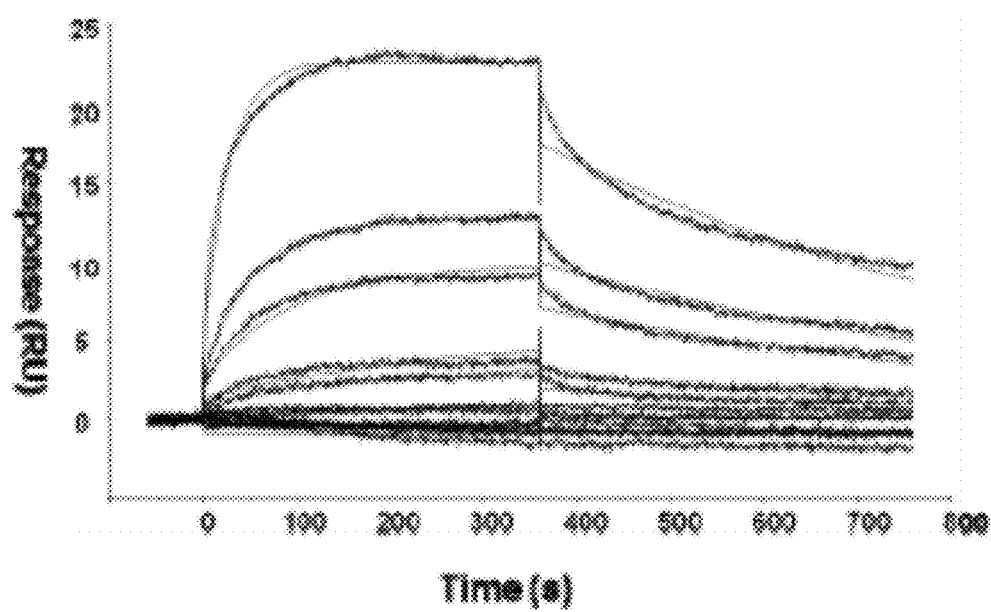
FIG. 20: Absolute affinity of the triligand by surface plasmon resonance. For this experiment, the biotinylated triligand was immobilized on a streptavidin-derivatized biacore chip and probed with Akt-S473E at concentrations ranging from 9 μM to 1 nM. Fits for the sensograms are shown as solid lines and the KD was found to be 200 nM by determination of the kinetic parameters.

Triligand binding affinity was further analyzed by SPR using a Biacore T100. A Streptavidin Chip (Series S, G.E. Healthcare) was conditioned as recommended by the manufacturer. Biotinylated ligand was diluted into HBSP+Buffer (G.E. Healthcare) to a final concentration of 100 nM and 137 RU was immobilized on the chip. Akt1-S473E was prepared as described previously and subjected to buffer exchange into HBSP+ using Zeba Desalting Columns (Pierce). Serial dilutions of the enzyme were made in HBSP+ buffer (9000 nM to 1 nM) and flowed over the chip at 50 µL/minute. Binding and dissociation were carried out at 10° C. with a contact time of 360 seconds, a dissociation time of 400 seconds, and a stabilization time of 200 seconds. The response was corrected using an unmodified reference flow cell. Kinetic constants were obtained from the sensograms and used to calculate the dissociation constant. Analysis confirmed that the triligand has mid- to low-nanomolar affinity for Akt1-S473E ($K_D$=200 nM, FIG. 20).

Binding Specificity:
The specificity of the anchor ligand, biligand, and triligand developed in Example 1 was analyzed using a battery of protein kinases. For these assays, the multiligands were used as immobilized capture agents for Akt1-S473E as well as a set of His-tagged active protein kinase domains from the AGC family (Akt1, PDK1 (R&D Systems), and p70s6 kinase (R&D Systems)), the STE family (MEK1 (Invitrogen)), and the GMGC family (GSK3β (Invitrogen)). β-actin (Abcam) was used as a control. Akt1-S473E was expressed and purified as described above.

The relative affinity of each kinase was determined by probing with an anti-His6 antibody and normalizing the response to Akt1-S473E. All proteins were diluted in Akt blocking buffer to a final concentration of 24 nM prior to use. Ligands were diluted in Akt blocking buffer to a final concentration of 2.5 µM prior to use. 100 µL of each ligand (250 pmol) was added to each well of a HBC streptavidin-coated 96-well plate. The ligands were bound at 4° C. for 1 hour followed by addition of D-biotin to a final concentration of 500 µM. After 10 minutes at 4° C., the wells were washed three times with Akt blocking buffer and blocked overnight in 5% non-fat milk.

The wells were washed three times in Akt blocking buffer and 50 µL of active protein was applied to each well. After binding for 120 minutes at 4° C., the wells were washed three times in Akt blocking buffer to remove unbound protein. 50 µL of horseradish peroxidase-conjugated Anti-His6 antibody was added at a dilution of 1:100 (His Probe (H-3) HRP conjugate, Santa Cruz Biotechnology). The antibody-HRP conjugate was incubated for 60 minutes and the wells were washed 3 times in TBST and once in TBS. 50 µL of peroxidase substrate (KPL) was added and the resulting color change was quenched with 50 µL 1 M H$_2$SO$_4$. The A$_{450}$ measured on a 96-well plate reader. The Net A$_{450}$ was obtained by subtracting the blank value for each protein (No ligand) from each of the triplicate values obtained for the ligand-protein interaction. Each NetA$_{450}$ value was normalized to the NetA$_{450}$ from the Akt-S473E samples to obtain a normalized relative binding value. The mean value for the triplicates was calculated and plotted and the error bars were generated from the standard error of the mean (GraphPad Prism).

Figure 21:
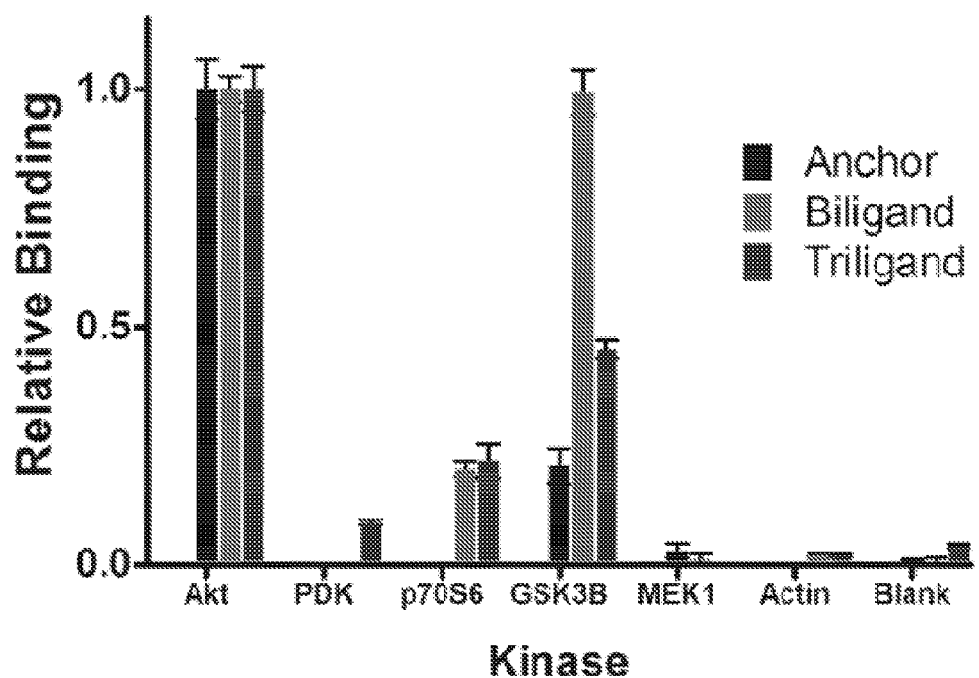
FIG. 21: Specificity of anchor, biligand, and triligand. Biotinylated ligand was immobilized on Streptavidin plates and probed with 25 nM His-tagged kinase followed by anti-Histag antibody-HRP conjugate. Values represent the mean $A_{450}$ obtained from three experiments after normalization to Akt1-S473E binding. The error bars show the standard error. Note that although the affinity of the triligand is only marginally improved over the biligand, the selectivity for Akt1 is clearly enhanced.

Results are set forth in FIG. 21. The anchor ligand was very specific for the Akt1 protein, with only modest binding to GSK3β. The significantly higher affinity biligand showed reduced selectivity, with significant cross-reactivity to GSK3β. For the triligand, however, binding to GSK3β was significantly reduced, bringing it close to the level observed for the anchor peptide. Additionally, the off-target binding to MEK1 is completely eliminated at the triligand stage. These results suggest that the in situ click product screen can be used to increase the selectivity of the capture agent.

Akt Inhibition:

Two standard enzyme kinetic assays were carried out to determine the mode of Akt1 inhibition by the triligand (Segel 1975). For these assays, the kinase activity is measured under varying substrate and triligand concentrations. The resulting data can be interpreted so that the nature of the competition between the triligand and the substrate for the relevant kinase binding site is determined. For example, if the triligand and ATP competed for the same binding pocket, the maximum velocity ($V_{max}$) of the kinase would be unchanged while the Michaelis constant ($K_M$) would increase. The plots can also be used as a means of determining the inhibition constant ($K_i$) of the triligand.

Akt-S473E-T308P was prepared by incubating 75 μg Akt-S473E with 1 μg PDK1 (Sigma) in the presence of 500 μM ATP in 1× reaction buffer (25 mM Tris-Cl (pH=7.5), 10 mM MgCl$_2$, 2 mM DTT, 1× protease inhibitors (Roche), 1× phosphatase inhibitors (Roche)). The phosphorylation reaction proceeded for 40 minutes at room temperature followed by addition of 25 mM EDTA. The quenched reaction was added to 40 μL Anti-FLAG M2 agarose (Sigma) and allowed to bind for 2 hr at 4° C. The resin was washed in FLAG Wash Buffer (20 mM HEPES (pH=7.4), 150 mM NaCl, 1× protease inhibitors (Roche), 1× phosphatase inhibitors (Roche)) and the Akt1-S473E-T308P eluted with FLAG Elution Buffer (FLAG wash buffer+0.15 mg/mL 3×FLAG peptide) for 30 minutes at room temperature. The concentration of protein was determined by Bradford assay.

To determine the inhibition mode of the triligand with respect to the substrate peptide, kinase reactions were set up with increasing concentrations of peptide substrate (Biotin-Crosstide, Anaspec). The peptide substrate ranged in concentration from 375 nM to 25 μM (7 concentrations) and the triligand ranged in concentration from 0-25 μM (0, 200 nM, 1 μM, 5 μM, 25 μM). The concentration of non-radioactive ATP was held constant at 25 μM and [γ-$^{32}$P]-ATP (7000 Ci/mmol, 10 μCi/μL) was added to a final concentration of 83 nM. Akt-S473E-T308P was added to a final concentration of 12 ng/4. Reactions proceeded for 30 minutes at room temperature in 1× reaction buffer (50 mM Tris-Cl (pH=7.5), 10 mM MgCl$_2$, 1 mM DTT, 0.01% Triton-X100, 1× protease inhibitors (Roche), 1× phosphatase inhibitors (Roche)). The reactions were quenched with Guanidinium-HCl to a final concentration of 3.5M.

Product formation was determined by spotting 5 μL of quenched reaction onto SAM2 Biotin Capture Membrane (Promega), the membrane was washed according to the manufacturer's instructions and analyzed by liquid scintillation counting. The observed counts per minute were converted into pmol of product formed based on the activity and concentration of the [γ-$^{32}$P]-ATP assuming a counter efficiency of 50%. The velocity was plotted against [Peptide] at each [Triligand] and analyzed by linear and nonlinear regression in Graph Pad.

To determine the inhibition mode of the triligand with respect to the ATP, kinase reactions were set up with increasing concentrations of ATP. The reactions were set up in a similar manner to that described above. The concentration of Biotin-Crosstide was held constant at 25 μM and the concentration of enzyme was held at 13 ng/4. The concentration of ATP ranged from 125 μM to 4 μM (125 μM, 63 μM, 32 μM, 16 μM, 8 μM, 4 μM) while the concentration of triligand varied from 0 to 10 μM (0, 1 μM, 5 μM, 10 μM). [γ-$^{32}$P]-ATP (7000 Ci/mmol, 10 μCi/μL) was added to the cold ATP stock to maintain an [ATP]$_{total}$/[γ-$^{32}$P]-ATP ratio of 1667. The reactions were incubated, quenched, and analyzed as described above.

Figure 24A:
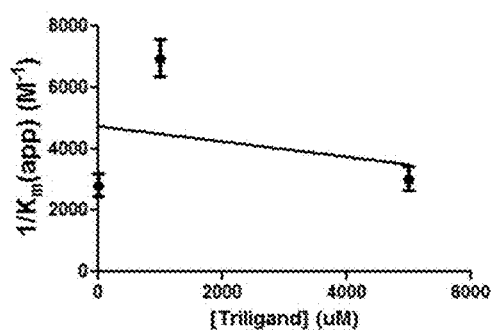
FIGS. 24A-C: Determination of $K_i$ and inhibition mode for triligand with respect to ATP.
Figure 24C:
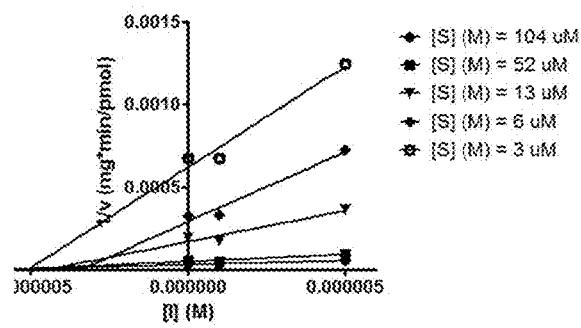
Figure 24B:
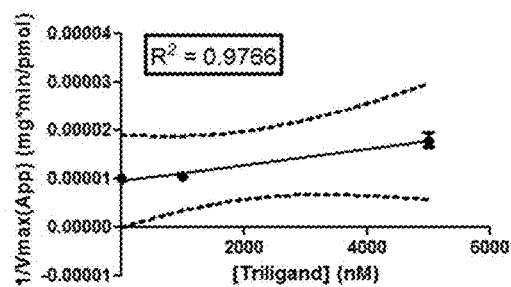

Results of the kinetic assays are summarized in Table 1. $K_M$ and $V_{max}$ values for Akt1-S473ET308P were obtained by nonlinear regression from the results of the inhibition experiments (GraphPad). The literature values for the Michaelis constants for ATP and substrate peptide were taken from Klein 2005. The triligand $K_i$ (noncompetitive inhibition) was obtained from the negative X-intercept of the Dixon plot of 1/v vs. [Triligand] with varying [ATP]. The $K_i$ is the mean value of the observed X-intercepts and the error range is the standard deviation. The triligand $K_{i'}$ (uncompetitive inhibition) was obtained from the intercept of the Dixon plot of 1/v vs. [Triligand] with varying [Peptide]. The $K_{i'}$ is the mean value of the intercepts and the error range is the standard deviation. These plots as well as additional kinetic analyses are set forth in FIGS. 23 and 24.

TABLE 1

|  | V vs. [Peptide], Variable [Triligand] | V vs. [ATP], Variable [Triligand] |
|---|---|---|
| $K_M$ (μM) (present results) | 9 ± 0.7 (Peptide) | 213 ± 25 (ATP) |
| $K_M$ (μM) (literature) | 3.5 (Peptide) | 155 (ATP) |
| $V_{max}$ (pmol/min/mg) | 45764 ± 1486 | 98996 ± 8242 |
| $K_i$ ($K_{i'}$) (μM) | (2.6 ± 0.7) | 4 ± 1 |
| Inhibition mode | Uncompetitive | Noncompetitive |

Figure 22A:
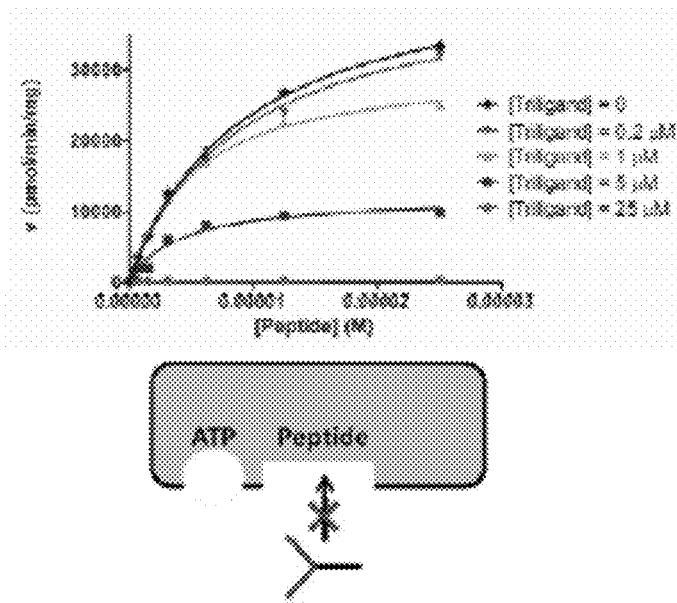
FIGS. 22A-B: Inhibition of Akt1 activity.
Figure 22B:
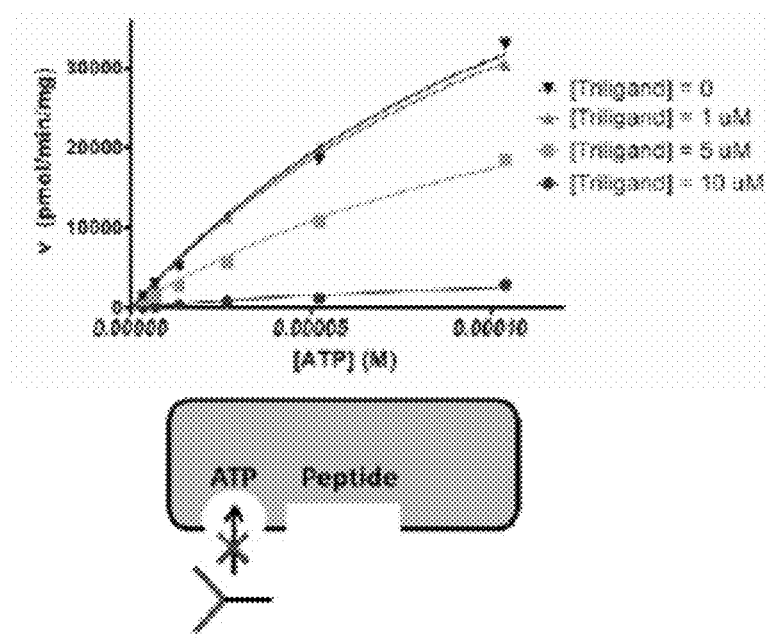
Figure 23A:
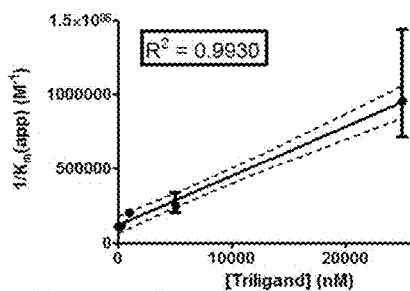
FIGS. 23A-D: Determination of $K_i'$ and inhibition mode for triligand with respect to peptide substrate.
Figure 23C:
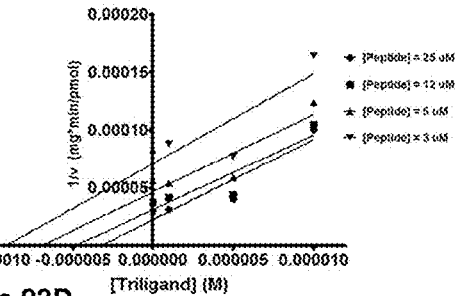
Figure 23B:
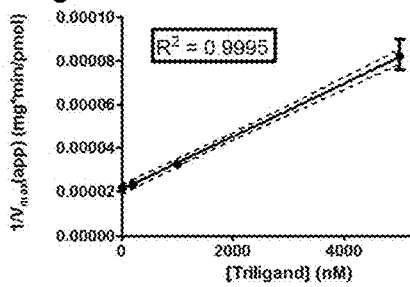
Figure 23D:
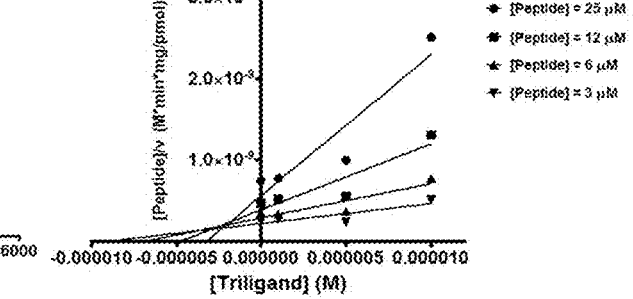

The results show reduction in the enzyme $V_{max}$ for both substrates, as a function of increasing triligand concentration (FIG. 22). This indicates that the triligand does not directly compete with either substrate for binding to their respective active sites (i.e., the triligand binds to a site distinct from the ATP or peptide-substrate binding sites). When ATP is the varied substrate, triligand addition appears to have no effect on $K_M$, consistent with noncompetitive inhibition. When the peptide concentration is varied, $K_M$ decreases in a manner consistent with uncompetitive inhibition. When $K_i$ and $K_{i'}$ are determined from the Dixon plots of 1/v vs. [Triligand] both values are similar (4 μM vs. 2.6 μM respectively).

Figure 30:
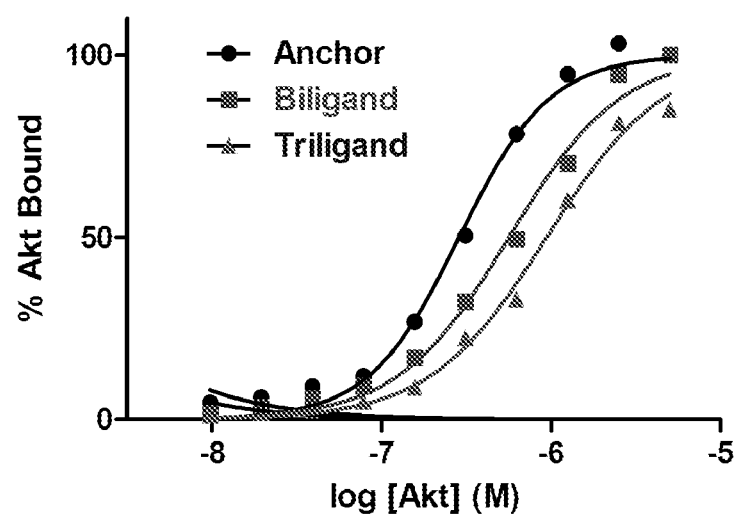
FIG. 30: Antibody inhibition of triligand affinity. Immobilized anchor, biligand, and triligand were probed with varying concentrations of Akt-S73E. Binding was detected by an anti-Akt1 monoclonal antibody ([2H10]) followed by an anti-mouse secondary antibody-HRP conjugate. The fraction bound was normalized and plotted against the concentration of Akt-S473E on a log scale. The data indicates that as the multiligand size increases, the [2H10] antibody binding is reduced, suggesting that the triligand may have some binding interface overlap with antibody binding at the C-terminus of Akt1.

Competition ELISA experiments suggested that the triligand binding site on Akt may partially overlap with that of an anti-Akt1 antibody directed toward the C-terminus (FIG. 30). The C-terminus is effectively on the "backside" of the kinase domain, opposite the active site.

Example 5: Diagnostic Efficacy of Akt Capture Agents

The Akt capture agents generated in Example 1 were evaluated for their ability to recognize full-length Akt from cancer lines. Previous studies have shown that Akt2 is overexpressed in the OVCAR3 ovarian cancer cell line. Therefore, this cell line was utilized as an experimental platform for immunoprecipitation (IP) and immunohistochemical experiments (IHC) (Yang 2004).

For the IP experiments, the anchor, biligand, and triligands were immobilized on streptavidin-agarose, and each resin was panned with OVCAR3 cell lysates obtained from untreated cells or cells stimulated with a combination of epidermal growth factor (EGF) and insulin.

OVCAR3 cells were grown in RPMI-1640 media containing 10% fetal bovine serum, penicillin, and streptomycin. Passage 4 cells were grown to ~60% confluence and treated with insulin and EGF at final concentration of 10 µg/mL and 20 ng/mL respectively (induced) or mock treated (control). Cells were grown for an additional 24 hours and then lysed with lysis buffer (10 mM Tris-Cl (pH=7.5), 100 mM NaCl, 1% (v/v) Triton X-100, 0.1% SDS (w/v), 0.5% deoxycholate, 1 mM DTT, 1 mM EDTA, 1× PhosStop phosphatase inhibitors (Roche), 1× Complete protease inhibitors (Roche). Cell lysate protein concentrations were determined by Bradford assays.

Ligands were immobilized on Streptavidin-agarose by adding 9 µL of 4 mM ligand stock (DMSO) to 50 µL of streptavidin-agarose resin (EMD) pre-blocked in Akt blocking buffer. The mAb resin was prepared by adding 25 µg 5G3 anti-Akt1 antibody (Cell signaling technology) to 100 µL streptavidin resin in Akt blocking buffer. After binding for 1 hour at 4° C., 50 µM D-biotin was added to the resin to block any remaining sites.

10 µL of resin-bound ligand was added to a Spin-X filter unit (Sigma) and filtered. To this was added OVCAR3 cell lysate (80 µg protein by Bradford) and Akt blocking buffer to a final volume of 50 µL. Binding occurred at 4° C. for 20 hours with agitation. The resins were washed three times in Akt blocking buffer, three times in Akt Wash 1 buffer, and three times in Akt Wash 2 buffer. The bound material was eluted by adding 40 µL 2×SDS-PAGE loading buffer (Bio-Rad) and heating at 94° C. for 10 minutes. A portion of each elution was run on duplicate 12% SDS-PAGE gels (Bio-Rad). One gel was stained with Coomassie while the other was transferred to nitrocellulose, blocked in 5% non-fat milk, and probed overnight with Rabbit pan-Akt monoclonal antibody (C67E7, Cell Signaling Technology) followed by anti-rabbit-HRP secondary antibody. The primary antibody was used at 1:1000 dilution and the secondary antibody was used at 1:10000 dilution. The blots were developed with Pico West Dura ECL substrate (Thermo) and imaged on film.

Figure 25:
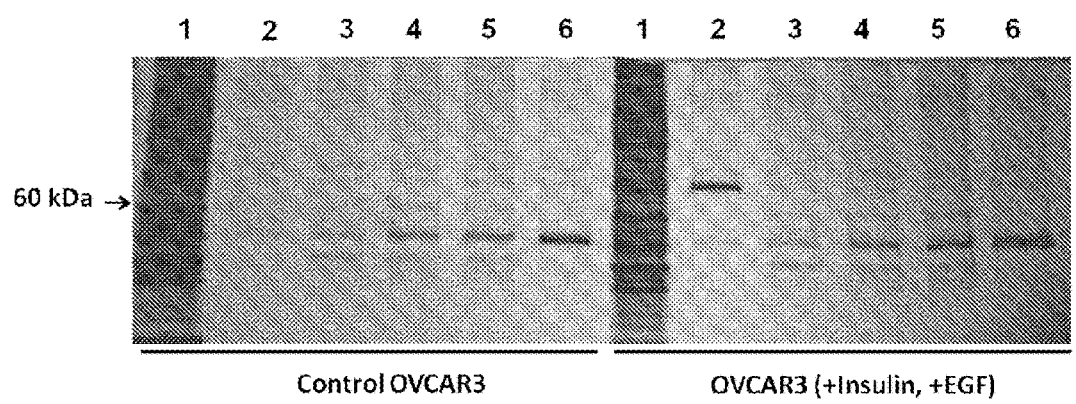
FIG. 25: Coomassie-stained gel from immunoprecipitation experiment. A representative 12% gel stained with Coomassie and imaged. Lane 1: Lysate, Lane 2: Anchor resin, Lane 3: Biligand resin, Lane 4: Triligand resin, Lane 5: 5G3 mAb resin.
Figure 26:
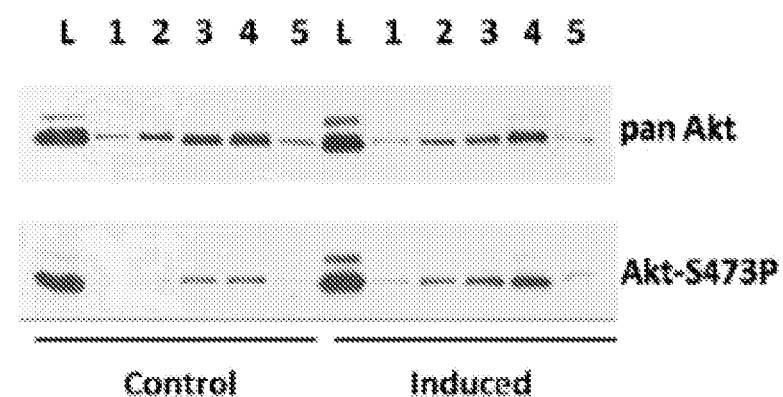
FIG. 26: Biotinylated ligands were immobilized on streptavidin agarose and incubated with lysates from OVCAR3 cell lines treated with EGF and insulin (induced) or untreated (control). After 18 hours at 4° C., resins were washed exhaustively, eluted with SDS-PAGE sample buffer, and analyzed by Western blotting. 1. Blank resin, 2. Anchor, 3. Biligand, 4. Triligand, 5. [5G3] mAb, L. lysate.

Probing the elutions with pan-Akt antibody, which detects all three isoforms of Akt, confirmed the increased affinity of the biligand relative to the anchor peptide in lysates from both induced and non-induced cells (FIG. 26). The triligand shows somewhat increased immunoprecipitation of Akt relative to the biligand in induced cell lysates but not in the non-induced control cell lysate. This effect is also observed when the immunoprecipitations are probed with an antibody specific for Akt phosphorylated Ser473 (Ser474 in Akt2). Analysis of the total immunoprecipitated protein by SDS-PAGE showed no significant difference in background (non-selective) binding between any of the ligands (FIG. 25). Interesting, the commercial anti-Akt1 antibody, which was also raised against the kinase domain of Akt1, showed almost no immunoprecipitation of Akt. The poor performance of this antibody was observed across many assays and across multiple batches of antibodies. Even for an equivalently performing antibody, the ability to use large amounts of triligand at relatively low cost relative to monoclonal antibodies represents a significant advantage.

Figure 17:
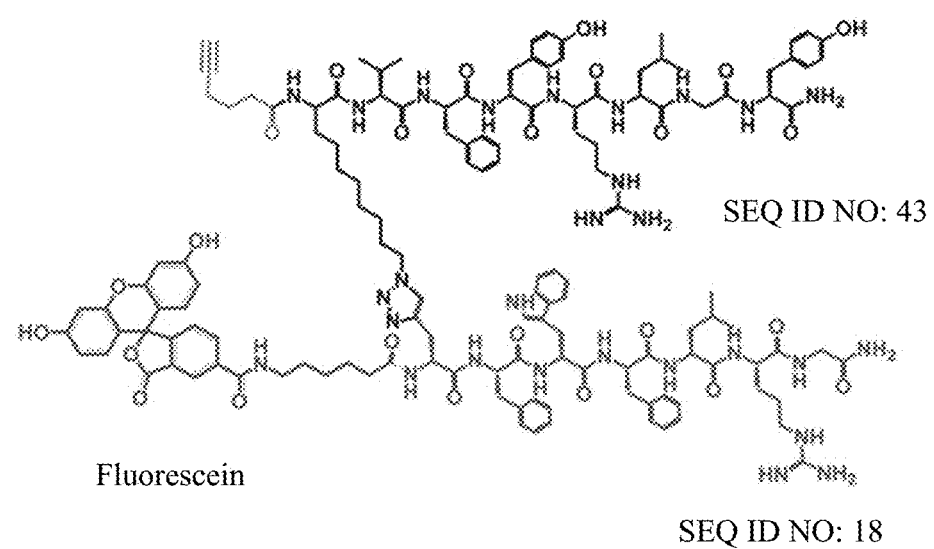
FIG. 17: Structure of fluorescein-biligand.

To further explore the interaction between the multiligand capture agent and full-length Akt, a fluorescein-labeled biligand was synthesized (FIG. 17) for use as an IHC imaging agent in fixed OVCAR3 cells. The anchor peptide $C_8N_3$-VFYRLGY-CONH$_2$ (SEQ ID NO: 43) was synthesized on Rink Amide resin as previously described. The secondary peptide Pra-FWFLRG-CONH$_2$ (SEQ ID NO: 18) was synthesized on Seiber Amide resin as described above. After Fmoc deprotection the fluorescein derivative 6-[Fluorescein-5(6)-carboxamido]hexanoic acid (Sigma) was conjugated to the amino terminus of the secondary peptide using 1.2 equivalents of fluorescein, 1.1 equivalents of HATU, and 3 equivalents of DIEA, then incubated at room temperature for 30 minutes. Following cleavage from resin, C18 RP-HPLC purification, and MALDI-TOF verification of the product, the secondary peptide was coupled to the anchor peptide via copper catalyzed azide-alkyne cycloaddition by addition of 1 equivalent of anchor peptide with 2 equivalents of fluorescent secondary peptide, 4 equivalents of CuI and 6 equivalents of Ascorbic Acid. After C18 RP-HPLC purification, the final product was verified by MALDI-TOF MS: Expected $[M+H]^+$=2612.00, Observed $[M+H]^+$=2612.78. Fluorescent biligand was then used for subsequent imaging experiments.

Figure 18:
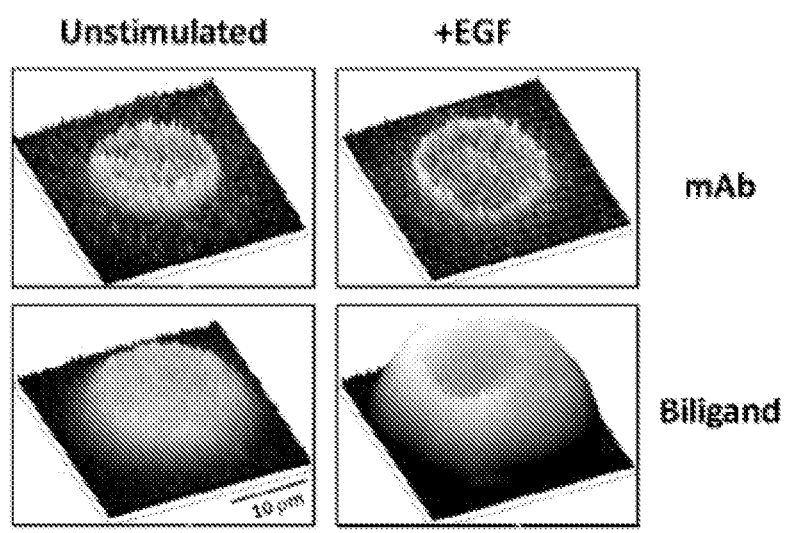
FIG. 18: Immunofluorescent images of Akt in fixed OVCAR3 cells stained with either a fluorescein-conjugated anti-AKT antibody or a fluorescein-conjugated biligand. Each imaging agent distinguishes cytoplasmic or membrane-bound AKT in unstimulated or EGF-treated cells, respectively.

OVCAR3 cells were grown on polylysine coated coverslips and treated with either 500 ng/mL EGF (Sigma) or vehicle control for 10 minutes. Cells were then fixed with 10% formaldehyde for 15 min at 37° C., washed with PBS, permeablized by incubating with 0.1% Triton X-100 for 10 min at room temperature, and blocked with 5% goat serum. Permeabilized cells were stained with either a fluorescein-conjugated Pan Akt antibody (R&D Systems IC2055F, 10 µg/mL) overnight or 1 µM fluorescein conjugated biligand for 1 hour. Images were acquired using a Zeiss Pascal 5 Laser Scanning Microscope (Caltech Biological Imaging Center) and surface plots were generated with ImageJ software (NIH). For this assay, Akt was expected to locate to the cell membrane following stimulation of a receptor tyrosine kinase such as epidermal growth factor receptor (EGFR) by its ligand (EGF). Images of unstimulated and stimulated cells clearly reveal that this was the case (FIG. 18).

Example 5: Targeting the Phosphorylation Site of Serine474 (S474) on the Kinase Domain of the Protein Akt (Protein Kinase B)

For this demonstration, a capture agent was designed to selectively bind to the key activating phosphorylation site of Protein Kinase B (Akt2). The overall strategy was as follows.

A 32mer target peptide sequence was built including amino acids 450-481 of Akt2. This sequence contains the targeted phosphorylation site (S474). S474 was phosphorylated.

Figure 35A:
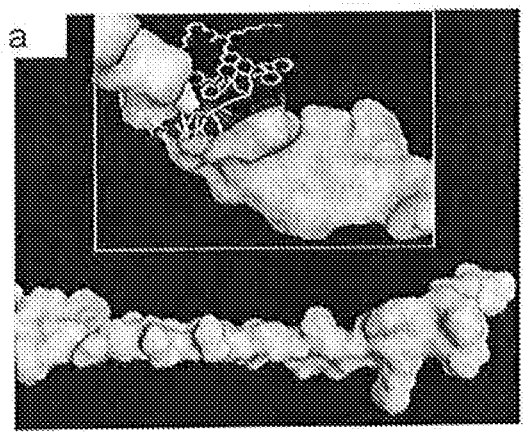
FIGS. 35A-B: A schematic showing a screening strategy for developing a capture agent against the epitope of the Akt kinase domain associated with the phosphorylated Serine 474.
Figure 35B:
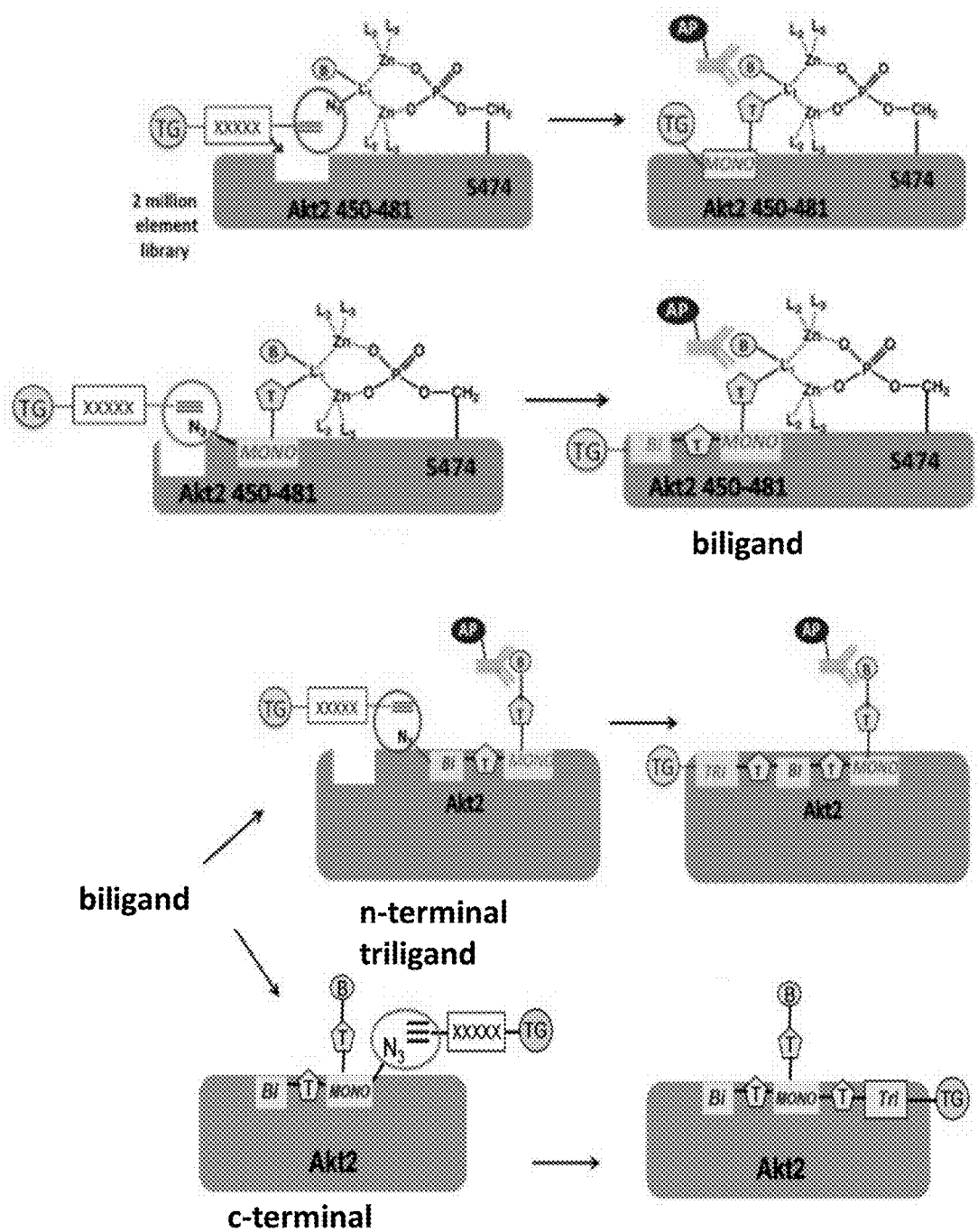

A metallorganic molecule (Biotin-PEG2-Az4-Zn$_2$L) was utilized that selectively binds to the phospho group on the p-S474 site of the 32-mer polypeptide. Biotin-PEG2-Az4-Zn$_2$L also was designed to present an azide group near the p-S474 site. Biotin-PEG2-Az4-Zn$_2$L as shown in FIG. 35.

An in situ click screen was carried out by incubating the (Biotin-PEG2-Az4-Zn$_2$L) (32-mer) complex with a large one-bead one compound (OBOC) peptide library. Each peptide in the library contains an acetylene group, and the library contains approximately 2 million distinct molecules. The basic strategy of this screen is shown in FIG. 35.

Figure 36A:
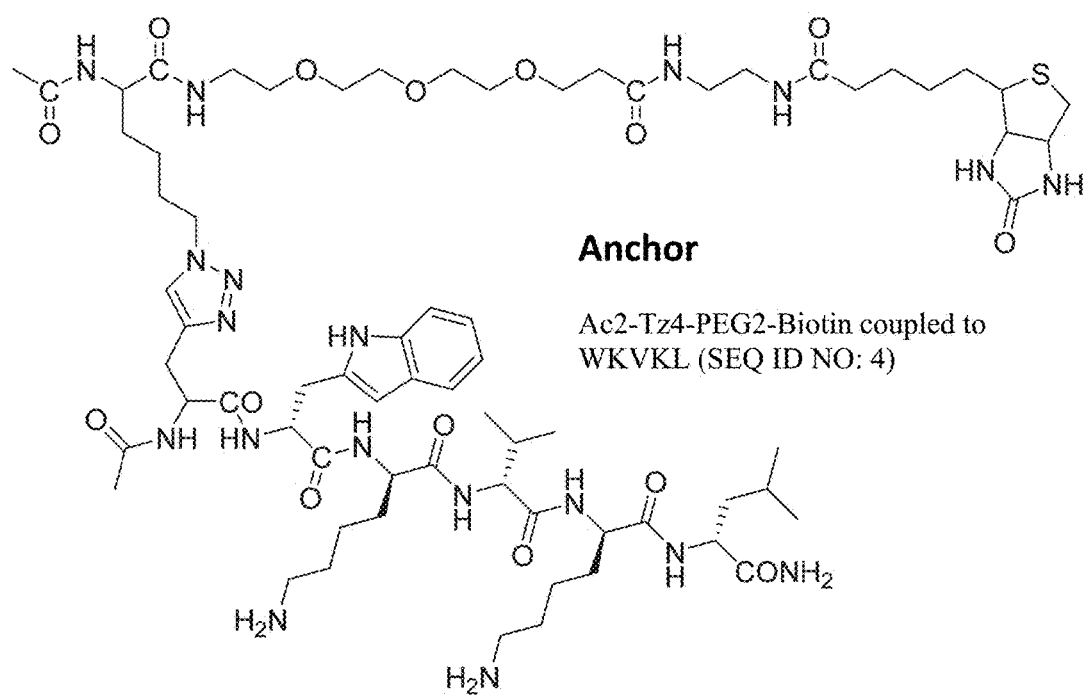
FIGS. 36A-E show the structures of four capture agents targeted against Ser474 of Akt2.

A sequence was identified and those hit molecules that exhibit the best binding characteristics were validated. The hits from this screen are listed in Table 3. The structure of the capture agent identified from this screen is shown in FIG. 36a. This capture agent was able to detect Akt from cell lysate, using the ovarian cancer cell line OVCAR3, in which Akt is overexpressed.

Figure 36B:
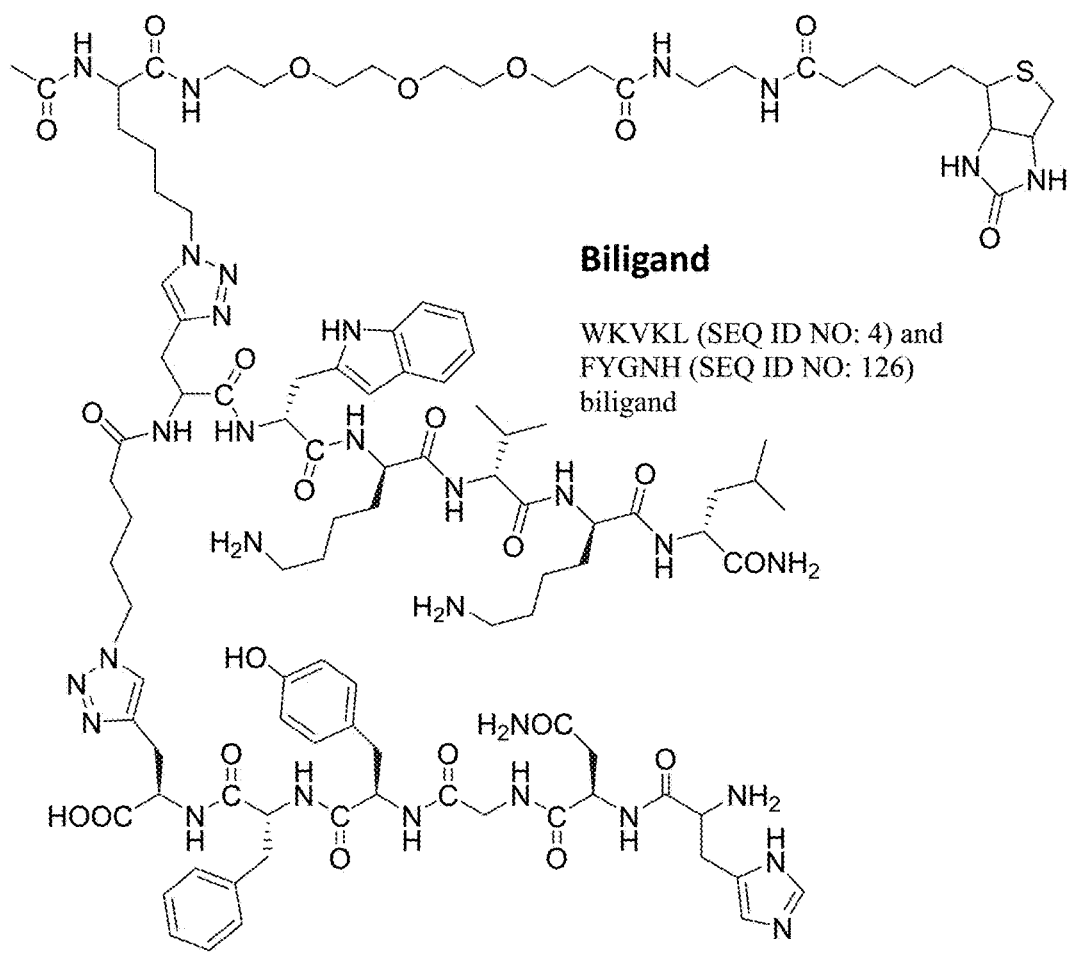
Figure 36C:
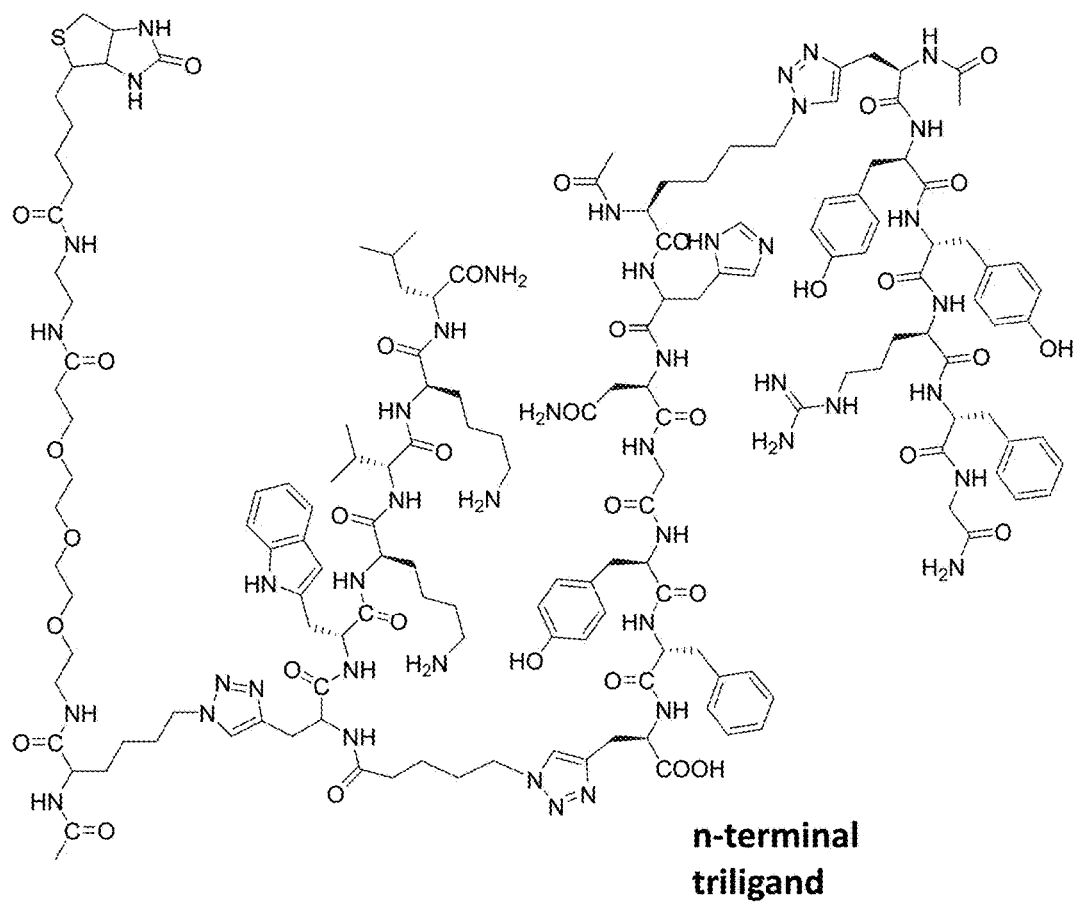
Figure 36D:
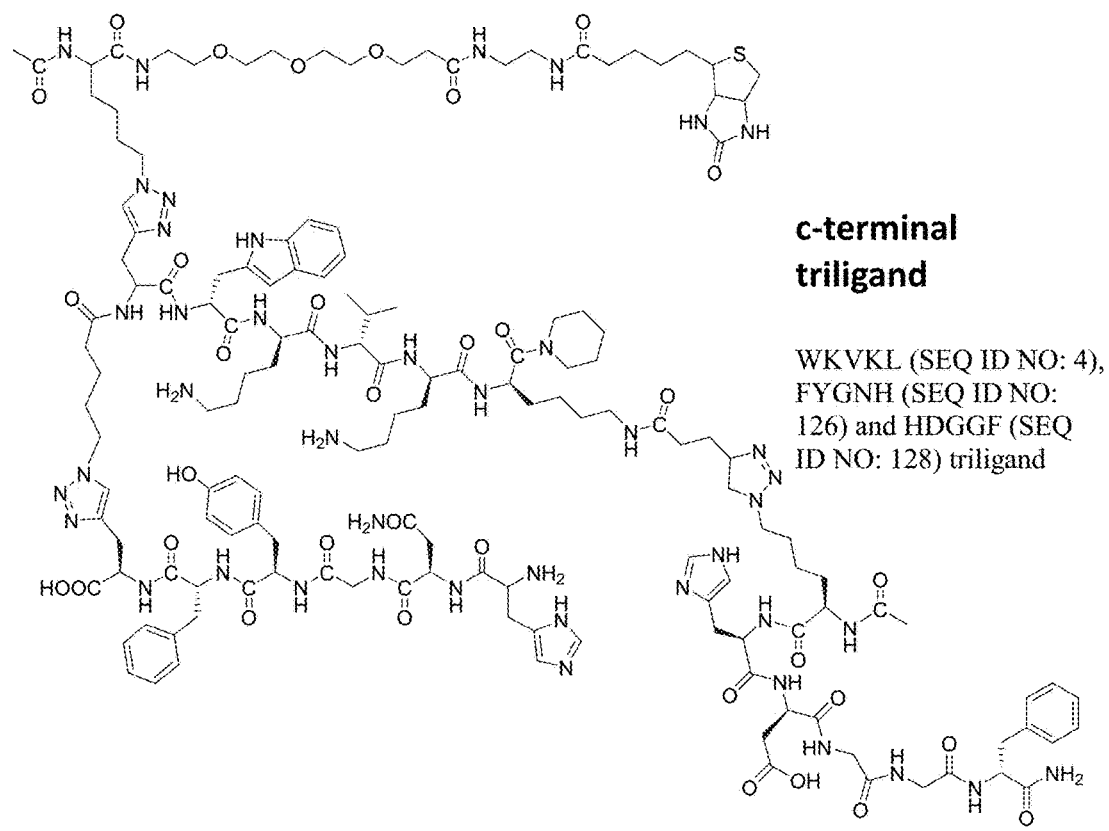
Figure 36E:
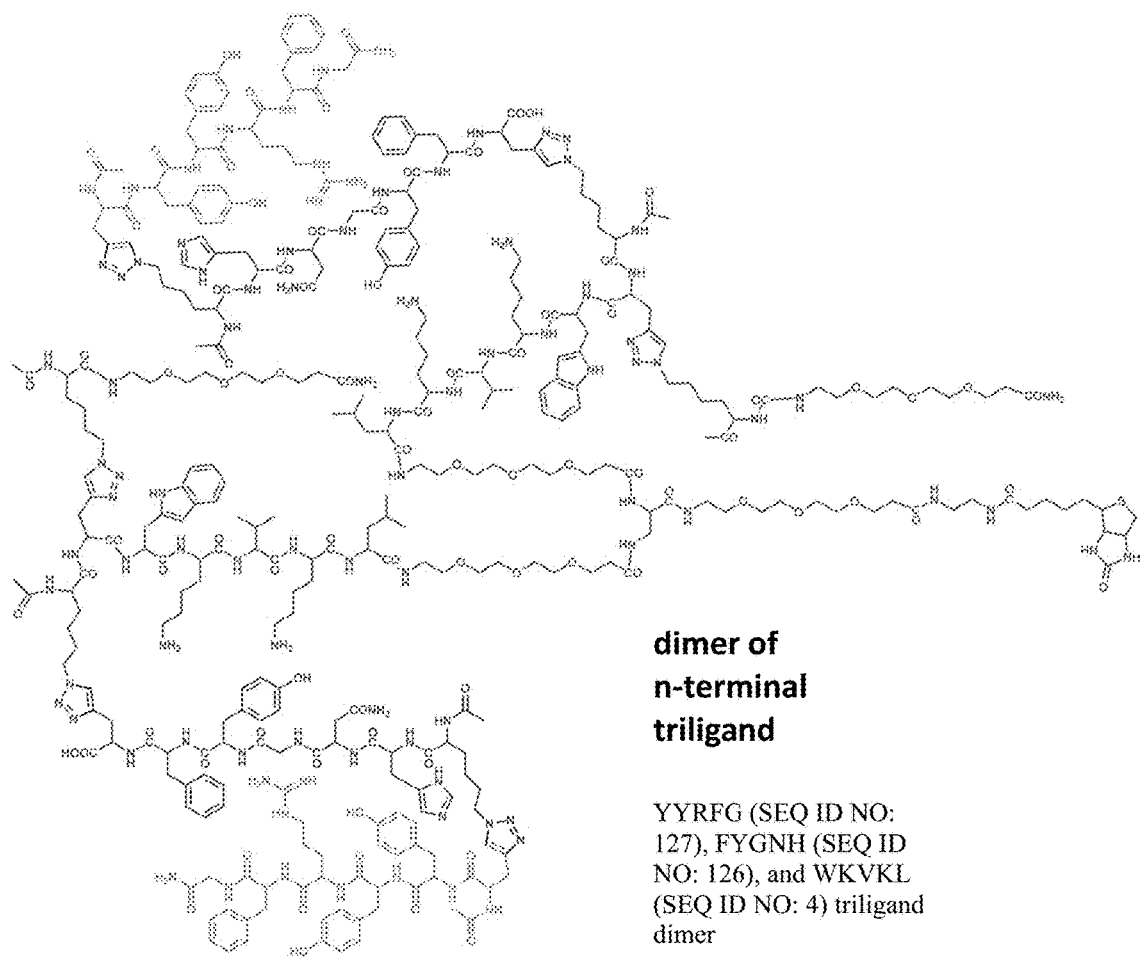
Figure 37A:
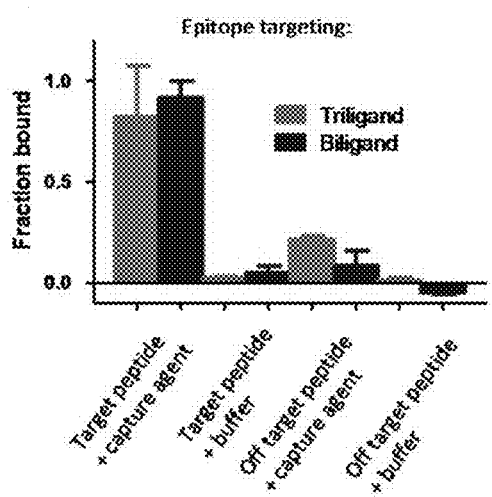
FIGS. 37A-C show selectivity and affinity assays for some of the anti-Ser474 Akt2 PCC composition. All triligand data refers to the n-terminal triligand.
Figure 37B:
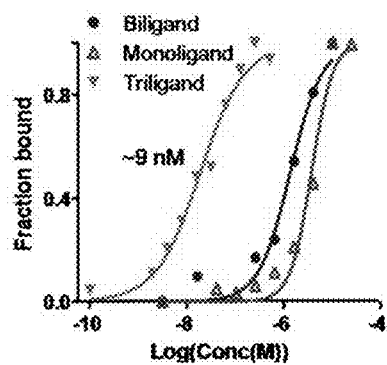
Figure 37C:
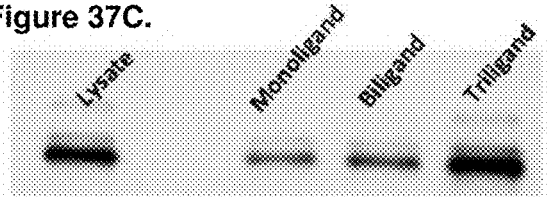
Figure 38:
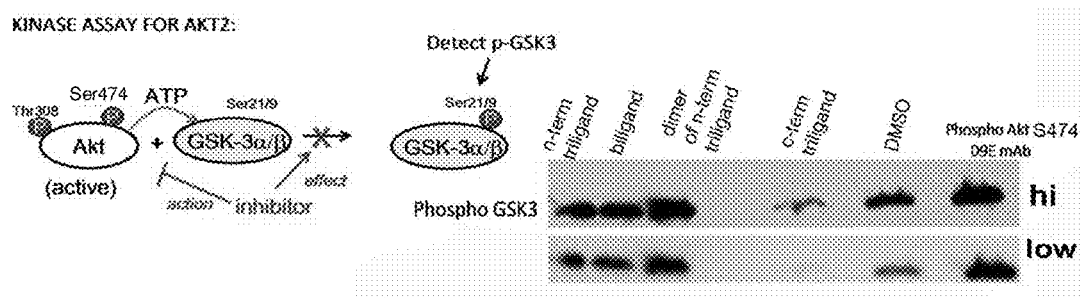
FIG. 38, at left, a schematic for a standard inhibition assay that tests the influence of the anti-p-Ser474 Akt2 PCC composition, as well as the same-site-targeted commercial antibody, against the kinase activity of Akt. PCC compositions, developed using the epitope targeting strategy, make non-traditional enzyme inhibitors. If Akt2 is activated by phosphorylation of Ser474 then, in that state, it phosphorylates GSK-3a/b. If it is further activated via a steric effect, then it will produce more p-GSK-3a/b. If that same Akt2 is inhibited, then it will produce less p-GSK-3a/b. Thus, the signature of Akt inhibition (or activation) is read out as p-GSK-3a/b abundance, relative to the DMSO control. Assays are shown at right in the form of Western Blots. The DMSO column gives the baseline level. The n-terminal triligand the biligand, the dimer of the n-terminal triligand, and the commercial monoclonal antibody all activate Akt relative to DMSO. The c-terminal triligand inhibits Akt. The 'hi' and 'low' blots correspond to long and short development times, respectively. The Akt2 protein used for the inhibition assay is active Akt2 that is phosphorylated at Thr308, and is at least partially phosphorylated at Ser474, since the antibody for pSer474 detects the pSer474.

The characteristics of this best ligand were improved through use of sequential in situ click chemistry, as described in *Capture Agents and Related Compositions, Methods, and Systems* CIT 5164-P; and *Akt-Specific Capture Agents, Compositions, and Methods of Using and Making.* CIT 5917-P, Agnew, et al., *Angew. Chem.* 121, p 5044-5048 (2009), and Millward, et al., *J. Am. Chem. Soc.* 133, 1820 (2011), incorporated herein by reference in their entireties. For these steps, the capture agent that was identified in Steps (1)-(4) was improved into a biligand (FIG. 36b), and then a triligand (FIG. 36c). The capture agent was shown to selectively bind to the polypeptide fragment containing S474, but not to another 32-mer fragment from the same protein (FIG. 37). It exhibited a strong affinity ($K_D$~10 nanoMolar) and high selectivity for Akt, relative to other similar kinases, and could be used, in an immunoprecipation assay, to selectively detect Akt protein from cell lysate. The performance of this capture agent is shown in FIG. 38.

Experimental Details

Materials.

Fmoc-protected amino acids were purchased from Anaspec (San Jose, Calif.) and AAPPTec (Louisville, Ky.) and used as received. TentaGel S—$NH_2$ resin (90 μm, 0.31 mmol/g) was obtained from Anaspec (San Jose, Calif.) and utilized for OBOC library construction. Biotin NovaTag™ resin, Biotin-PEG NovaTag™ resin, Fmoc-NH-$(PEG)_2$-COOH (13 atoms) were obtained from EMD Chemicals, Inc. (Gibbstown, N.J.) and used for synthesis of biotinylated peptides. Peptides and OBOC peptide libraries were synthesized on the Titan 357 peptide synthesizer (AAPPTec Louisville, Ky.). Amino acid coupling reactions were performed in 1-methyl-2-pyrrolidinone (NMP, 99%) with HATU (2-(7-Aza-1H-benzotriazole-1-yl)-1,1,3,3-tetramethylammonium hexafluorophosphate, ChemPep, Miami, Fla.) and N,N'-diisopropylethylamine (DIEA) (99%, Sigma-Aldrich, St. Louis, Mo.). For removal of $N^\alpha$-Fmoc protecting groups, a solution of 20% piperidine in N,N'-dimethylformamide (DMF) was used (Sigma-Aldrich, St. Louis, Mo.). For final deprotection of peptides, trifluoroacetic acid (TFA, 98% min. titration) and triethylsilane (TES) were used (Sigma-Aldrich, St. Louis, Mo.).

Active Akt2 (with N terminal His tag) was purchased from Abcam (Cambridge, Mass.).

Peptide Library Synthesis:

Randomized OBOC libraries of hexapeptides were synthesized using the Titan 357 peptide synthesizer on 90 μm polyethylene glycol-grafted polystyrene beads (TentaGel S-$NH_2$, 0.31 mmol/g, $2.86 \times 10^6$ beads/g). D amino acids were used for the synthesis of the library. The libraries used in this study are listed in the table 2.

TABLE 2

| Formula | Components | # of unique sequences |
| --- | --- | --- |
| Library A: D-Pra-$X_1X_2X_3X_4X_5$ | $X_i$ = 18 D amino acids except D-Met and D-Cys | 1,889,568 |
| Library B: $X_1X_2X_3X_4X_5$-D-Pra | $X_i$ = 18 D ammo acids except D-Met and D-Cys | 1,889,568 |

Preparation of 3,5-bis((bis(pyridin-2-ylmethyl) amino)methyl)-4-hydroxybenzoic acid (HL)

Figure 34:
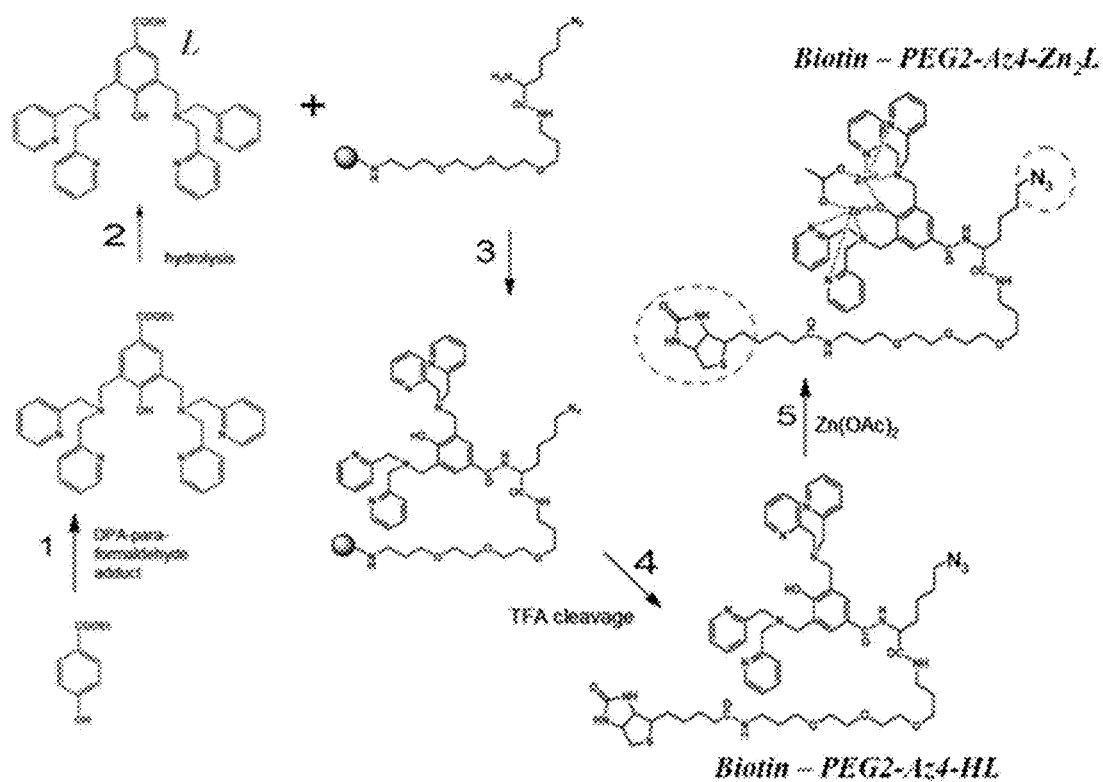
FIG. 34: A schematic showing synthesis of the metallorganic ligand for binding to the phospho-group on a phosphorylated amino acid residue of a protein, peptide, polypeptide. The azide group and the biotin group are indicated on the Biotin-PEG2-Az4-$Zn_2L$ structure.

To N,N-di(2-picolyl)amine (2.50 g, 12.5 mmol) in ethanol/water/HCl (30 mL/90 mL/0.6 mL of 2M) was added to paraben (830 mg, 2.50 mmol) and paraformaldehyde (475 mg, 15.85 mmol). The mixture was heated under reflux for 3 days and then allowed to cool to room temperature. Then 200 mL dichloromethane (300 mL) and water (100 mL) was added to the reaction mixture, the organic phase was separated after washing with another 300 mL of water and dried over anhydrous sodium sulphate. A yellowish gummy semi-solid was obtained after evaporation of solvent. Column chromatography on silica gel with eluents dicholoromethane/methanol/ammonium hydroxide afforded light yellow semi solid. Refer to FIG. 34 for structure of HL Then the purified semisolid was dissolved in 2 M solution of sodium hydroxide in water/ethanol (1:1) mixture and stirred at 60 deg centigrade for 2 days. Then the solution was neutralized by concentrated hydrochloric acid. The compound was extracted by methanol.

Calculated mass: $[M+H]^+$ 561.3, $[M-H]^-$ 559.3. Observed mass: $[M+H]^+$ 561.3, $[M-H]^-$ 559.4.

Preparation of Biotin-PEG2-azidolysine-HL (Biotin-PEG2-Az4-HL)

DL Fmoc-azidolysine was coupled to Biotin PEG Novatag resin (coupling efficiency 0.00048 mmole/g) following standard Fmoc solid phase synthesis protocol. The $N^\alpha$-Fmoc protecting group was removed by treating with 20% piperidine in NMP. Then 3,5-bis((bis(pyridin-2-ylmethyl)amino)methyl)-4-hydroxybenzoic acid (L) was coupled overnight to the resin. The molecule was cleaved off the resin using a cocktail of TFA, TES and double distilled water (95:2.5:2.5), precipitated in cold ether and lyophilized. The crude solid was used in further synthesis. Refer to FIG. 34 for structure of Biotin-PEG2-Az4-HL Preparation of Biotin-PEG2-Azidolysine-L$Zn_2$ (OAc) (Biotin-PEG2-Az4-$Zn_2$L) (Structure 3 of FIG. 34)

2 equivalents of zinc acetate was dissolved in methanol and added to 1 equivalent of Biotin-PEG2-Az4-HL and stirred overnight at room temperature. The solvent was removed under reduced pressure and the solid was purified using a gradient of water and acetonitrile and 0.1% TFA on the RP-HPLC (Beckman Coulter System Gold 126 Solvent Module and 168 Detector) using a $C_{18}$ reversed phase semi-preparative column (Phenomenex Luna 10 μm, 250× 10 mm). Refer to FIG. 34 for structure of Biotin-PEG2-Az4-$Zn_2$L.

Calculated mass: $[M].2H_2O$ 1369.5 Observed mass: $[M].2H_2O$ 1369.4.

Synthesis of Target Peptide Sequence (p32mer)

The 32mer target peptide sequence, amino acids 450-481 of Akt2, was synthesized on Rink Amide MBHA resin, using the Titan 357 peptide synthesizer. Fmoc-Ser($OPO_3$Bzl)-OH (Aapptec) was used for the solid phase synthesis of the phosphoserine. It was cleaved by TFA, precipitated in cold ether and purified using a gradient of water and acetonitrile and 0.1% TFA on the RP-HPLC.

Calculated mass: $[M+H]^+$ 3832. Observed mass: $[M+H]^+$ 3831.0.

Synthesis of Monoligand

Fmoc-NH-PEG2-COOH (EMD) was coupled using standard Fmoc protocol on Biotin Novatag resin. 1.5 equivalent of DL Fmoc-azidolysine was coupled on the resin followed by acylation using acetic anhydride and 2, 6-lutidine solution in DMF. On bead click reaction overnight is carried out using 2 equivalents of Fmoc-D-Pra-OtBu, 0.9 equivalent CuI and 1.2 equivalent ascorbic acid in 20% piperidine/DMF solution. Following washes with copper chelating solution (5% sodium diethyl dithiocarbamate, 5% DIEA in DMF) the peptide was acylated. The resultant molecule Ac2-Tz4-PEG2-Biotin was cleaved off the resin using TFA cleavage cocktail. The crude solid was used in further synthesis.

The peptide wkvkl (SEQ ID NO:4) was made on Rink Amide MBHA resin (Anaspec) following standard Fmoc SPPS synthesis protocol. 1 equivalent of Ac2-Tz4-PEG2-Biotin was then coupled to the peptide.

After TFA cleavage the monoligand was purified using a gradient of water and acetonitrile and 0.15 TFA on the RP-HPLC.

Calculated mass: [M+H]$^+$ 1495.85. Observed mass: [M+H]$^+$ 1496.0.

Screening Procedure for Detection of Monoligand (Epitope Targeting Screen):

10 nM and 50 nM solutions of p32mer were made by diluting 0.5 mg/ml DMSO stock in 25 mM tris chloride, 150 mM NaCl, 2 mM KCl, pH 8)(TBS). 20 μM and 100 μM solutions of the metal chelated anchor (Biotin-PEG$_2$-Az4-Zn$_2$L) was added to the 10 nM and 50 nM solutions of the p32mer respectively and shaken overnight at room temperature. Before the addition to the OBOC library, BSA and tween 20 was added to the solution to make the final concentrations 0.1% BSA and 0.05% tween 20 in the buffer.

Anchor peptide screens were conducted using library A. 250 mg of beads were screened per screen. The beads were equilibrated in 0.1% BSA, 0.05% Tween 20/TBS (binding buffer) by shaking for 10 hours.

The preincubated p32mer-Biotin-PEG$_2$-Az4-Zn$_2$L mixture was added to the preswelled beads and shaken overnight at room temperature. The beads were washed three times with buffer. A 1:10,000 dilution of mouse anti biotin monoclonal antibody-Alkaline Phosphatase conjugate (Sigma) in buffer was added to the beads. The beads were then extensively washed with binding buffer, 0.05% tween 20/TBS and TBS.

The beads were then treated with a BCIP solution (made according to the manufacturer's protocol). The hit beads turned blue due to a colorimetric reaction of Alkaline Phosphatase with BCIP. The reaction was quenched after an hour with 0.1N HCl solution. The hit beads were picked with a pipette tip and transferred to a spinnex tube.

The color of the hit beads was removed by washing with DMF. The proteins on the beads were stripped off by treating with 7.5 M guadininium hydrochloride (pH 2) for two hours and then washing extensively with water.

The hit beads were reequilibrated in binding buffer. The exact screen protocol was repeated, this time using a preincubated mixture of 2.5 mM biotin and 1:10,000 dilution of a mouse anti biotin monoclonal-Alkaline Phosphatase conjugate (Sigma) as the secondary antibody. On addition of the BCIP, the true hits, due to competition with biotin remained clear. The clear beads were manually picked, washed with 7.5 M guanidium hydrochloride (pH 2) and water, and sequenced using the Edman Sequencer.

TABLE 3

Sequences of hits obtained from monoligand screen

| D-Pra | X1 | X2 | X3 | X4 | X5 | SEQ ID NO: |
|-------|----|----|----|----|----|------------|
| D-Pra | w  | k  | v  | k  | l  | 4          |
| D-Pra | w  | k  | v  | k  | l  | 4          |

Verification of Binding of Biotin-PEG2-Az4-Zn$_2$L to Phospho Amino Acid and Phospho Peptide:

422 μM Biotin-PEG2-Az4-Zn$_2$L solution was made dissolving the HPLC purified solid in 10 mM tris borate buffer (pH 8).

Saturated solutions of pure phosphoserine and pSrc substrate Ac-I-pY-GEF (Novabiochem) were made in 10 mM tris borate buffer (pH 8). Biotin-PEG2-Az4-Zn$_2$L was added to either of the saturated solutions in a 1:1 ratio.

A fresh matrix was prepared by dissolving 2,4,6-trihydroxyacetophenone in 10 mM tris borate buffer (pH 8) with 50% acetonitrile (20 mg/ml). The mixed solutions with the matrix clearly showed the peaks corresponding to (Biotin-PEG2-Az4-Zn$_2$L-pSer) and (Biotin-PEG2-Az4-Zn$_2$L-Ac-I-pY-GEF) in the Maldi TOF spectra in a positive mode.

Epitope Targeting Assay for Biligand:

1.25 μM biotinylated biligand was prepared by diluting the 1 mM stock in buffer (25 mM tris chloride, pH=7.4, 150 mM NaCl, 0.1% BSA, 0.05% Tween 20). The prepared ligand solution or DMSO in buffer (buffer control) was immobilized on a SA plate. After washing away the excess ligand, 2.5 μM solutions of the His tagged phospho peptide epitope Akt2 amino acids 450-481 or the His tagged control peptide Akt2 amino acids 346-378 was added to each of the wells. Following three washes with the buffer, the plate was treated for an hour with a 1:1000 dilution of anti His6 mouse monoclonal antibody. A 1:10,000 dilution of goat anti mouse antibody-Horse Radish Peroxide conjugate (Abcam) in binding buffer was added to the wells. Color was developed by adding TMB substrate (KPL) to each well. The reaction was quenched with 0.5 M H2SO$_4$. The A450 was measured on a 96-well plate reader. Net A450 was obtained by subtracting the absorbance value for no immobilized ligand from each of the triplicate values obtained for the ligand-epitope interaction.

Example 6: Targeting a Single (Cancer Causing) Amino Acid Substitution on the Plekstrin Homology Domain of Akt Akt1 is a commonly studied protein in relation to cancer, as its localization to the plasma membrane initiates important downstream signaling pathways in a cell. The Akt1 protein docks to the membrane through a domain that is highly structurally conserved among many proteins that bind to cell membranes—the Pleckstrin Homology Domain (PHD).

It has been discovered recently that a single amino acid point mutation, found in certain human ovarian, colorectal and breast cancers, in the binding pocket of this Akt1 PHD is enough to cause cancer in mice. The E17K mutation exchanges a negatively charged glutamic acid for a positively charged lysine. This change first eliminates a Glu-Lys hydrogen bond inside the binding pocket of un-docked Akt1 PHD; the E17K lysine repels a second hydrogen bond, and causes a structural change in the protein. Second, this E17K residue forms an additional hydrogen bond between the Akt1 PHD, a water molecule, and the PIP3 lipid on the cell membrane—either increasing the affinity of the PHD for the PIP3, or decreasing the off-rate for the PIP3. Either way, this single point mutation is enough to make the E17K Akt1 bind four-fold stronger to the plasma membrane, and this up-regulation of the Akt1/PIP3 signaling pathway is enough to cause cancer in mice.

From a therapeutic point of view, blocking of this PIP3/Akt1 binding in cancers could help slow or stop the growth of these cancers cells in humans and serve as a potential chemotherapy. By targeting the specific E17K point mutation, the side-effects and toxicity could be minimized. From a diagnostic point of view, a capture agent that can selectively recognize the E17K PHD of Akt1 would be useful.

Thus, for this reduction of the invention to practice, we seek to develop a capture agent that selectively binds to the E17k PHD of Akt1, while not binding to the wild-type.

Experimental Procedures

Peptide Library Construction:

Peptide libraries were synthesized on a Titan 357 split-and-mix automated peptide synthesizer (Aapptec) via standard FMOC SPPS coupling chemistry [1] using 90 uM TentaGel S—$NH_2$ beads (0.29 mmol/g, $2.86 \times 10^6$ beads/g). Libraries contain 18 D-stereoisomers of the natural amino acids, minus Cysteine and Methionine, at each of five randomized positions and an azide in situ click handle. At least a five-fold excess of beads is used when synthesizing libraries to ensure oversampling of each sequence. Amino acid side-chains are protected by TFA labile protecting groups that are removed all at once following library synthesis.

Bulk Peptide Synthesis:

Bulk synthesis of polypeptide sequences was performed using standard FMOC SPPS peptide chemistry either manually, or on a Titan 357 automated peptide synthesizer (AAPPTEC), or using a Liberty 1 microwave peptide synthesizer (CEM Corporation). The typical scale was 300 mg done on Rink Amide Resin beads (Anaspec). Peptides were cleaved from the beads with side-chains deprotected using a 95:5:5 ratio of TFA:$H_2O$:TES. The peptides were purified on a prep-scale Dionex U3000 HPLC with a reverse-phase C18 column (Phenomenex).

Akt1 Wildtype and E17K Mutant Pleckstrin Homology Domain Expression:

Akt1 Pleckstrin Homology Domain DNA was purchased from DNA2.0. The first 124 N-terminal amino acids from full length Akt1 were used as the PH Domain DNA (FIG. 39a), and a 6-his tag separated by a thrombin cleavage site were added at the C-terminus of the protein for purification. In order to make the E17K mutant of the PH Domain, the glutamic acid in position 17 was mutated to a lysine via QuikChange. The DNA was synthesized in a pJexpress 414 vector containing an amp resistant gene to be expressed in e coli cells. Protein expression was performed by the Protein Expression Center at Caltech using their standard bacterial expression protocol and purified via Ni-NTA column.

Figures 39A, 39B:
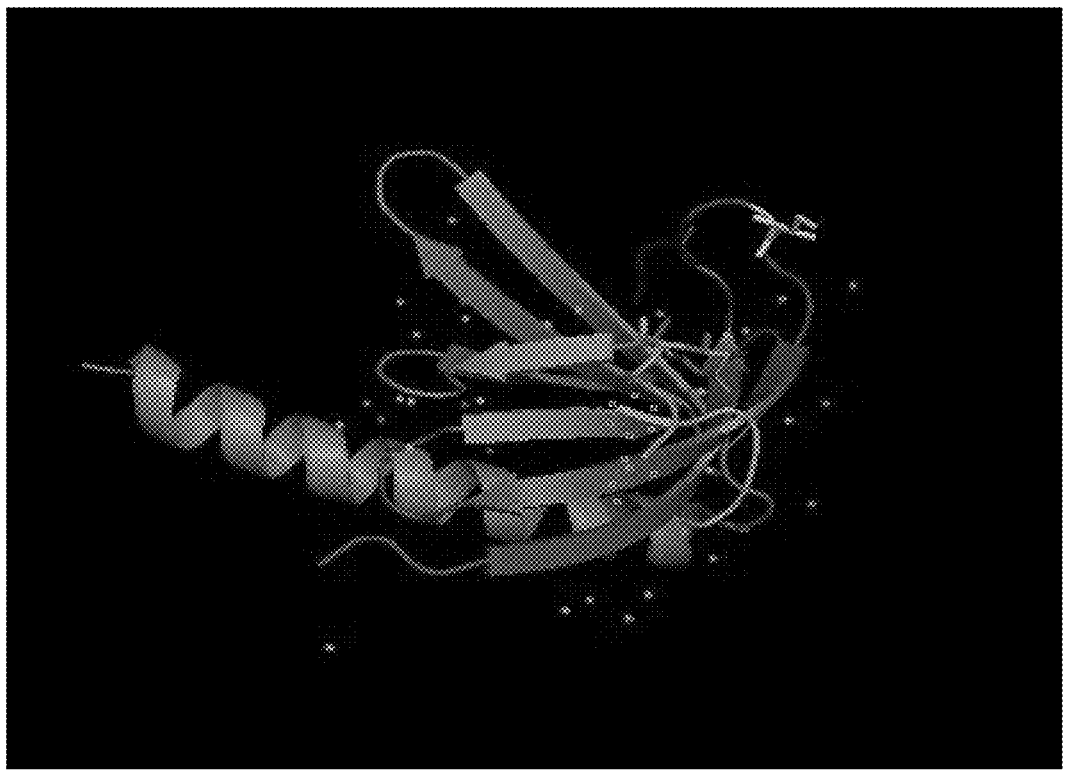
FIGS. 39A, 39B, and 39C show the design of 33-mer Target Fragment from Akt1 Pleckstrin Homology Domain.
Figure 39C:
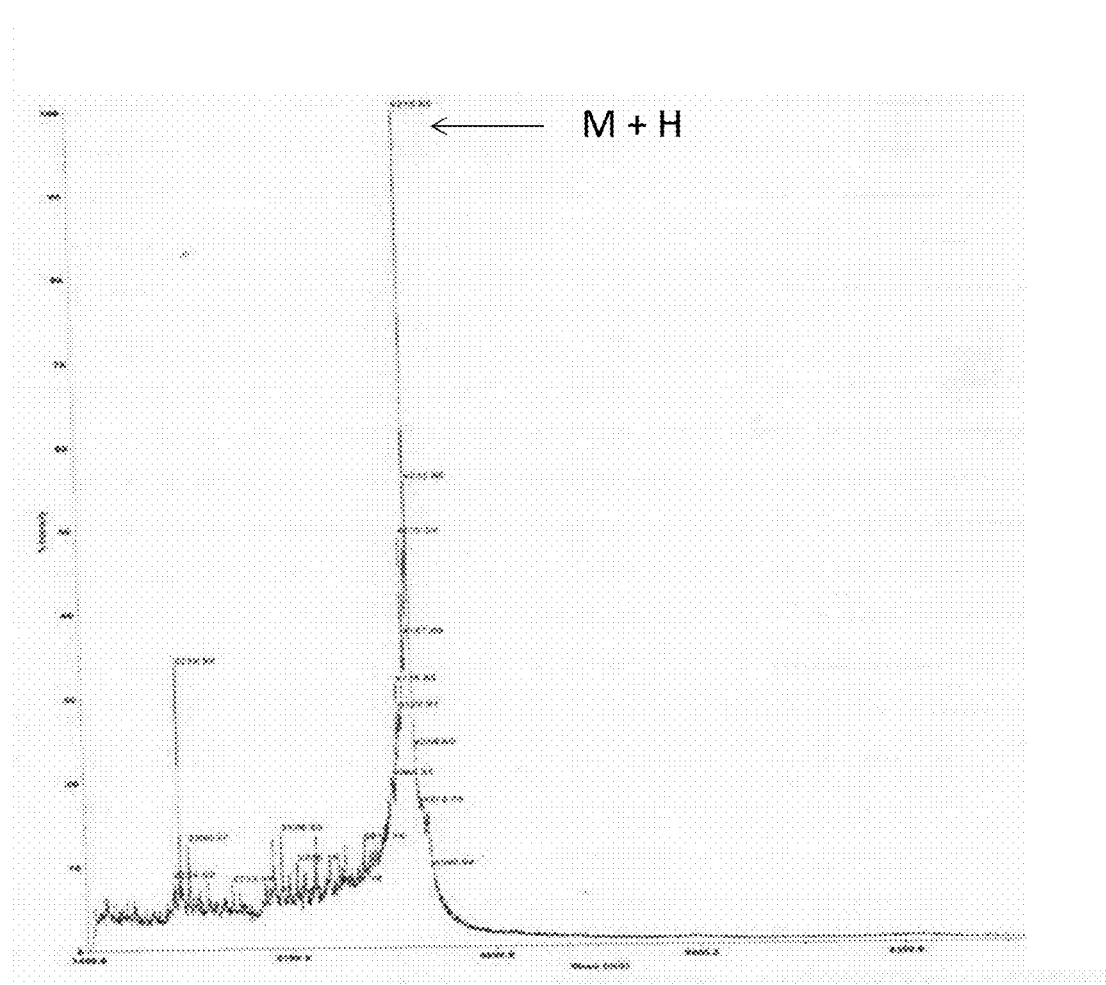

Design of Epitope-Targeting Anchor/Target Sequence:

Epitope targeting for the point mutation of the PH Domain of Akt1 was accomplished by screening against a 33-mer peptide fragment derived from the N-terminus of the PH Domain, highlighted in FIG. 39a, that contained the E17K point mutation as well as a propargylglycine (Pra) click-handle substitution (I19[Pra]) for directing the in-situ click reaction near the mutated site. The 33-mer fragment was capped with an N-terminal biotin label for detection in the screen (FIG. 39b), and was purified on a prep-scale Dionex U3000 HPLC with a reverse-phase C4 column (Phenomenex).

Figure 40A:
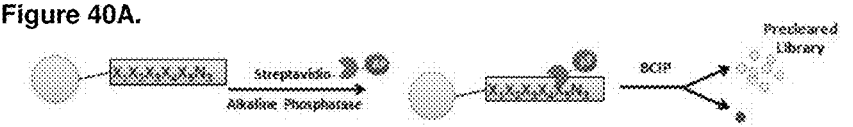
FIGS. 40A-B show a screening strategy for anchor ligand determination.
Figure 40B:
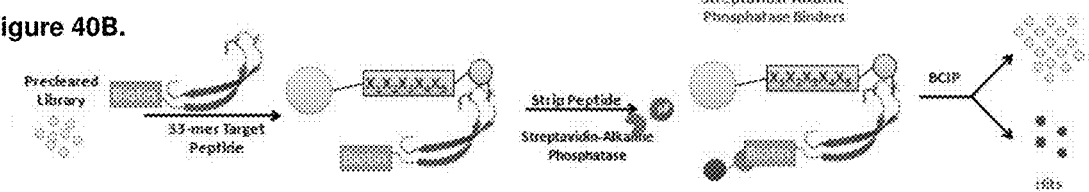

Screen for Epitope Targeted Capture Agents (FIG. 40):

Screens were done on a library with 100% Met coupled at the C-terminus for MALDI TOF/TOF sequencing. The library was a comprehensive 5-mer containing 18 unnatural D-amino acids, excluding Met and Cys due to stability reasons. The N-terminus contained an azide click handle with varying carbon chain lengths—2 carbon, 4 carbon and 8 carbon—for in vivo click with the Pra on the Target 33-mer. Screens were done with 300 mg of dried library beads swelled at least six hours in 1×TBS (25 mM Tris-Cl, 150 mM NaCl, 10 mM $MgCl_2$, pH=7.5) buffer.

Preclear (FIG. 40a):

Swelled library beads were blocked overnight in 5% w/v dried non-fat milk in 1×TBS, then washed with 1×TBS three times. Five milliliters of a 1:10,000 dilution of Streptavidin-Alkaline Phosphatase Conjugate in 0.5% milk in TBS was added to the beads and incubated shaking at room temperature for one hour. The beads were washed with a high-salt TBS buffer (1×TBS with 750 mM NaCl) three times, then let shake in high salt buffer for one hour. The beads were then washed three times with BCIP buffer (100 mM Tris-Cl, 150 mM NaCl, 1 mM $MgCl_2$, pH=9.0) and developed by adding 15 mL BCIP buffer plus 13 uL BCIP and 26 uL NBT. After one hour, the purple beads were removed by pipette and discarded. The remaining beads were incubated in NMP 4 hours to remove trace purple precipitate from the BCIP/NBT reaction, then were washed 5× with methanol, 5× with water, 5× with TBS and reblocked overnight in 5% milk.

Product Screen (FIG. 40b):

Beads remaining from the preclear were washed three times with 1×TBS, then incubated with 5 mL of a 100 nM dilution of the 33-mer target in 0.5% milk for either 5 hours or 12 hours to allow for an in situ click reaction to occur. The beads were then washed three times with 1×TBS and incubated for one hour with a 7M Guanadine-HCl buffer, pH=2.0 to remove all 33-mer target not attached covalently to the beads. These beads were then washed ten times with 1×TBS, reblocked for two hours in 5% milk, then incubated for one hour with a 1:10,000 dilution of Streptavidin-Alkaline Phosphatase conjugate in 0.5% milk in TBS to detect for the presence of the 33-mer target clicked to a bead. The beads were washed three times with a high-salt TBS buffer, then let shake in high salt buffer for one hour. Afterwards, the beads were again washed three times in BCIP buffer and developed as per the preclear. Purple beads are removed from the screen via pipette as hit beads. These hits were incubated in the guanidine-HCl buffer to remove attached streptavidin, washed ten times with water and sequenced via edman degradation on a Procise CLC system from Applied Biosystems. See Table 1 for sequences from 5 hour screen, Table 2 for sequences from 16 hour screen.

Figure 41:
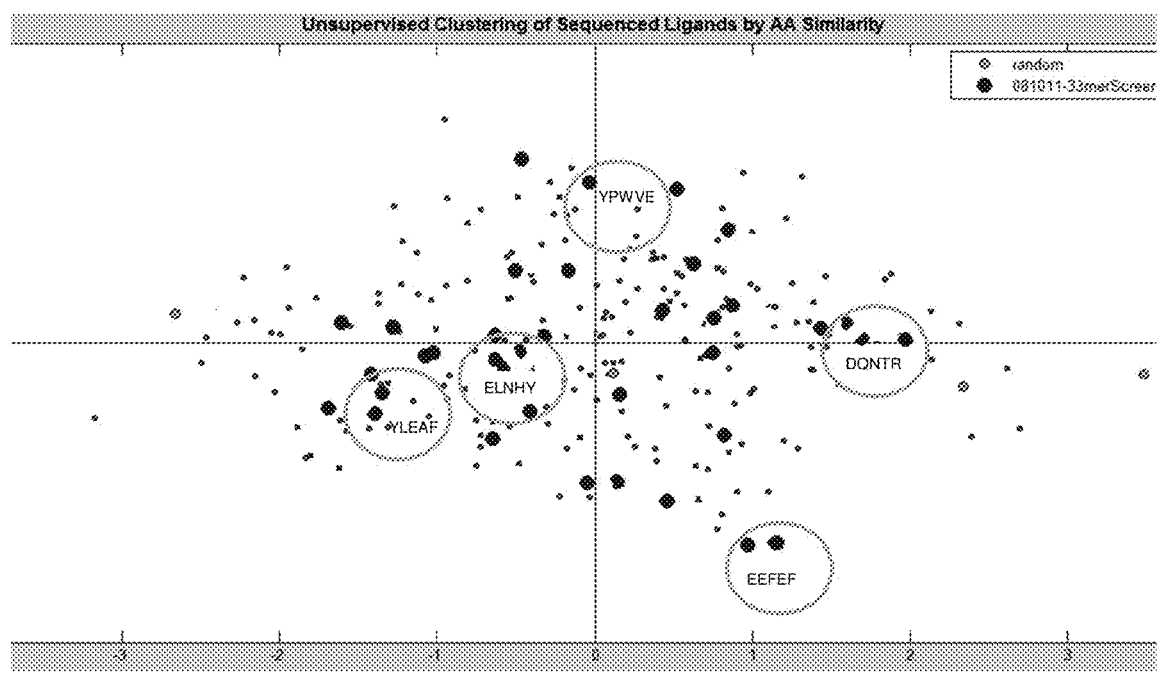
FIG. 41 shows unsupervised clustering of sequence ligands by amino acid similarity: Hit sequences from the anchor screen were analyzed by ClusterLigand v1.0. Circled clusters indicate regions where a peptide was selected and scaled-up as a possible anchor sequence. The potential anchor sequences that were tested were: dqntr, ypwve, eefef, yleaf and elnhy.

Sequence Analysis:

Hit sequences were analyzed via a peptide analysis algorithm, Cluster Ligand v1.0, developed by Integrated Diagnostics, Seattle, Wash. The algorithm analyzes a series of peptides via hydrophobicity and sequence homology and graphs them on a 2D sequence map. Clusters of hits were circled (FIG. 41), and one peptide from each cluster was scaled-up and tested for binding to both wildtype and mutant PH domain. The ligands chosen for scale up were: dqntr, ypwve, eefef, yleaf, and elnhy. These sequences were compared to a known Akt PH Domain binding peptide, AVT-DHPDRWAWEKF[2] (SEQ ID NO: 44).

Streptavidin-Agarose Pulldown Assays for Binding Selectivity:

Pulldown assays were done on Streptavidin Agarose resin from Novachem. The resin was incubated with N-terminally biotinylated anchor peptide candidates identified via the ClusterLigand sequence analysis. The anchor candidate coated beads were then incubated with both wildtype and mutant protein to compare the selectivity of the ligands, as well as the binding ability.

Assays were done with 50 uL of Streptavidin-Agarose slurry (25 uL resin) in Spin-X tubes. Resin was aliquotted into 14 tubes—six ligands plus a blank tested against two different proteins, then washed three times with 1×TBS with 0.25% IPEGAL detergent added. Each set of tubes was incubated with 170 nmol of the appropriate biotinylated ligand in 200 uL 1×HEPES (10 mM HEPES, 150 mM NaCl, 0.25% IPEGAL, 5 mM EDTA) or plain buffer for the blank. Ligand binding was done for one hour at room temperature, then resin was washed three times with 1×HEPES. Resin was blocked with 1×HEPES with 5% BSA for two hours. The anchor-coated resin was then incubated with either wildtype or mutant expressed PH domain protein overnight (~16 hours) in cold room (4° C.). Protein was spun out of tubes, and the resin was washed three times with high salt TBS, then incubated for five minutes in the high salt buffer. The resin was then washed three times with the 1×TBS buffer, and spun out to dry completely. 50 uL of denaturing SDS gel loading buffer with 10% B-mercaptoethanol was added to the samples and they were incubated at 95° C. for ten minutes to denature. The gel loading buffer was spun out of the Spin-X tubes and the samples were run on an Any KD BioRad Premade Gel under denaturing conditions. Gel was transferred to nitrocellulose membrane and western blotted [3]. Proteins were detected using rabbit polyclonal anti-Akt1 antibody (ab64148, Abcam) and an anti-rabbit HRP conjugated secondary anti-body then developed with West Pico Chemilluminescent substrate (Pierce).

Figure 42:
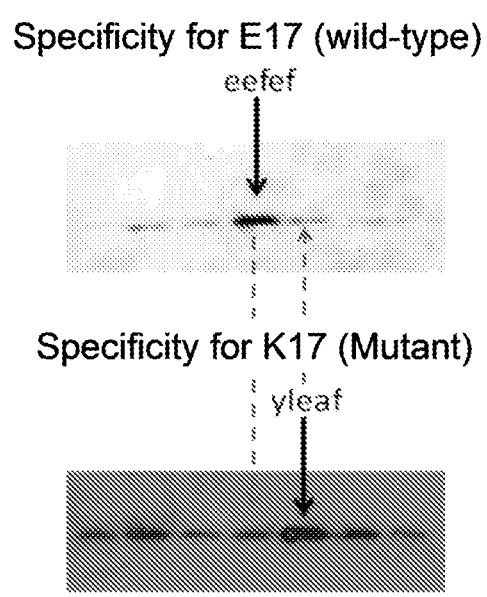
FIG. 42 shows streptavidin-agarose pulldown assays for anchor ligand binding affinity: Streptavidin-agarose was incubated with a panel of potential anchor sequences that were synthesized with biotin tags. These resins were then incubated with either (a) WT or (b) E17K Mutant PHD to measure the amount of pulldown for each potential anchor ligand.

Relative protein band sizes were analyzed to compare binding between the anchor candidates and were used to determine selectivity for either wildtype or mutant PH Domain (FIG. 42). From these assays, eeef (SEQ ID NO: 5) was identified as a capture agent with selectivity for wildtype PH Domain, as it showed the only pulldown of the wildtype protein as well as the least pulldown for the mutant protein. For the mutant protein, yleaf (SEQ ID NO: 16) was chosen, as it showed the greatest binding to the mutant with the least binding to the wildtype. These ligands can be further improved using procedures using procedures known in the art.

TABLE 4

Hit sequences from screen against 33-mer peptide fragment (16 hr screen):

| Sequence | X1 | X2 | X3 | X4 | X5 | SEQ ID NO: |
|---|---|---|---|---|---|---|
| Az4 | e | e | f | e | f | 5 |
| Az8 | f | e | e | a | i | 6 |
| Az2 | e | l | n | h | y | 7 |
| Az2 | h | a | r | h | q | 8 |
| Az2 | h | e | w | v | t | 9 |
| Az4 | n | w | y | a | w | 10 |
| Az4 | n | l | v | p | n | 11 |
| Az2 |   | r | r | r | f | 12 |
| Az4 | a | l | n | s | k | 13 |
| Az8 | p |   | a | y | h | 14 |
| Az2 | n | r | y | v | r | 15 |
| Az8 | y | l | e | a | f | 16 |

Example 7: MicroPET/CT Imaging and Biodistribution Analysis

DOTA-labeled AKT will be labeled with $^{64}$Cu and administered to mice via a 100 µg I.V. tail vein injection or by IP injection. Whole-body imaging will be carried out with microPET scanners using a two hour dynamic scan, followed by microCT imaging. 10 minute static microPET scans will also be carried out at 4 and 6 hours. Biodistribution of labeled capture agent among various organs (e.g., bladder, kidney, gall bladder, liver, brain, and blood) will be analyzed to evaluate clearance and accumulation. Other labels (18-F, 68-Ga, 89-Zr, 124-I, 86-Y, 94m-Tc, 110m-In, 11-C, 76-Br) are contemplated As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Agnew Angew Chem Int Ed Engl 48:4944 (2009)
2. Altomare Oncogene 24:7455 (2005)
3. Borrebaeck Immunol Today 21:379 (2000)
4. Chothia Nature 342:877 (1989)
5. Cohen Nat Rev Drug Discov 1:309 (2002)
6. Erlanson Proc Natl Acad Sci USA 97:9367 (2000)
7. Gao Protein Expr Purif 43:44 (2005)
8. Garcia-Echeverria Oncogene 27:5511 (2008)
9. Jencks Proc Natl Acad Sci USA 78:4046 (1981)
10. Jen-Jacobson Biopolymers 44:153 (1997)
11. Kirkland Biochem Pharmacol 77:1561 (2009)
12. Klein Protein Expr Purif 41:162 (2005)
13. Kodadek J Immunol Methods 340:132 (2009)
14. Kumar Biochim Biophys Acta 1526:257 (2001)
15. Lam Nature 354:82 (1991)
16. Manetsch J Am Chem Soc 126:12809 (2004)
17. Mason Biochem 46:4804 (2007)
18. Meyer J Am Chem Soc 129:13812 (2007)
19. Michaud Nat Biotechnol 21:1509 (2003)
20. Mocharla Angew Chem Int Ed Engl 44:116 (2004)
21. Murray J Comput Aided Mol Des 16:741 (2002)
22. Nguyen Science 282:2088 (1998)
23. Nguyen Chem Biol 7:463 (2000)
24. Niemeyer Trends Biotechnol 23:208 (2005)
25. Obata J Biol Chem 275:36108 (2000)
26. Posy J Med Chem 54:54 (2010)
27. Samson Bioorg Med Chem 3:257 (1995)
28. Samson J Biol Chem 272:11378 (1997)
29. Schildback J Biol Chem 266:4640 (1991)
30. Segel Enzyme Kinetics: Behavior and analysis of rapid equilibrium and steady state enzyme systems. Wiley, New York (1975)
31. Shomin Bioorg Med Chem 17:6196 (2009)
32. Shuker Science 274:1531 (1996)
33. Statsuk J Am Chem Soc 130:17568 (2008)
34. Souroujon Nat Biotech 16:919 (1998)
35. Tornoe J Organic Chem 67:3057 (2002)
36. Vivanco Nat Rev Cancer 2:489 (2002)
37. Whiting Angew Chem Int Ed Engl 45:1435 (2006)
38. Xu Immunity 13:37 (2000)
39. Yang Cancer Res 64:4394 (2004)
40. Zarrinpar Nature 426:676 (2003)
41. Zemlin J Mol Biol 334:733 (2003)

42. Rebecchi, M. J., Scarlata, S., *Ann. Rev. Biophys. Biomol* 1998, 27, 503-528.
43. Carpten, J. B., et al., *Nature* 2007, 448, 439-445.
45. Coin, M. Beyermann, M. Bienert, *Nat. Protocols* 2007, 2, 3247.
46. M. Hiromura, F. Okada, T. Obata, D. Auguin, T. Shibata, C. Roumestand, M. Noguchi, *J Biol Chem* 2004, 279(51), 53407.
47. H. Towbin, T. Staehelin, J. Gordon, *Proc Natl Acad Sci* 1979, 76(9), 4350.

What is claimed is:

1. A method of imaging at least one permeabilized cancer cell associated with increased Akt expression and/or activity in vitro, comprising administering a detectable amount of a stable, synthetic triligand capture agent that specifically binds Akt to a permeabilized cancer cell in vitro,
   wherein the capture agent comprises an anchor ligand, a secondary ligand, and a tertiary ligand, and the capture agent binds to a non-ATP and non-peptide substrate binding site of Akt,
   wherein the capture agent comprises a label,
   wherein the capture agent is capable of allosterically inhibiting Akt activity upon binding to the binding site,
   wherein said anchor ligand comprises the peptide sequence Az8-VFYRLGY-CONH$_2$ (SEQ ID NO: 17), and wherein Az8 represents and azide amino acid having the structure:

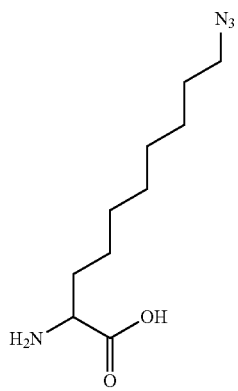 [SMILES: [N-]=[N+]=NCCCCCCCCC(N)C(=O)O]

6. The method of claim 3, wherein the capture agent is stable at a pH in the range of about 3 to about 8.

7. The method of claim 3, wherein the capture agent is labeled with $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C or $^{76}$Br.

8. The method of claim 3, wherein said secondary ligand comprises the peptide sequence Pra-FWFLRG-CONH$_2$ (SEQ ID NO: 18).

9. The method of claim 3, wherein said tertiary ligand comprises the peptide sequence Ac-C8-RHERI-CONH$_2$ (SEQ ID NO: 19).

10. The method of claim 3, wherein said capture agent has the structure:

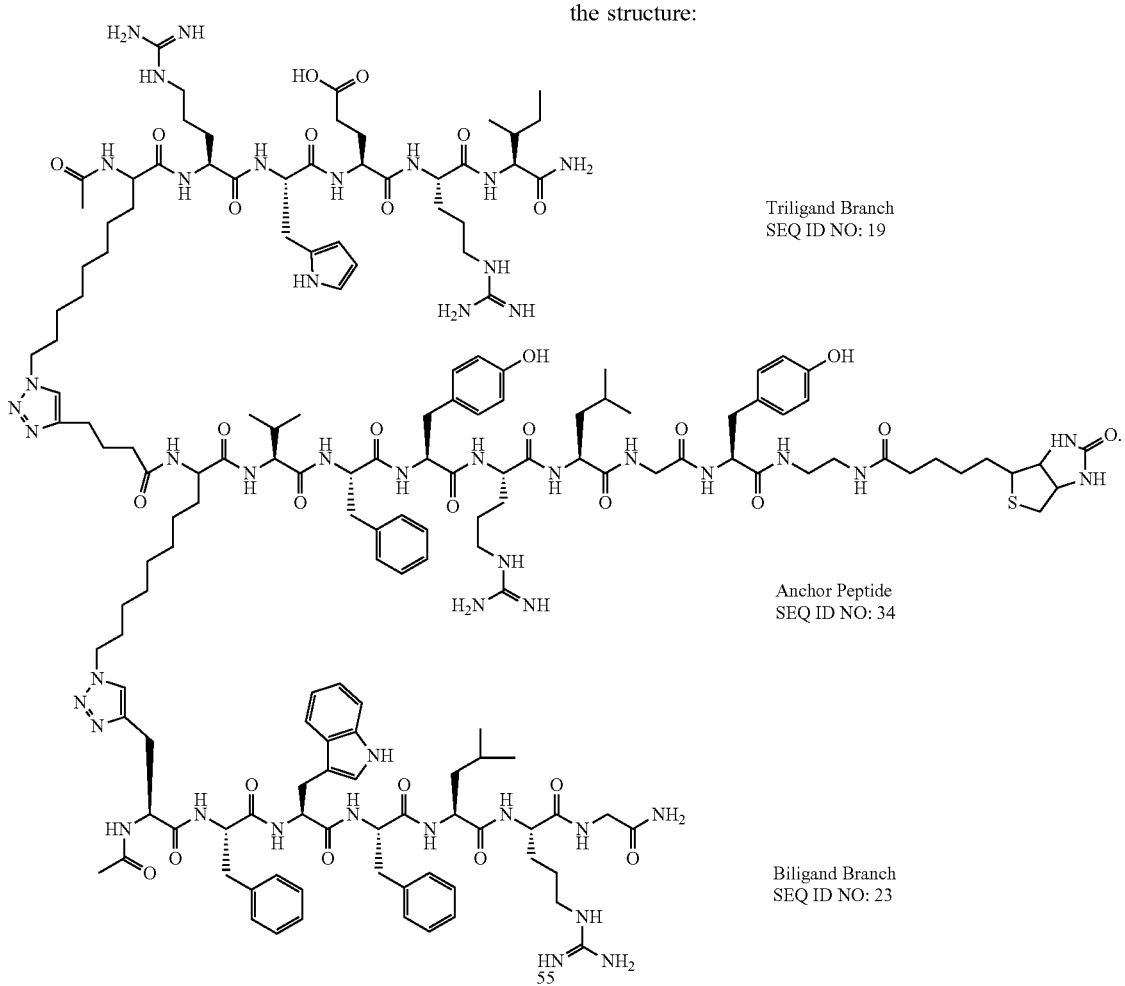

to the at least one permeabilized cancer cell and detecting the label on the capture agent thereby imaging the at least one permeabilized cancer cell in vitro.

2. The method of claim 1, wherein the capture agent is stable in storage as a lyophilized powder.

3. The method of claim 1, wherein the capture agent is stable in storage at a temperature of about −80° C. to about 40° C.

4. The method of claim 3, wherein the capture agent is stable in storage at room temperature.

5. The method of claim 3, wherein the capture agent is stable in serum for at least 24 hours.

11. The method according to claim 3, wherein the linkage between one or more of the anchor ligand, secondary ligand, and tertiary ligand comprises a 1,4-substituted-1,2,3-triazole residue (Tz4).

12. A method of detecting Akt in a biological sample using an immunoassay, wherein the immunoassay utilizes a stable, synthetic triligand capture agent that specifically binds Akt, wherein the capture agent comprises an anchor ligand, a secondary ligand, and a tertiary ligand, and the capture agent binds to a non-ATP and non-peptide substrate binding site of Akt, wherein the capture agent comprises a label,
wherein the capture agent is capable of allosterically inhibiting Akt activity upon binding to the binding site,
wherein said anchor ligand comprises the peptide sequence Az8-VFYRLGY-CONH$_2$ (SEQ ID NO: 17), and
wherein Az8 represents and azide amino acid having the structure:

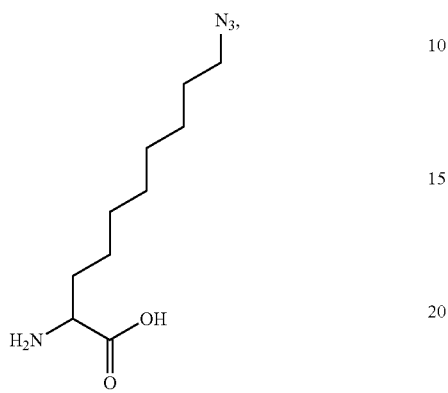

and wherein said capture agent replaces an antibody or its equivalent in the immunoassay.

13. The method of claim 12, wherein the immunoassay is selected from the group of Western blot, pull-down assay, dot blot, and ELISA.

* * * * *

SEQUENCE LISTING

```
<160> NUMBER OF SEQ ID NOS: 128

<210> SEQ ID NO 1
<211> LENGTH: 480
<212> TYPE: PRT
<213> ORGANISM: Homo sapiens
<220> FEATURE:
<221> NAME/KEY: misc_feature
<223> OTHER INFORMATION: Homo sapiens Akt1 (GenBank accession number
      AAL55732)

<400> SEQUENCE: 1

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
```

```
                305                 310                 315                 320
Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra at 5' end
<220> FEATURE:
<221> NAME/KEY: misc_feature
<222> LOCATION: (1)..(5)
<223> OTHER INFORMATION: Any Xaa is any of the 18 D amino acids except
      D-Met and D-Cys

<400> SEQUENCE: 2

Xaa Xaa Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Any Xaa is any of the 18 D amino acids except
      D-Met and D-Cys
<220> FEATURE:
<221> NAME/KEY: MOD_RES
<222> LOCATION: (5)..(5)
<223> OTHER INFORMATION: Pra at 3' end

<400> SEQUENCE: 3

Xaa Xaa Xaa Xaa Xaa
1               5

<210> SEQ ID NO 4
<211> LENGTH: 5
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids
<220> FEATURE:
<221> NAME/KEY: MOD_RES
<222> LOCATION: (1)..(1)
<223> OTHER INFORMATION: D-Pra at 5' end

<400> SEQUENCE: 4

Trp Lys Val Lys Leu
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 5

Glu Glu Phe Glu Phe
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 6

Phe Glu Glu Ala Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 7

Glu Leu Asn His Tyr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
```

```
<223> OTHER INFORMATION: D-amino acids

<400> SEQUENCE: 8

His Ala Arg His Gln
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 9

His Glu Trp Val Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 10

Asn Trp Tyr Ala Trp
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 11

Asn Leu Val Pro Asn
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 12

Arg Arg Arg Phe
1

<210> SEQ ID NO 13
<211> LENGTH: 5
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 13

Ala Leu Asn Ser Lys
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 14

Pro Ala Tyr His
1

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 15

Asn Arg Tyr Val Arg
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: D-amino acids

<400> SEQUENCE: 16

Tyr Leu Glu Ala Phe
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
<220> FEATURE:
<221> NAME/KEY: MOD_RES
<222> LOCATION: (7)..(7)
<223> OTHER INFORMATION: CONH2 on 3' end
```

<400> SEQUENCE: 17

Val Phe Tyr Arg Leu Gly Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra (propargylglycine) on 5' end
<220> FEATURE:
<221> NAME/KEY: MOD_RES
<222> LOCATION: (6)..(6)
<223> OTHER INFORMATION: CONH2 on 3' end

<400> SEQUENCE: 18

Phe Trp Phe Leu Arg Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ac-C8 on 5' end
<220> FEATURE:
<221> NAME/KEY: MOD_RES
<222> LOCATION: (5)..(5)
<223> OTHER INFORMATION: CONH2 on 3' end

<400> SEQUENCE: 19

Arg His Glu Arg Ile
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
<220> FEATURE:
<221> NAME/KEY: misc_feature
<222> LOCATION: (1)..(1)
<223> OTHER INFORMATION: Xaa can be His, Glu, Ile, Gln, Val, or Gly
<220> FEATURE:
<221> NAME/KEY: misc_feature
<222> LOCATION: (2)..(2)
<223> OTHER INFORMATION: Xaa can be Pro, Phe, Ala, Gly, His, or Thr
<220> FEATURE:
<221> NAME/KEY: misc_feature
<222> LOCATION: (3)..(3)
<223> OTHER INFORMATION: Xaa can be Glu, Asp, Val, or Tyr
<220> FEATURE:
<221> NAME/KEY: misc_feature
<222> LOCATION: (4)..(4)
<223> OTHER INFORMATION: Xaa can be Asn, Gly, Asp, Pro, Gln, Arg, or Thr
<220> FEATURE:
<221> NAME/KEY: misc_feature
<222> LOCATION: (5)..(5)
<223> OTHER INFORMATION: Xaa can be Arg, Leu, Ile, Thr, Gly, Glu, or Asp

```
<220> FEATURE:
<221> NAME/KEY: MOD_RES
<222> LOCATION: (8)..(8)
<223> OTHER INFORMATION: TG (TentaGel resin) on 3' end

<400> SEQUENCE: 20

Xaa Xaa Xaa Xaa Xaa Gly Tyr Met
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
<220> FEATURE:
<221> NAME/KEY: misc_feature
<222> LOCATION: (1)..(1)
<223> OTHER INFORMATION: Xaa can be Ala, Glu, His, Lys, Leu, or Arg
<220> FEATURE:
<221> NAME/KEY: misc_feature
<222> LOCATION: (2)..(2)
<223> OTHER INFORMATION: Xaa can be Ala, His, Lys, Leu, or Arg
<220> FEATURE:
<221> NAME/KEY: misc_feature
<222> LOCATION: (3)..(3)
<223> OTHER INFORMATION: Xaa can be Asp, His, Lys, Leu, or Glu
<220> FEATURE:
<221> NAME/KEY: misc_feature
<222> LOCATION: (4)..(4)
<223> OTHER INFORMATION: Xaa can be Asp, His, Ile, Lys, Asn, Arg, or Ser
<220> FEATURE:
<221> NAME/KEY: misc_feature
<222> LOCATION: (5)..(5)
<223> OTHER INFORMATION: Xaa can be Phe, Gly, His, Ile, or Lys
<220> FEATURE:
<221> NAME/KEY: MOD_RES
<222> LOCATION: (8)..(8)
<223> OTHER INFORMATION: TG (TentaGel resin) on 3' end

<400> SEQUENCE: 21

Xaa Xaa Xaa Xaa Xaa Gly Tyr Met
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: Bio(1) or Bio(2) on 3' end

<400> SEQUENCE: 22

Val Phe Tyr Arg Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ac-Pra on 5' end
```

```
<220> FEATURE:
<221> NAME/KEY: MOD_RES
<222> LOCATION: (6)..(6)
<223> OTHER INFORMATION: CONH2 on 3' end

<400> SEQUENCE: 23

Phe Trp Phe Leu Arg Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
<220> FEATURE:
<221> NAME/KEY: MOD_RES
<222> LOCATION: (7)..(7)
<223> OTHER INFORMATION: Biotin on 3' end

<400> SEQUENCE: 24

Val Phe Tyr Arg Leu Gly Tyr
1               5

<210> SEQ ID NO 25
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 25
aaggagggat ccatgggcag cagccat                                      27

<210> SEQ ID NO 26
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 26
tggtgtgaat tcttatcact tgtcatcgtc atc                               33

<210> SEQ ID NO 27
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 27
gccgccacca tg                                                      12

<210> SEQ ID NO 28
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 28
accgtcccac catcggggcc gccaccatgg gcagcagcca t                      41
```

<210> SEQ ID NO 29
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 29
atggctgctg cccatggtgg cggccccgat ggtgggacgg t    41

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: AzX (Az2, Az4, or Az8) at 5' end
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(6)
<223> OTHER INFORMATION: Any Xaa is one of 18 natural L-amino acids
<220> FEATURE:
<221> NAME/KEY: MOD_RES
<222> LOCATION: (8)..(8)
<223> OTHER INFORMATION: TG (TentaGel resin) at 3' end

<400> SEQUENCE: 30

Xaa Xaa Xaa Xaa Xaa Gly Tyr Met
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Arg Pro Arg Ala Ala Thr Phe
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra (propargylglycine) at 5' end
<220> FEATURE:
<221> NAME/KEY: misc_feature
<222> LOCATION: (1)..(5)
<223> OTHER INFORMATION: Any Xaa can be any naturally occurring amino
      acid
<220> FEATURE:
<221> NAME/KEY: MOD_RES
<222> LOCATION: (7)..(7)
<223> OTHER INFORMATION: TG (TentaGel resin) at 3' end

<400> SEQUENCE: 32

Xaa Xaa Xaa Xaa Xaa Gly Met
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: Bio at 3' end

<400> SEQUENCE: 33

Val Phe Tyr Arg Leu Gly Tyr
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Fmoc-C8N3 at 5' end
<220> FEATURE:
<221> NAME/KEY: MOD_RES
<222> LOCATION: (7)..(7)
<223> OTHER INFORMATION: Biotin at 3' end

<400> SEQUENCE: 34

Val Phe Tyr Arg Leu Gly Tyr
1               5

<210> SEQ ID NO 35
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: aminated oligonucleotide: NH2-(CH2)6 at 5' end

<400> SEQUENCE: 35
gggacaatta ctatttacaa ttacaatgct cacgtggtac gagttcgtct cccagg        56

<210> SEQ ID NO 36
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 36
taatacgact cactataggg acaattacta tttacaatta ca                       42

<210> SEQ ID NO 37
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 37
accgctgcca gaccccgatt tggcctggga gacgaactcg                          40

```
<210> SEQ ID NO 38
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra at 5' end

<400> SEQUENCE: 38

Phe Trp Phe Leu Arg Gly
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ac-C8N3 at 5' end

<400> SEQUENCE: 39

Val Phe Tyr Arg Leu Gly Tyr
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ac-C8N3 at 5' end
<220> FEATURE:
<221> NAME/KEY: MOD_RES
<222> LOCATION: (7)..(7)
<223> OTHER INFORMATION: Biotin at 3' end

<400> SEQUENCE: 40

Val Phe Tyr Arg Leu Gly Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ac-Pra at 5' end
<220> FEATURE:
<221> NAME/KEY: MOD_RES
<222> LOCATION: (6)..(6)
<223> OTHER INFORMATION: Biotin at 3' end

<400> SEQUENCE: 41

Phe Trp Phe Leu Arg Gly
1               5

<210> SEQ ID NO 42
<211> LENGTH: 5
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ac-C8N3 at 5' end
<220> FEATURE:
<221> NAME/KEY: MOD_RES
<222> LOCATION: (5)..(5)
<223> OTHER INFORMATION: CONH2 at 3' end

<400> SEQUENCE: 42

Arg His Glu Arg Ile
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: C8N3 at 5' end
<220> FEATURE:
<221> NAME/KEY: MOD_RES
<222> LOCATION: (7)..(7)
<223> OTHER INFORMATION: CONH2 at 3' end

<400> SEQUENCE: 43

Val Phe Tyr Arg Leu Gly Tyr
1               5

<210> SEQ ID NO 44
<211> LENGTH: 14
<212> TYPE: PRT
<213> ORGANISM: Artificial Sequence
<220> FEATURE:
<223> OTHER INFORMATION: Synthetic peptide

<400> SEQUENCE: 44

Ala Val Thr Asp His Pro Asp Arg Trp Ala Trp Glu Lys Phe
1               5                   10

<210> SEQ ID NO 45
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Any Xaa is one of 18 natural L-amino acids
<220> FEATURE:
<221> NAME/KEY: MOD_RES
<222> LOCATION: (1)..(1)
<223> OTHER INFORMATION: AzX (Az2, Az4, or Az8) on 5' end

<400> SEQUENCE: 45

Xaa Xaa Xaa Xaa Xaa Gly Tyr Met
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: Az4 on 5' end

<400> SEQUENCE: 46

His His Thr Asn Arg Gly Tyr Met
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 47

Arg Phe Ile Asn Arg Gly Tyr Met
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 48

Val Lys Tyr Arg Leu Gly Tyr Met
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 49

Ile Leu Ser Arg Leu Gly Tyr Met
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 50

Ile Ala Pro Asp Pro Gly Tyr Met
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 51

Gly Pro Asp Pro Gly Gly Tyr Met
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 52

Ser Glu Arg Thr Trp Gly Tyr Met
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 53

Glu Arg Tyr Gln Thr Gly Tyr Met
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 54

Gln Thr Asp Ser His Gly Tyr Met
1               5

<210> SEQ ID NO 55
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
```

```
<400> SEQUENCE: 55

Gln Gly Val Pro Glu Gly Tyr Met
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 56

Tyr Asn Val Gln Tyr Gly Tyr Met
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 57

His His Lys Gly Ala Gly Tyr Met
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 58

Glu Phe His Pro Ile Gly Tyr Met
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 59

Ile Gly Val Gly Asp Gly Tyr Met
1               5

<210> SEQ ID NO 60
<211> LENGTH: 8
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 60

Glu Trp Leu Phe Asn Gly Tyr Met
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 61

Ile Ala Glu Pro Ile Gly Tyr Met
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 62

Ala Thr Glu Asp Thr Gly Tyr Met
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 63

Val Gly Asp Thr Thr Gly Tyr Met
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 64

His Ala Glu Pro Tyr Gly Tyr Met
1               5
```

```
<210> SEQ ID NO 65
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 65

Leu Gly Thr Tyr Pro Gly Tyr Met
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 66

His Gly Ile Gln Pro Gly Tyr Met
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 67

Ile Ser His Asp Ser Gly Tyr Met
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 68

Val Thr Tyr Arg Arg Gly Tyr Met
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
```

<400> SEQUENCE: 69

Ile Ala Val Arg Arg Gly Tyr Met
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 70

Ile Thr Val Arg Arg Gly Tyr Met
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 71

Gln Phe Val Arg Arg Gly Tyr Met
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 72

Gln Thr Val Arg Arg Gly Tyr Met
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 73

Gln Ala Val Arg Arg Gly Tyr Met
1               5

<210> SEQ ID NO 74
<211> LENGTH: 8
<212> TYPE: PRT
<213> ORGANISM: Artificial Sequence

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 74

Val Phe Val Arg Arg Gly Tyr Met
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 75

His Ala Val Arg Arg Gly Tyr Met
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 76

Val Phe Glu Arg Arg Gly Tyr Met
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 77

Val Phe Glu Arg Leu Gly Tyr Met
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 78

Val Phe Tyr Arg Leu Gly Tyr Met
1               5
```

```
<210> SEQ ID NO 79
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 79

Val Phe Tyr Arg Leu Gly Tyr Met
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 80

Val Ala Tyr Arg Leu Gly Tyr Met
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 81

Val Phe Tyr Thr Arg Gly Tyr Met
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 82

Val Gly Tyr Arg Ile Gly Tyr Met
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

<223> OTHER INFORMATION: Az8 on 5' end

<400> SEQUENCE: 83

Val Gly Tyr Arg Ile Gly Tyr Met
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end
<220> FEATURE:
<221> NAME/KEY: misc_feature
<222> LOCATION: (1)..(5)
<223> OTHER INFORMATION: Any Xaa is one of 18 natural L-amino acids

<400> SEQUENCE: 84

Xaa Xaa Xaa Xaa Xaa Gly Met
1               5

<210> SEQ ID NO 85
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 85

Phe Pro Phe Phe Gly Met
1               5

<210> SEQ ID NO 86
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 86

Ser Phe Phe Trp Gly Met
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 87

Phe Trp Arg Ile Tyr Gly Met
1               5

```
<210> SEQ ID NO 88
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 88

Phe Trp Phe Leu Arg Gly Met
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 89

Phe Phe Asn Phe Arg Gly Met
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 90

Phe Phe Phe Arg Thr Gly Met
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 91

Ala Phe Phe Arg Gly Gly Met
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end
```

```
<400> SEQUENCE: 92

Arg Phe Gln Tyr Tyr Gly Met
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Pra on 5' end

<400> SEQUENCE: 93

Trp Asp Thr Asp Ser Gly Met
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Any Xaa is one of 18 natural L-amino acids
<220> FEATURE:
<221> NAME/KEY: MOD_RES
<222> LOCATION: (1)..(1)
<223> OTHER INFORMATION: AzX (Az2, Az4, or Az8) on 5' end

<400> SEQUENCE: 94

Xaa Xaa Xaa Xaa Xaa
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 95

Arg Arg Asp Val Ala
1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 96

His Asp Lys Ile Ile
1               5
```

```
<210> SEQ ID NO 97
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 97

Lys His Leu Gly His
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 98

Lys Thr His Arg His
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 99

His Leu His Pro Lys
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 100

Ala Lys His Ser His
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
```

```
<400> SEQUENCE: 101

Ser Lys His His Lys
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 102

Gly Arg His Lys His
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 103

Glu His Leu Ser Arg
1               5

<210> SEQ ID NO 104
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 104

Asn Lys Ile Tyr Lys
1               5

<210> SEQ ID NO 105
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 105

Ala Ser Leu Asn His
1               5

<210> SEQ ID NO 106
<211> LENGTH: 5
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 106

Asp Gln Thr Asp Lys
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 107

Ala Ala Asn His Glu
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 108

Lys His Gly Asp Phe
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 109

His Lys Phe Lys His
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 110

Lys Lys His Asp His
1               5
```

```
<210> SEQ ID NO 111
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 111

His Leu Leu His Gly
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az4 on 5' end

<400> SEQUENCE: 112

Leu His Asp His Lys
1               5

<210> SEQ ID NO 113
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 113

Arg Arg Glu Ser Lys
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 114

Arg Val His Ile Phe
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end
```

```
<400> SEQUENCE: 115

Lys Trp His Lys Lys
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 116

Leu Lys His Asp Lys
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 117

Leu Leu His Arg His
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az2 on 5' end

<400> SEQUENCE: 118

Phe Ala Gln Asn Tyr
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(5)
<223> OTHER INFORMATION: Any Xaa is one of 18 natural L-amino acids
<220> FEATURE:
<221> NAME/KEY: MOD_RES
<222> LOCATION: (1)..(1)
<223> OTHER INFORMATION: Az8 on 5' end

<400> SEQUENCE: 119

Xaa Xaa Xaa Xaa Xaa
1               5
```

```
<210> SEQ ID NO 120
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 120

Leu Arg Lys Ile Gly
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 121

Leu Lys Ile Phe Gly
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 122

Glu Lys Asp His Gly
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end

<400> SEQUENCE: 123

Glu Leu Glu His Ile
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Az8 on 5' end
```

```
<400> SEQUENCE: 124

Arg His Glu Arg Ile
1               5

<210> SEQ ID NO 125
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Az8 on 5' end

<400> SEQUENCE: 125

Lys Ala His Lys His
1               5

<210> SEQ ID NO 126
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 126

Phe Tyr Gly Asn His
1               5

<210> SEQ ID NO 127
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 127

Tyr Tyr Arg Phe Gly
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 128

His Asp Gly Gly Phe
1               5
```